(12) United States Patent
Samaha et al.

(10) Patent No.: US 10,874,874 B2
(45) Date of Patent: Dec. 29, 2020

(54) TRANSORBITAL NIR LIGHT THERAPY DEVICE

(71) Applicant: Janssen Pharmaceutica NV, Beerse (BE)

(72) Inventors: Alexander Samaha, Newton, MA (US); Griffin Cummings, Raynham, MA (US); Thomas M. DiMauro, Southboro, MA (US); Alexandru Paunescu, Clinton, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/732,255

(22) Filed: Dec. 31, 2019

(65) Prior Publication Data

US 2020/0324136 A1 Oct. 15, 2020

Related U.S. Application Data

(63) Continuation-in-part of application No. 16/419,369, filed on May 22, 2019.

(60) Provisional application No. 62/902,182, filed on Sep. 18, 2019, provisional application No. 62/892,513, filed on Aug. 27, 2019, provisional application No. 62/871,889, filed on Jul. 9, 2019, provisional application No. 62/865,468, filed on Jun. 24, 2019, provisional application No. 62/859,971, filed on Jun. 11, 2019, provisional application No. 62/844,855, (Continued)

(51) Int. Cl.
*A61N 5/06* (2006.01)
*A61N 5/067* (2006.01)

(52) U.S. Cl.
CPC ...... *A61N 5/0613* (2013.01); *A61N 2005/067* (2013.01); *A61N 2005/0651* (2013.01); *A61N 2005/0659* (2013.01); *A61N 2005/0665* (2013.01)

(58) Field of Classification Search
CPC .............................. A61N 5/06; A61N 5/0613
See application file for complete search history.

(56) References Cited

U.S. PATENT DOCUMENTS 4,283,127 A  8/1981  Rosenwinkel et al.
6,350,275 B1  2/2002  Vreman et al.
(Continued)

OTHER PUBLICATIONS

[No Author Listed]—Radian Thermal Products, "White Paper: Heat Pipes & Vapor Chambers", Nov. 2014, 9 pages, https://www.radianheatsinks.com/wp-content/uploads/2017/07/Heat-Pipes-and-Vapor-Chambers.pdf.

(Continued)

*Primary Examiner* — Gary Jackson
*Assistant Examiner* — Zahed Kabir
(74) *Attorney, Agent, or Firm* — Nutter McClennen & Fish LLP

(57) ABSTRACT

A device for treating the brain includes a light source configured to emit near infrared light. The device also includes a collimator configured to receive the near infrared light emitted by the light emitter. The collimator is further configured to collimate the near infrared light. The device also includes an optic configured to focus collimated light. A reflector of the device is configured to change a direction of the collimated light. The reflector is at a distal end of the device, and the distal end is configured to fit between an upper portion of an eyelid of a patient and an orbital socket of the patient.

19 Claims, 51 Drawing Sheets

Related U.S. Application Data filed on May 8, 2019, provisional application No. 62/834,394, filed on Apr. 15, 2019.

(56) References Cited

U.S. PATENT DOCUMENTS

| | | | |
|---|---|---|---|
| 6,559,096 | B1 | 5/2003 | Smith et al. |
| 6,688,132 | B2 | 2/2004 | Smith et al. |
| 6,701,724 | B2 | 3/2004 | Smith et al. |
| 6,857,739 | B1 | 2/2005 | Watson |
| 6,968,711 | B2 | 11/2005 | Smith et al. |
| 8,167,920 | B2 | 5/2012 | DiMauro et al. |
| 8,734,498 | B2 | 5/2014 | DiMauro et al. |
| 9,470,908 | B1 | 10/2016 | Frankel et al. |
| 10,561,857 | B2 | 2/2020 | Toselli et al. |
| 2001/0028431 | A1 | 10/2001 | Rossin |
| 2004/0215293 | A1 | 10/2004 | Eells et al. |
| 2005/0278003 | A1 | 12/2005 | Feldman |
| 2006/0136018 | A1 | 6/2006 | Lack et al. |
| 2006/0198128 | A1 | 9/2006 | Piepgras et al. |
| 2006/0259100 | A1 | 11/2006 | Hilburg |
| 2007/0195515 | A1 | 8/2007 | Waters |
| 2007/0233207 | A1 | 10/2007 | Poirrier et al. |
| 2008/0062682 | A1 | 3/2008 | Hoelen et al. |
| 2008/0193664 | A1 | 8/2008 | Gonzalez et al. |
| 2008/0233053 | A1 | 9/2008 | Gross et al. |
| 2008/0262575 | A1 | 10/2008 | Aunio et al. |
| 2010/0004499 | A1* | 1/2010 | Brigatti ............... A61N 5/1017 600/7 |
| 2010/0324631 | A1 | 12/2010 | Tass et al. |
| 2011/0060266 | A1 | 3/2011 | Streeter et al. |
| 2011/0077548 | A1 | 3/2011 | Torch |
| 2011/0181832 | A1 | 7/2011 | Smith et al. |
| 2011/0295345 | A1 | 12/2011 | Wells et al. |
| 2011/0319878 | A1 | 12/2011 | DiMauro et al. |
| 2012/0215291 | A1 | 8/2012 | Pugh et al. |
| 2013/0066404 | A1 | 3/2013 | Tapper et al. |
| 2013/0201285 | A1 | 8/2013 | Mao et al. |
| 2014/0313716 | A1 | 10/2014 | Lang |
| 2014/0330129 | A1 | 11/2014 | Grenon et al. |
| 2014/0358199 | A1 | 12/2014 | Lim |
| 2014/0376232 | A1 | 12/2014 | Behr et al. |
| 2015/0005750 | A1 | 1/2015 | Kelleher et al. |
| 2016/0106950 | A1 | 4/2016 | Vasapollo |
| 2016/0263395 | A1 | 9/2016 | Siegel et al. |
| 2016/0342206 | A1 | 11/2016 | Shazly et al. |
| 2017/0087017 | A1* | 3/2017 | Iseli ..................... A61F 9/00821 |
| 2017/0296051 | A1* | 10/2017 | Kislinger ................. A61B 3/14 |
| 2018/0021032 | A1 | 1/2018 | DiMauro et al. |
| 2018/0104514 | A1 | 4/2018 | Gertner et al. |
| 2018/0188556 | A1 | 7/2018 | Portney |
| 2018/0193664 | A1* | 7/2018 | DiMauro ............. A61N 5/0622 |
| 2018/0264284 | A1* | 9/2018 | Alvarez ............... A61N 5/0618 |
| 2019/0106543 | A1 | 4/2019 | Chintapalli et al. |

OTHER PUBLICATIONS

[No Author Listed]—"Point-of-care Concussion Therapy", Office for Technology Commercialization, University of Minnesota—Driven to Discover, Technology #20180342, 2018,Regents of the University of Minnesota, 3 pages.

[No Author Listed]—"Vielight: The Future of Brain Photobiomodulation", https://vielight.com/brain-photobiomodulation-devices/, Vielight, Inc., accessed Jan. 10, 2020, 11 pages.

[No Author Listed]—"MedX Health for Concussions: Rehab Laser Console System", https://medxhealth.com/en/product-rehab-console/, accessed Jan. 20, 2020, 4 pages.

Anders, et al.—"Light Supports Neurite Outgrowth of Human Neural Progenitor Cells in Vitro: The Role of P2Y Receptors", IEEE, Journal of Selected Topics in Quantum Electronics, Jan.-Feb. 2008, vol. 14 Issue 1, pp. 118-125.

Aurora CTS, Aurora Concussion Therapy Systems, Inc.—"Helping the brain heal faster", Home Page http://aurora-cts.com/, accessed Jan. 10, 2020, 1 page.

Bartels, et al.—"The neural correlates of maternal and romantic love", NeuroImage, Mar. 2004, vol. 21, Issue 3, pp. 1155-1166, by Elsevier.

Blanco, et al.—"Improving executive function using transcranial infrared laser stimulation", Journal of Neuropsychology, Nov. 28, 2016, published in final form Mar. 2017, vol. 11, Issue 1, pp. 14-25.

Bozkurt, "Safety Assessment of Near Infrared Light Emitting Diodes for Diffuse Optical Measurements", Biomedical Engineering OnLine, 2004, 3:9, 10 pages.

Byrnes, "Light Promotes Regeneration and Functional Recovery and Alters the Immune Response After Spinal Cord Injury", Lasers Surg. Medicine, 2005, 9999, pp. 1-15.

Byrnes, "Light promotes regeneration and functional recovery and alters the immune response after spinal cord injury", Lasers Surgery Medicine, Mar. 2005, 36(3) 171-85, [Abstract].

Byrnes, "Low Power Laser Irradiation Alters Gene Expression of Olfactory Ensheathing Cells in Vitro", Lasers Surg Med., Aug. 2005, vol. 37, issue 2, pp. 161-171, (Abstract).

Cassano et al., "Near-Infrared Transcranial Radiation for Major Depressive Disorder: Proof of Concept Study", Psychiatry J. 2015, 352979, pp. 1-8.

Cassano et al.—"Selective photobiomodulation for emotion regulation: model-based dosimetry study", https://www.spiedigitallibrary.org/journals/neurophotonics/volume-6/issue-1/015004/Selective-photobiomodulation-for-emotion-regulation-model-based-dosimetry-study/10.1117/1.NPh.6.1.015004.full?SSO=1, Neurophotonics SPIE Digital Library, vol. 6, Issue 1, Epub. Feb. 7, 2019, 13 pages.

Cho, "Effect of Low-level Laser Therapy on Osteoarthropathy in Rabbig", In Vivo, Sep.-Oct. 2004, vol. 18, Issue 5, pp. 585-591.

Dimauro et al.—"Project Pleasant: Transorbital Near infrared Light Therapy for the Orbitofrontal Cortex of the Injured Brain", MIT write-up, May 19, 2019, 2 pages.

Fahim, "Orbitofrontal dysfunction in a monozygotic twin discordant for postpartum affective psychosis: a functional magnetic resonance imaging study", Bipolar Disorders 2007, vol. 9, pp. 541-545.

Geneva, "Photobiomodulation for the treatment of retinal diseases: a review", Int. J. Ophthalmol., Jan. 18, 2016, vol. 9, Issue 1, pp. 145-152.

Gorbatenkova, "Reactivation of superoxide dismutase by the helium-neon laser irradiation", Biofizika, Jul.-Aug. 1988, vol. 33, Issue 4, pp. 717-719 (Abstract).

Hamblin—"Shining light on the head: Photobiomodulation for brain disorders", BBA Clinical, vol. 6 (2016), Oct. 1, 2016, pp. 113-124, published by Elsevier B.V.

International Searching Authority—International Search Report and Written Opinion for International Application No. PCT/US2018/013081, dated Apr. 5, 2018, 9 pages.

Kamanli—"Plasma lipid peroxidation and antioxidant levels in patients with rheumatoid arthritis", Cell Biochemistry and Function, 2004, vol. 22, pp. 53-57.

Karu, "Suppression of Human Blood Chemiluminescence by Diode Laser Irradiation at Wavelengths 660, 820, 880 or 950 nm", Laser Therapy, Feb. 27, 1993,vol. 5, pp. 103-109.

Keedy, "An overview of intracranial aneurysms", McGill Journal of Medicine, 2006, vol. 9, Issue 2, pp. 141-146.

King, "Doing the right thing: A common neural circuit for appropriate violent or compassionate behavior", NeuroImage, 2006, vol. 30, pp. 1069-1076.

Kringelbach, "A Specific and Rapid Neural Signature for Parental Instinct", PLoS ONE, 2008, Feb. 27, 2008, vol. 3, Issue 2, e1664, pp. 1-7.

Kroczek, "Prefrontal functional connectivity measured with near-infrared spectroscopy during smoking cue exposure", Addiction Biology, 2015, vol. 22, Issue 2, 2 pages (Abstract).

Leibenluft, "Mothers' neural activation in response to pictures of their children and other children", Biololgy Psychiatry, Aug. 15, 2004, vol. 56, Issue 4, pp. 225-232 (Abstract).

Lenzi, "Neural basis of maternal communication and emotional expression processing during infant preverbal stage", Cereb Cortex, May 2009, vol. 19, Issue 5, pp. 1124-1133.

(56) References Cited

OTHER PUBLICATIONS

Leon-Carrion, "Functional Near-infrared Spectroscopy (fNIRS): Principles and Neuroscientific Applications", Neuroimaoino—Methods, Prof. Peter Bright (Ed.), 2012, ISBN:978-953-51-0097-3, In Tech, pp. 47-74.
Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Laser Suro. Med., 2002, vol. 31, pp. 283-288.
Liang, "Photobiomodulation partially rescues visual cortical neurons from cyanide-induced apoptosis", Neuroscience., May 12, 2006; vol. 139, Issue 2, pp. 639-649.
Lim, "Inventor's Notes on Whole Brain Photobiomodulation with Vielight Neuro—a Transcranial-Intranasal Light Therapy Combination", Jan. 2016, pp. 8 and 16).
Lim, "The Potential of Intranasal Light Therapy for Brain Stimulation", Presented at the NAALT Conference, Palm Beach Gardens, Florida, Feb. 2, 2013, pp. 1-16.
Manji, "Impairments of Neuroplasticity and Cellular Resilience in Severe Mood Disorders: Implications for the Development of Novel Therapeutics", Psychopharmacol Bull., 2001 Spring, vol. 35, Issue 2, pp. 5-49 (Abstract).
Merry, "Treatment of dry Age-related Macular Degeneration with Photobiomodulation", presented at ARVO, Fort Lauderdale, FL, May 7, 2012.
Minagawa-Kawai, "Prefrontal activation associated with social attachment: Facial-emotion recognition in mothers and infants", Cerebral Cortex, Feb. 2009, vol. 19, pp. 284-292 (Abstract).
Moch Izuki-Oda, "Effects of near-infra-red laser irradiation on adenosine diphosphate contents of rat brain tissue", Neurosci. Letters (2002), vol. 323, pp. 208-210.
Moses-Kolks, "Serotonin 1A receptor reductions in postpartum depression: a PET study", Fertil. Steril., Mar. 2008 vol. 89, Issue 3, pp. 685-692.
Naeser et al., "Significant Improvements in Cognitive Performance Post-Transcranial, Red/Near-Infrared Light-Emitting Diode Treatments in Chronic, Mild Traumatic Brain Injury: Open-Protocol Study", J. Neurotrauma 2014, vol. 31, Issue 11, pp. 1008-1017.
Neumeister, "Effects of tryptophan depletion on serum levels of brain-derived neurotrophic factor in unmedicated patients with remitted depression and healthy subjects", Am J Psychiatry, Apr. 2005, vol. 162, Issue 4, pp. 805-807, (Abstract).
Nitschke, "Orbitofrontal cortex tracks positive mood in mothers viewing picturesof their newborn infants", Neurolmaoe 21 (2004) 583-592 .
Noriuchi, "The Functional Neuroanatomy of Maternal Love: Mother's Response to Infant's Attachment Behaviors" Biol. Psychitary, Feb. 15, 2008, vol. 63, Issue 4, pp. 415-423, (Abstract).
Oron, "Ga-As (808 nm) Laser Irradiation Enhances ATP Production in Human Neuronal Cells in Culture", Photomed Laser Surg., Jun. 2007, vol. 25, Issue 3, pp. 180-182 (Abstract).
Ostrakhovich, "Active Form of Oxygen and Nitrogen in Blood Cells of Patients with Rheumatoid Arthritis: Effect of Laser Therapy", Vestn Ross Akad Med Nauk., 2001, vol. 5, pp. 23-27 (Abstract).
Ranote, "The neural basis of maternal responsiveness to infants: an fMRI study", Neuroreport, Aug. 6, 2004; vol. 15, Issue 11, pp. 1825-1829, (Abstract).
Rochkind, "Increase of neuronal sprouting and migration using 780 nm laser phototherapy as procedure for cell therapy", Lasers Surq. Med., 2009, vol. 41, pp. 277-281 (Abstract).
Roelofs, "On the neural control of social emotional behavior", SCAN (2009) vol. 4, pp. 50-58.
Romm, "Action of laser radiation on the peroxide chemiluminescence of wound exudate", Biull. Eksp. Biol. Med. Oct. 1986 vol. 102, Issue 10, pp. 426-428 (Abstract).
Salehpour et al.—"Brain Photobiomodulation Therapy: a Narrative Review", Molecular Neurobiol (2018) vol. 55, Issue 8, pp. 6601-6636, Published online Jan. 11, 2018, Springer Science-Business Media, LLC, part of Springer Nature 2018.
Schiffer, "Psychological benefits 2 and 4 weeks after a single treatment with near infrared light to the forehead: a pilot study of 10 patients with major depression and anxiety", Behavioral and Brain Function, Dec. 8, 2009, vol. 5:46, 13 pages.
Seifritz, "Differential sex-independent amygdala response to infant crying and laughing in parents versus nonparents", Biol. Psychiatry, 2003, vol. 54, pp. 1367-1375.
Tang, "Photobiomodulation in the treatment of patients with noncenter-involving diabetic macular oedema", Br. J. Ophthalmol., Aug. 2014, vol. 98, Issue 8, pp. 1013-1015.
Tedford, "Quantitative analysis of transcranial and intraparenchymal light penetration in human cadaver brain tissue", Lasers in Surgery and Medicine 2015, vol. 47, pp. 312-322. (Abstract).
Uozumi et al.—"Targeted Increase in Cerebral Blood Flow by Transcranial Near-Infrared Laser Irradiation", Lasers in Surgery and Medicine, vol. 42, Issue 6, Aug. 2010, pp. 566-576, Published by ResearchGate.
Vladimirov, "Photobiological Principles of Therapeutic Applications of Laser Radiation Biochemistry", 2004, vol. 69, Issue 1, pp. 81-90, Moscow.
Vladimirov, "Photoreactivation of Superoxide Dismutase by Intensive Red (Laser)Light", Free Rad. Biol. Med., 1988, vol. 5, Issues 5-6, pp. 281-286.
Volotovskaia, "Antioxidant action and therapeutic efficacy of laser irradiation of blood in patients with ischemic heart disease", Vopr Kurortol Zizioter Lech Fiz Kult May-Jun. 2003 vol. 3, pp. 22-25 (Abstract).
Wada, "Lithium: potential therapeutics against acute brain injuries and chronic neurodegenerative diseases", J Pharmacol Sci. Dec. 2005; vol. 99, Issue 4, pp. 307-321 (Abstract).
Wang, "Lithium Inhibition of Protein Kinase C Activation-Induces Serotonin Release", iPsychopharmacoloov (Berl). 1989 vol. 99, Issue 2, pp. 213-218 (Abstract).
Wollman, "In vitro cellular processes sprouting in cortex microexplants of adult rat brains induced by low power laser irradiation", Neurol. Res. Jul. 1998, vol. 20, Issue 5, pp. 470-472 (Abstract).
Wollman, "Low power laser irradiation enhances migration and neurite sprouting of cultured rat embryonal brain cells", Neurol. Res. Oct. 1996, vol. 18, Issue 5, pp. 467-470 (Abstract).
Wong-Riley, "Light-emitting Diode Treatment Reverses the Effect of TTX on Cytochrome Oxidase in Neurons", Neuroreport, 2001, vol. 12, Issue 14, pp. 3033-3037 [Abstract].
Wong-Riley, "Photobiomodulation Directly Benefits Primary Neurons Functionally Inactivated by Toxins", J Biol Chem., Feb. 11, 2005, vol. 280, Issue 6, pp. 4761-4771.
Yaroslavsky, "Optical properties of selected native and coagulated human brain tissues in vitro in the visible and near infrared spectral range", Biol., 2002, vol. 47, pp. 2059-2073.
Zhang, "Low-Power Laser Irradiation Inhibiting Aβ25-35—induced PC12 Cell Apoptosis via PKC Activiation" Cell Phvsiol Biochem., 2008, vol. 22, Issue 1-4, pp. 215-222.
U.S. Appl. No. 62/834,394, filed Apr. 15, 2019, Transorbital NIR Light Therapy Devices.
U.S. Appl. No. 62/844,855, filed May 8, 2019, Transorbital NIR Light Therapy Devices.
U.S. Appl. No. 62/859,971, filed Jun. 11, 2019, Transorbital NIR Light Therapy Devices.
U.S. Appl. No. 62/865,468, filed Jun. 24, 2019, Transorbital NIR Light Therapy Devices.
U.S. Appl. No. 62/871,889, filed Jul. 9, 2029, Transorbital NIR Light Therapy Devices.
U.S. Appl. No. 62/892,513, filed Aug. 27, 2019, Transorbital NIR Light Therapy Devices.
U.S. Appl. No. 62/902,182, filed Sep. 18, 2019, Transorbital NIR Light Therapy Devices.
U.S. Appl. No. 16/419,369, filed May 22, 2019, Transorbital NIR Light Therapy Devices.
International Searching Authority—International Search Report and Written Opinion for International Application No. PCT/IB2020/053510, dated Jul. 27, 2020 (20 pages).
U.S. Appl. No. 15/839,954, filed Dec. 13, 2017, Trans-Orbital Infrared Light Therapy.

(56) References Cited

OTHER PUBLICATIONS

[No Author Listed] Frontal Sinus Transillumination Video, 2010, https://www.youtube.com/watch? v=8Lo3bENDqzs.
Invitation to Pay Additional Fees for Application No. PCT/IB2020/053510, dated May 28, 2020 (15 pages).

* cited by examiner

OR

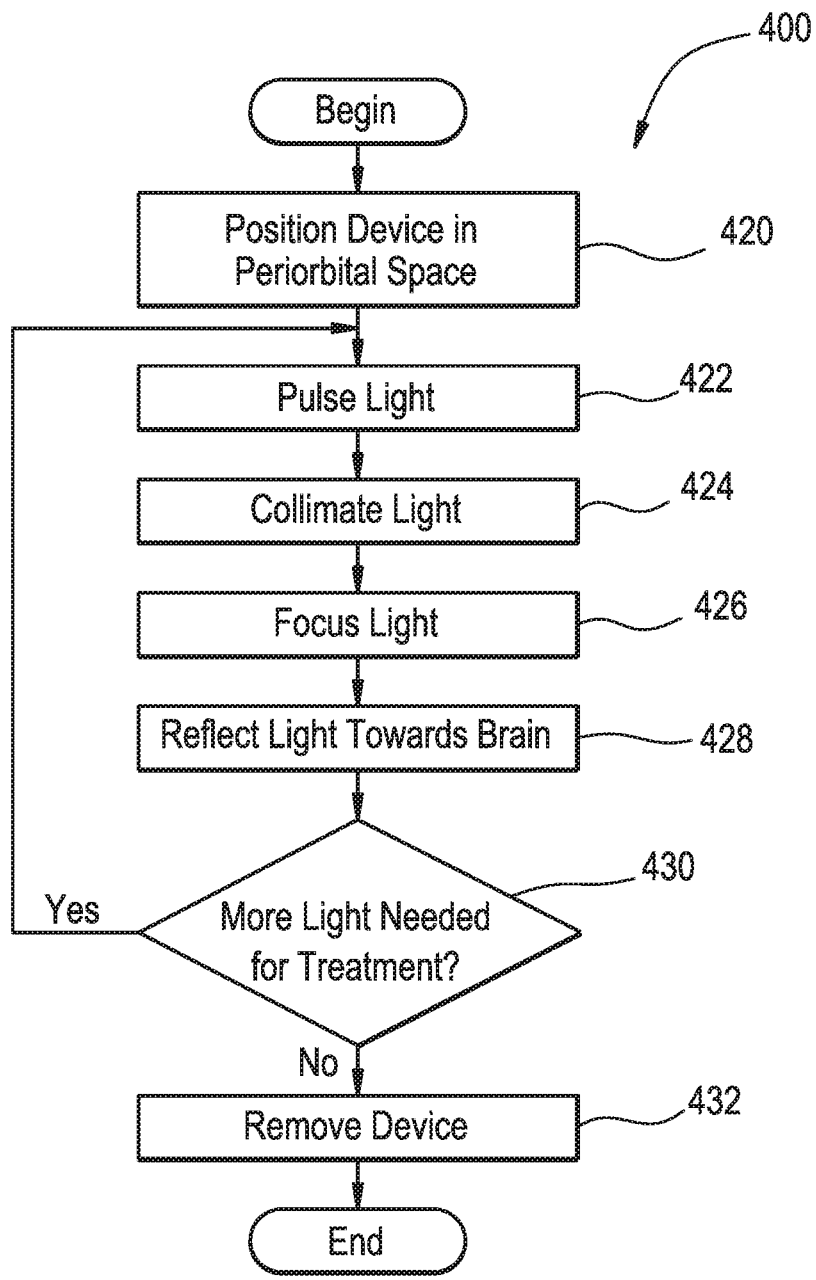

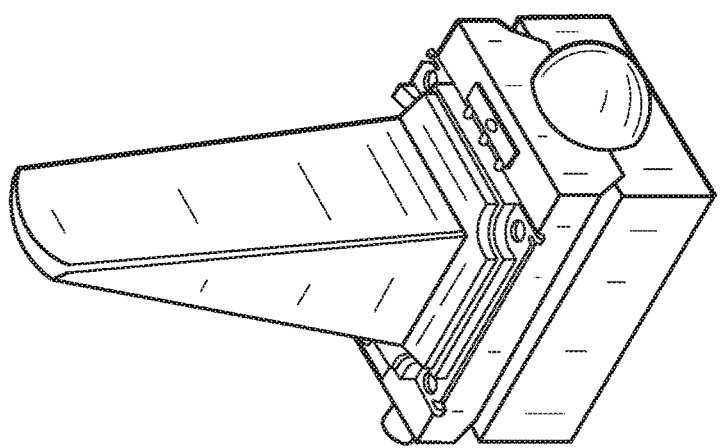
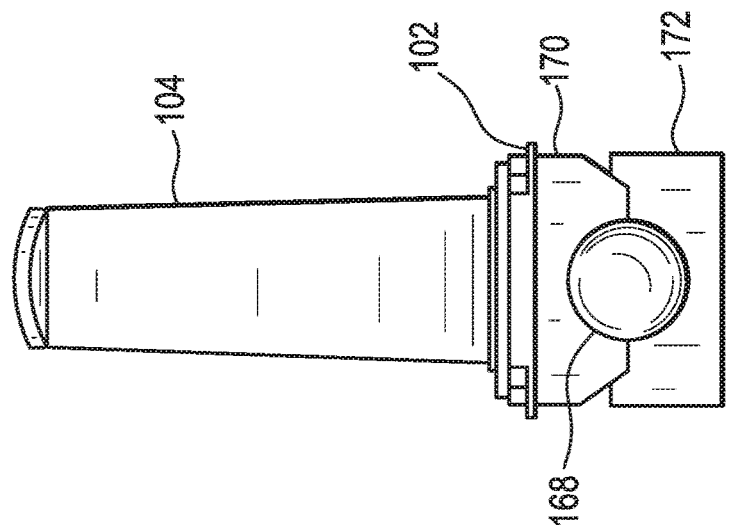
FIG. 43
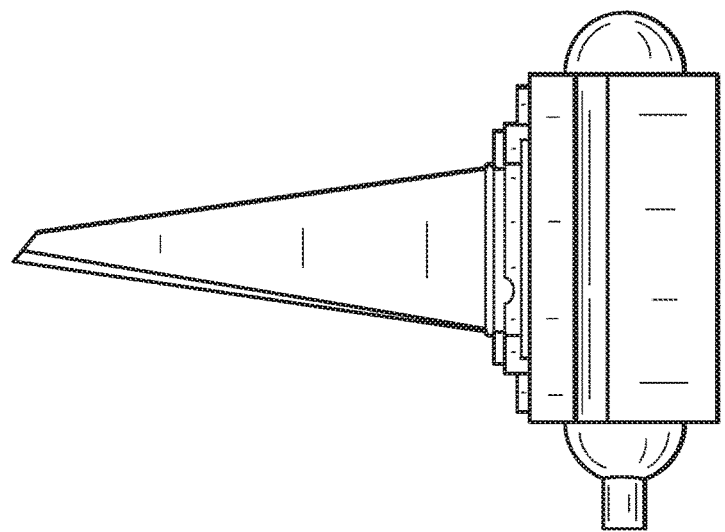

TRANSORBITAL NIR LIGHT THERAPY DEVICE

PRIORITY

This application claims priority to (a) U.S. Provisional Application No. 62/834,394, filed on Apr. 15, 2019, entitled "Transorbital NIR Light Therapy Devices," (b) U.S. Provisional Application No. 62/844,855, filed May 8, 2019, entitled "Transorbital NIR Light Therapy Devices," (c) U.S. Provisional Application No. 62/859,971, filed on Jun. 11, 2019, entitled "Transorbital NIR Light Therapy Devices," (d) U.S. Provisional Application No. 62/865,468, filed Jun. 24, 2019, entitled "Transorbital NIR Light Therapy Devices," (e) U.S. Provisional Application No. 62/871,889, filed Jul. 9, 2019, entitled "Transorbital NIR Light Therapy Devices," (f) U.S. Provisional Application No. 62/892,513, filed on Aug. 27, 2019, entitled "Transorbital NIR Light Therapy Devices," and (g) U.S. Provisional Application No. 62/902,182, filed Sep. 18, 2019, entitled "Transorbital NIR Light Therapy Devices," the disclosures all of which are incorporated herein, in their entireties, by reference.

This application is a continuation-in-part of U.S. patent application Ser. No. 16/419,369, filed May 22, 2019, entitled "Transorbital NIR Light Therapy Devices," the disclosure of which is incorporated herein, in its entirety, by reference.

FIELD OF THE INVENTION

Illustrative embodiments generally relate to near infrared (NIR) light and, more particularly, illustrative embodiments relate to devices for treating the brain using NIR light.

BACKGROUND OF THE INVENTION

Light therapy consists of exposure to daylight or specific wavelengths of light using a lighting device, such as an LED. The light is administrated for a prescribed amount of time and at a particular dosage. For example, US Published Patent Application 2014-0358199 (Lim) discloses the intranasal delivery of the infrared light to the orbitofrontal cortex of the brain. The commercial embodiment of this application appears to be the Vielight 810® device. The Vielight 810® device comprises an infrared LED that is positioned into the nose and is powered by a battery pack.

Red/NIR light is significantly attenuated as it penetrates tissue. According to one Lim white paper, red/NIR light suffers a power loss of about 80% per mm penetration of tissue. (Lim, The Potential Of Intranasal Light Therapy For Brain Stimulation, Feb. 2, 2013, page 8). In another white paper, Lim reports that a) only 2.4% of infrared light penetrates 3 cm of dead tissue, and b) in live rats, only about 6% of photons with a wavelength of between 630 nm and 800 nm penetrate tissues up to 28 mm. (Lim, Inventor's Notes on Whole Brain Photobiomodulation with Vielight Neuro—a Transcranial-Intranasal Light Therapy Combination, January 2016, pages 8 and 16).

The recommended treatment time for the Vielight Intranasal device is 25 minutes. (Lim, Potential supra, abstract.)

U.S. Pat. No. 8,734,498 (Codman I) discloses a hand-held intranasal light device comprising an infrared LED powered by a battery contained within the handle of the device.

The literature reports several articles involving NIR irradiation of the forehead, with subsequent monitoring of cerebral blood flow via functional NIR spectroscopy. See, e.g., Kroczek, Addiction Biology, "Prefrontal functional connectivity measured with near-infrared spectroscopy during smoking cue exposure", 2015. None of the FNIR articles reviewed report on neuronal activity in the OFC, thereby implying that NIR light did not reach the OFC from irradiation of the forehead. See. also, e.g., Leon-Carrion, "Functional Near-infrared Spectroscopy (fNIRS): Principles and Neuroscientific Applications" in Neuroimaging—Methods.

SUMMARY OF VARIOUS EMBODIMENTS

In accordance with one embodiment of the invention, a device for treating the brain includes a light source configured to emit near infrared light. The device also includes a collimator configured to receive the near infrared light emitted by the light emitter. The collimator is further configured to collimate the near infrared light. The device also includes an optic configured to focus collimated light. A reflector of the device is configured to change a direction of the collimated light. The reflector is at a distal end of the device, and the distal end is configured to fit between an upper portion of an eyelid of a patient and an orbital socket of the patient.

Among other things, the light source may be an LED or a laser. Some embodiments include a plurality of light sources. One or more of the light sources may emit near infrared light. Additionally, or alternatively, one or more of the light sources may emit red light. In some embodiments, the light source is configured to provide a dosage of light to the brain with an energy density of about around 1 $J/cm^2$.

In various embodiments, the optic is a cylindrical lens. However, in some other embodiments, the optic may be a spherical lens. The collimator may be, for example, a parabolic mirror, an ellipsoidal mirror, a total internal reflection optic, a Fresnel lens, and/or a convex lens. The device may further include a housing having the light source, the collimator, and the optic therein. However, the reflector may be outside of the housing.

In accordance with another embodiment, a device for treating the brain includes a light emitter configured to emit near infrared light. The device also has a light guide. The light guide has a proximal end configured to receive the near infrared light from the light emitter. The light guide also has a distal end through which the near infrared light exits the light guide. The distal end is configured to fit between an upper portion of an eyelid of a patient and an orbital socket of the patient. The light guide also has a material configured to cause total internal reflection of the near infrared light between the proximal end and the distal end. The device includes a reflective portion configured to change a direction of the near infrared light that exits the light guide.

In some embodiments, the light guide may be a solid light guide. For example, the light guide may formed from acrylic. The material configured to cause total internal reflection may be a coating. The coating may be on the acrylic material. In some embodiments, the coating is aluminum. Furthermore, the reflector may be an exposed internal surface of the material configured to cause the total internal reflection.

The device may include a thermo electric cooler, and/or a heat sink coupled with the light source. Additionally, the device may include a housing having the light emitter and the light guide therein. The housing may have an open distal end through which the light guide passes.

In accordance with yet another embodiment, a method treats the brain by providing a device having a light emitter configured to emit near infrared light in a first direction. The method also provides a reflector configured to change the direction of the light from a first direction to a second direction. The method positions at least a portion of the device in an orbital cavity of the patient, such that the second direction is toward an orbitofrontal cortex of the brain of the patient.

The method may further emit a therapeutic dose of near infrared light from the light emitter. Additionally, the method may reflect the emitted near infrared light transorbitally towards the orbitofrontal cortex of the patient. Positioning the device may include placing the reflector at least about 15 mm into the orbital socket from a surface of a frontal bone of the patient.

In some embodiments, the device further includes a collimator. The method may include actuating the LED so that the NIR light exits the LED and is substantially collimated in the collimator. The device may further include an optic configured to focus the light towards the reflector.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 42 shows a process of treating the brain in accordance with illustrative embodiments of the invention.

FIG. 43 schematically shows a thermal management system including liquid pressurized gas (LPG) cooling in accordance with illustrative embodiments of the invention.

DESCRIPTION OF ILLUSTRATIVE EMBODIMENTS

Figure 1:
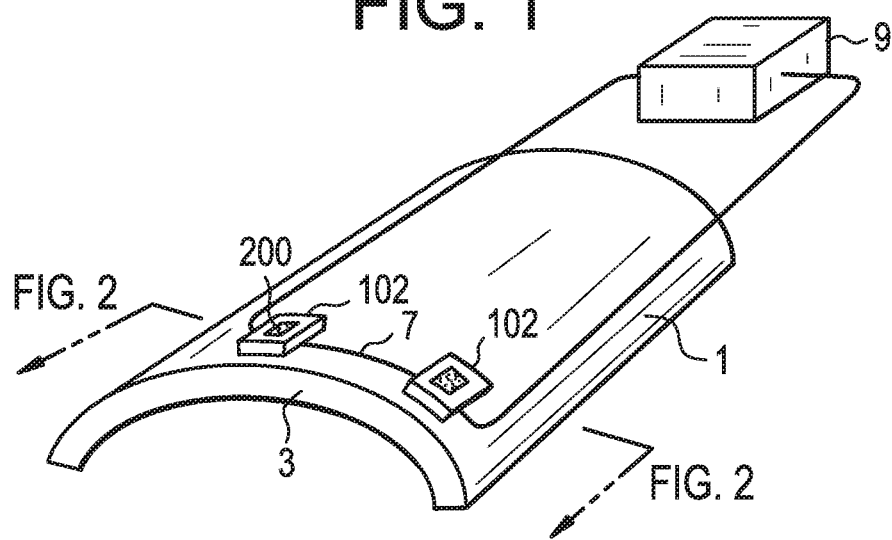
FIG. 1 schematically shows a perspective view of a device having a pair of light emitters attached to a curved based adapted for insertion into the eye socket in accordance with illustrative embodiments of the invention.

In illustrative embodiments, a device treats the brain by transorbital delivery of near-infrared light (NIR light). Illustrative embodiments position a reflector in the periorbital space (e.g., the space between the eyelid and the orbital bone) and direct the NIR light towards the reflector. The reflector is configured to change a direction of the NIR light emitted by the light source. Thus, the light source emits NIR light in a first direction, towards the reflector, which redirects the light in a second direction towards the frontal cortex of the patient. The reflector advantageously allows the NIR light to be transmitted to the brain transorbitally, which generally is unable to fit a light source therein. Additionally, a collimator and/or focusing optic may be used to increase the amount of light that reaches the brain. Details of illustrative embodiments are discussed below.

Without wishing to be bound by any particular theory, the inventors believe that the NIR light treats the brain by stimulating transmembrane proteins in the mitochondria of brain cells, thereby improving the proteins catalytic activity and elevating ATP synthesis. Generally, to provide the desired clinical outcome, a minimum effective dosage of light reaches the brain. However, illustrative embodiments also account for a maximum permissible NIR light exposure limit that exists for patient safety.

While illustrative embodiments refer to NIR light, other spectrums of light may also be used to treat the brain. For example, short infrared light having a wavelength of between about 1.4 micrometers and about 3 micrometers, and/or red light having a wavelength of between about 625 nanometers and about 740 nanometers, may also be used to treat the brain. Thus, the discussion of the light source (also referred to as the light emitter) is not necessarily limited to NIR light. For example, in some embodiments the light emitter may emit infrared light and/or red light. Some embodiments may treat the brain using a plurality of light emitters each emitting NIR light, infrared light, and/or red light. Furthermore, while various embodiments may refer to the light source as an LED, it should be understood that the light source may additionally, or alternatively, be a laser.

In some embodiments, the light source delivers NIR light transcranially. However, the thickness and density of the patient's skull tends to attenuate the effective dosage of NIR light that reaches the brain. Accordingly, illustrative embodiments generally compensate for the attenuation by increasing the output intensity of the light source. The increased intensity may cause heat to build up at or around the eye, potentially causing patient discomfort and damaging tissue.

In some embodiments, the NIR light source 102 may be implanted in the brain (i.e., intracranial delivery). However, the invasive nature of the implanted light source 102 is not preferred from the patient's perspective. Additionally, the implanted light source 102 has a number of associated risks (e.g., infection, collateral damage from surgical procedure) and costs (e.g., anesthesia and/or medical professionals).

Some embodiments may provide intranasal transmission of NIR light. In some embodiments, the light source 102 may be inserted at a shallow depth in the nasal cavity. The bones and soft tissue between the nasal cavity and the brain result in large amounts of attenuation. Additionally, transnasal NIR light delivery may be unreliably attenuated by large increases in mucous (e.g., when the patient is sick) making precise delivery of effective light to the brain uncertain. Some embodiments insert the light source 102 deeper into the nasal cavity. However, depending on the insertion depth of the NIR light emitter 102 into the nasal cavity, the procedure may be too invasive for patient comfort. For example, mid-nose insertion depths may cause patient discomfort, require delivery by specialized operators, and are associated with risk of nose bleeds. F Some other embodiments may stimulate the brain by positioning the light source 102 in the oral cavity. For example, the emitter may be positioned into the back of the patient's throat. NIR light delivery through the oral cavity provides access to certain parts of the brain (e.g., the brain stem), but similarly suffers from attenuation losses described previously when stimulating other parts of the brain (e.g., the orbito-frontal cortex).

The inventors discovered that NIR light can be efficiently and reliably transmitted to the frontal lobe of the brain (e.g., the orbito-frontal cortex) by transorbital transmission. Transorbital transmission provides a number of advantages, including non-invasive access to the frontal lobe of the brain, and/or reduced attenuation through the orbital bone relative to transcranial, transnasal, and/or oral methods. However, the periorbital space around the eye generally cannot safely fit a light source therein. Furthermore, an unshielded light source inserted in the periorbital space could potentially burn the tissue and/or the eye of the patient. Accordingly, illustrative embodiments use direct light from the light source towards a reflector position in the periorbital space, which in turn redirects the light towards the brain transorbitally.

FIG. 1 schematically shows a light delivery device comprising:
  a) a base 1 comprising a substantially concavo-convex distal end portion 3, wherein the substantially concavo-convex distal end portion comprises a metallic composition,
  b) a plurality of light emitters 102 attached to the convex side 7 of the substantially concavo-convex distal end portion, wherein the light emitter oriented so that a majority of the light emitted by its LED faces away from the substantially concavo-convex distal end portion,
  c) a power source 9 in electrical connection with the plurality of light emitters.

Illustrative embodiments provide a number of advantages as discussed further below.

Figure 2:
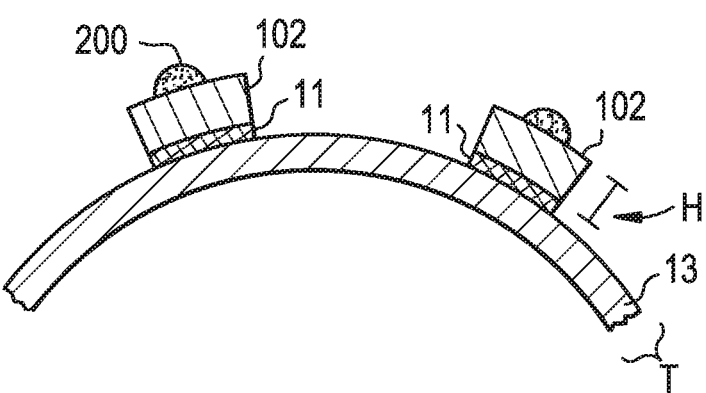
FIG. 2 schematically shows a cross section of FIG. 1.

First, the metallic nature of the substantially concavo-convex distal end portion provides for heat dissipation, thereby drawing heat the powered light emitters and reducing the temperature at the eyelid. FIG. 2 schematically shows light emitters 102 that are attached to a section of aluminum pipe 13 (via a section of very thin, double-sided thermally conductive tape 11 or a metallic paste or braze) and then may be powered by a 3 Volt battery.

Second, the light emitter is separated from the eyelid by a non-translucent concavo-convex distal end portion of the base. Thus, any light that is emitted by the light emitter towards the brain but then diffracted by tissue back towards the eye will be blocked by the metallic component. This provides a second measure of safety, thereby allowing for higher light fluxes to be used.

Figure 3:
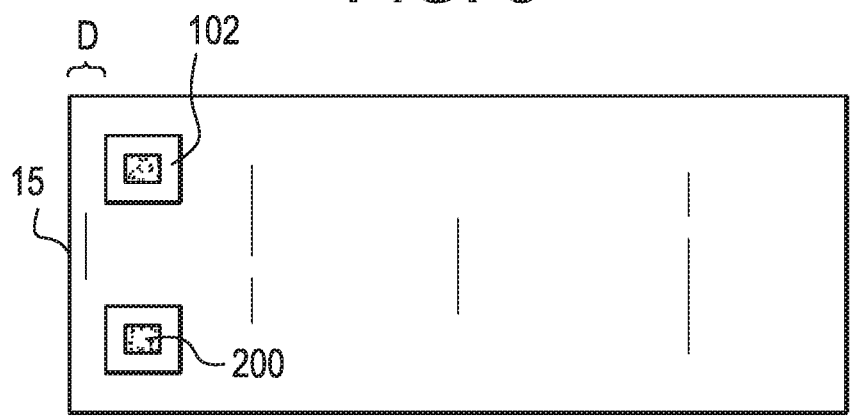
FIG. 3 schematically shows an elevation view of a portion of a device, showing the light emitters set back from the distal edge of the base in accordance with illustrative embodiments of the invention.

In some embodiments, and now referring to FIG. 3, the light emitters are situated at a distance D of least 3 mm (preferably at least 5 mm) from the distal end 15 of the concavo-convex portion. In this condition, light travels over that spacing before reaching the eye, and so that spacing acts as a block of NIR light reaching the eye.

Preferably the substantially concave distal end portion forms an arc of at least about 90 degrees, more preferably at least about 120 degrees, so that light emitter situated at the medial extreme can reach medial OFC structures like the gyrus rectus.

The inventors discovered that inserting a substantially concavo-convex element into the region between the eyelid and eye socket was fairly benign when the thickness of the element was about 1.5 mm, but became uncomfortable when the thickness of the element was about 6 mm. Thus, and now referring back to FIG. 2, preferably, the substantially concavo-convex distal end portion has a thickness T of less than 5 mm, preferably less than 3 mm, more preferably less than 2 mm. In a similar manner, the light emitters that are disposed on this element should be as short as possible to accommodate the comfort concern. Preferably, such an light emitter has a height H of less than 2 mm, preferably less than 1 mm. In some embodiments, the thin light emitter is the Luxeon Saber Micro-Z1 850 nm light emitter, available from Quadica Developments Inc at luxeonstar.com, Lethbridge, Alberta, Canada, which has a height of about 1 mm and has an irradiance rated at about 1050 mwatts.

Figure 4:
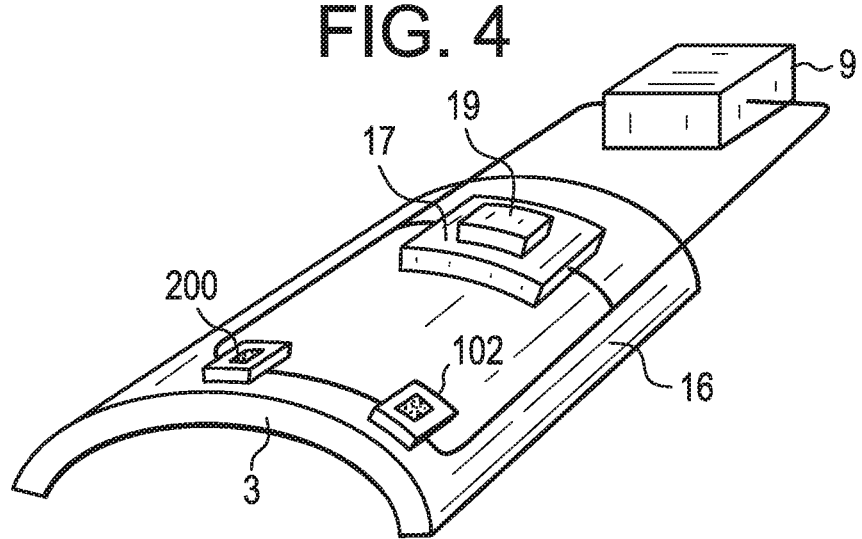
FIG. 4 schematically shows a perspective view of a device having a thermoelectric cooling unit disposed at a first location in accordance with illustrative embodiments of the invention.
Figure 5:
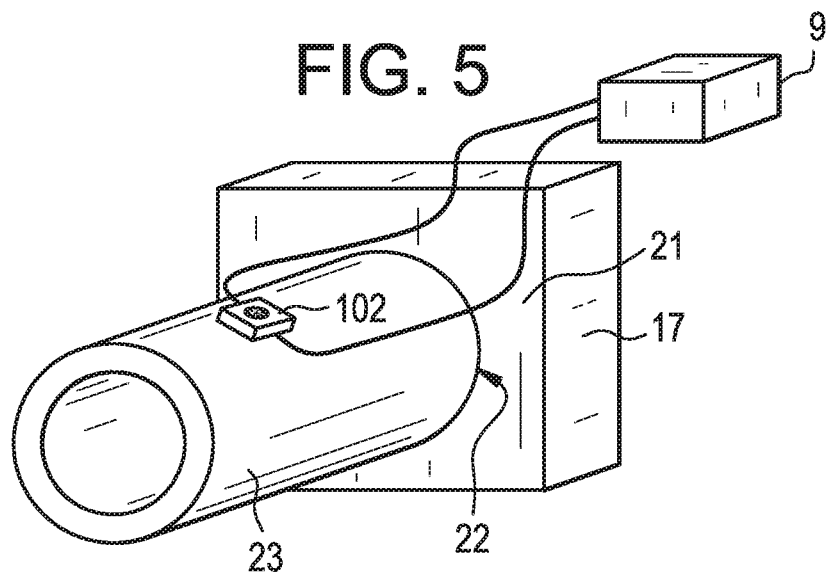
FIG. 5 schematically shows a perspective view of a device having a thermoelectric cooling unit disposed at a second location in accordance with illustrative embodiments of the invention.

FIG. 4 schematically shows an illustrative embodiment having a metallic base that has a proximal portion 16 that carries a thermoelectric cooler 17. The cold side of the thermoelectric cooler is put in contact with the proximal portion of the base and thereby cools the base when actuated, thereby lessening overheating concerns. In some embodiments, the thermoelectric cooler is attached to the proximal portion of the base by double sided thermally conductive tape, a braze or a metallic paste. In some embodiments, the proximal portion of the base is substantially flattened to accommodate the flat nature of the conventional thermoelectric cooler. Typically, a heat sink 19 and/or fan is attached to the hot side of the thermoelectric cooler. In some other embodiments, as in FIG. 5, the flat cold face 21 of the thermoelectric cooler 17 abuts the annular proximal end face 22 of a tubular base 23.

Figure 6:
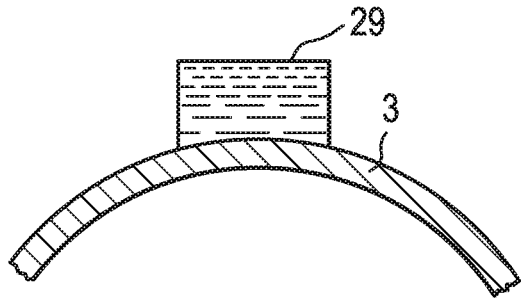
FIG. 6 schematically shows a cross section of a device in which ice is placed on the base as a cooling source in accordance with illustrative embodiments of the invention.
Figure 7:
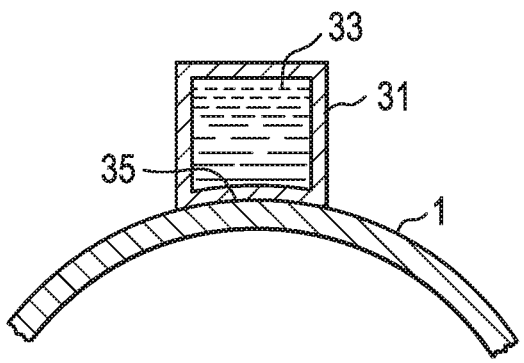
FIG. 7 schematically shows a cross-section of a device in which a thermally conductive container including a cooling element that is placed on the base as a cooling source in accordance with illustrative embodiments of the invention.

FIG. 6 schematically shows that ice 29 may be placed on the base as a cooling source in accordance with illustrative embodiments. In other embodiments, such as shown in FIG. 7, a thermally conductive container 31 containing a cooling element 33 is placed on the base 1 as a cooling source. Preferably, the thermally conductive container comprises a metal skin. Preferably, the cooling element is either ice or a chilled hydrogel. Preferably, the hydrogel comprises sodium polyacrylate. The thermally conductive container is placed in a refrigerator before use to cool the cooling element, and is taken out of the refrigerator just prior to use. When the container is placed on the base when the light emitter is energized, the cooling element functions to cool the metallic base during use, thereby reducing the temperature of the light emitter through conductive cooling.

Figure 8:
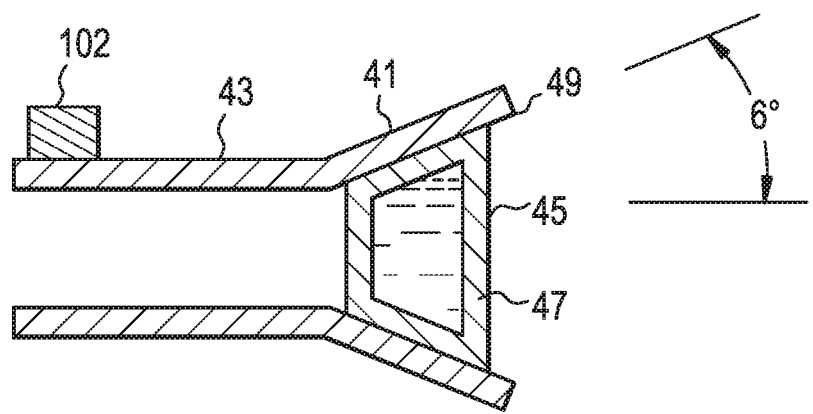
FIG. 8 schematically shows a cross-section of a device in which a thermally conductive container including a cooling element forms a Morse taper lock with the base in accordance with illustrative embodiments of the invention.

FIG. 8 schematically shows an embodiment having a proximal portion 41 of the base 43 in the form of a tube having a 6 degree conical taper expanding proximally, and the container 45 is a frustocone having a matching 6 degree taper expanding proximally, so that they form a Morse taper lock when the container is positioned into the proximal end 49 of the tube. Preferably, the proximal end 47 of the container is recessed below the surface of the proximal end 49 of the tube when the Morse taper lock occurs, thereby preventing its removal. Preferably, a bottom surface 35 of the container 31 has a concave curvature that matches the convex outer curvature of the base 1.

Figure 9:
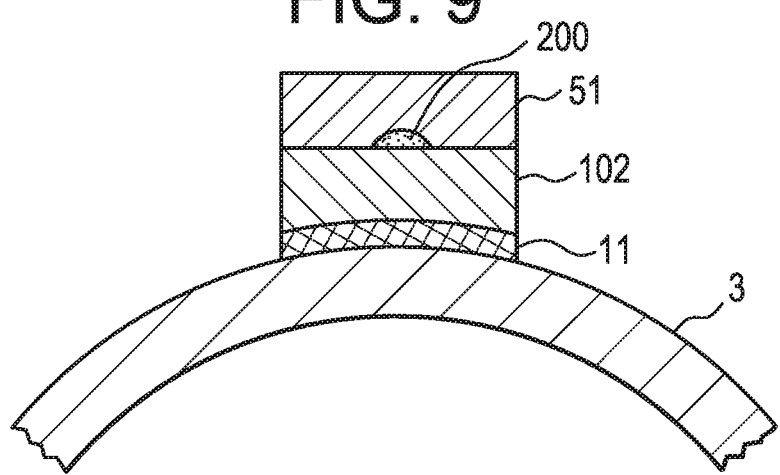
FIG. 9 schematically shows a cross section of a device in which an optically transparent thermal insulator is placed atop the NIR LED of the light emitter in accordance with illustrative embodiments of the invention.

Referring to FIG. 9, the light emitter 102 is attached the convex side of the substantially concavo-convex distal end portion by an interlayer comprising double-sided thermally conductive tape 11, or a braze or metallic paste. Preferably, the tape is also electrically resistive.

In some embodiments, the base can be a substantially tubular component adapted to fit between the eye and the eye socket. Typically, it has a diameter of between 25 and 35 mm. In other embodiments, the base is a portion of tube, typically extending in an arc of at least 90 degrees, preferably at least 120 degrees. Preferably it is made of a metallic material such as aluminum in order to effectively dissipate heat.

The power source 9 can be at least one or a plurality of batteries whose combined voltage output is adequate to drive the plurality of light emitters. The plurality of light emitters are put in electrical connection with the plurality of batteries. Typically, the power source 9 includes conventional electronics such as an on-off switch, a timer, and a constant-current element.

Now referring to FIG. 9, in some embodiments, the light emitter 102 is oriented so that a majority of the light emitted by the light emitter faces away from the substantially concavo-convex distal end portion, an optically translucent (preferably substantially optically transparent) thermal insulator 51 is placed over the LED of the light emitter. This insulator has the effect of reducing the heat flux to the eyelid generated by the LED while substantially preserving light transmission from the LED. Preferably the optically translucent thermal insulator comprises a polymer, such as acrylic or polyethylene. More preferably, the polymer is in the form of a foam. The voids in the foam enhance the thermal insulating qualities of the polymer, thereby making it a more effective thermal insulator. In some embodiments, the insulator has a thermal conductivity of no more than 0.030 W/M K, preferably no more than 0.025 W/M K, no more than 0.020 W/M K, no more than 0.015 W/M K. In some embodiments, the translucent thermal insulator is an aerogel, preferably a substantially optically transparent aerogel. In some embodiments in which the thermal insulator is a foam, a transverse hole is provided in the center of the foam to allow light an unobstructed path from the LED to the skin. The thickness of the insulator having the hole is sufficiently thick such that the LED does not contact the skin through the hole in use. In some embodiments in which the translucent thermal insulator is a substantially optically transparent aerogel, there is no transverse hole through the insulator. In some embodiments, the light emitter is attached to a heat pipe by a thermally conductive tape and is oriented so that a majority of the light emitted by the LED faces away from the heat pipe, and an optically translucent (preferably substantially optically transparent) thermal insulator 51 is placed over the LED.

Figure 10A:
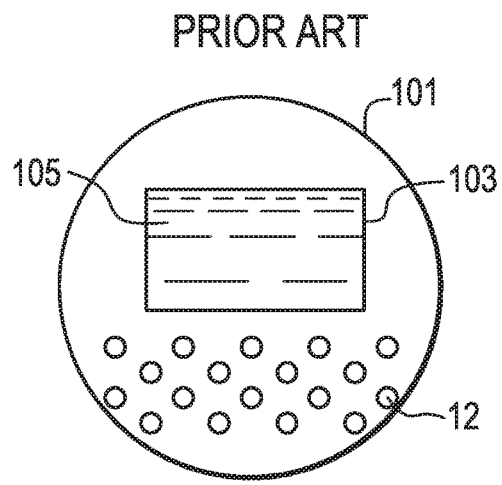
FIG. 10A schematically shows a cross-section of a conventional freeze pack bag including water and an endothermic solute.

In some embodiments, the power source intermittent provides energy to the LEDs. In some embodiments, the power source comprises an alternating current (AC). In others, the power source comprises a direct current (DC) modified to resemble a square wave with a duty cycle between about 10% and 90%. Preferably the duty cycle is between 25% and 75%. In each of these cases, it is believed that the intermittent energy delivery gives the light emitter time to dissipate heat buildup, thereby lowering the maximum temperature at the light emitter. See Bozkurt, *Biomedical Engineering Online,* 2004, 3, 9. Now referring to FIG. 10A, in some embodiments, cooling is achieved by application of instant ice pack technology, in which a large outer bag 101 contains a smaller bag 103 of water 105 and an endothermic reactant 12 that cools when mixed with water, often to temperatures at or below 0° C. In some embodiments, the endothermic reactant is ammonium nitrate while in others it is urea. In some embodiments, the large outer bag is placed in contact with the base and then squeezed to rupture the water-containing inner bag. The resulting endothermic reaction between the water and endothermic reactant cools the bag and the base with which it is in contact. The cooled base should also cool the light emitter.

Figure 10B:
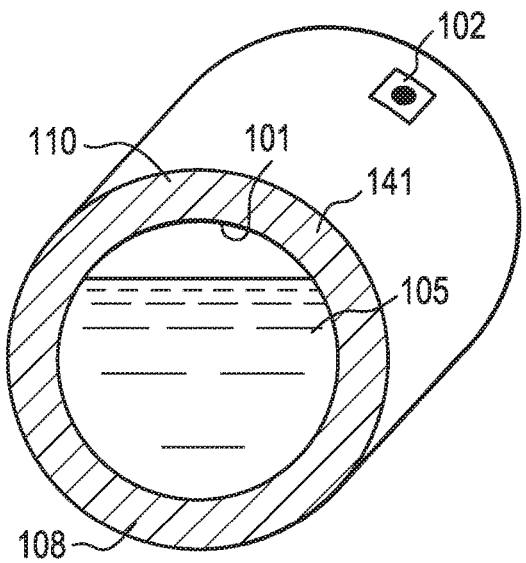
FIG. 10B schematically shows a cross-section of a device including a cooling element within the tube that forms the base in accordance with illustrative embodiments of the invention.

Now referring to FIG. 10B, if the outer bag 101 is placed within the tube 109 after the smaller bag is ruptured, however, the liquid water 105 will seek its lowest resting place and contact only the lowest portion 108 of the tube and not the uppermost portion 110 of the tube where the light emitter 102 resides. This is problematic because the coolant is far away from the light emitter.

Figure 10C:
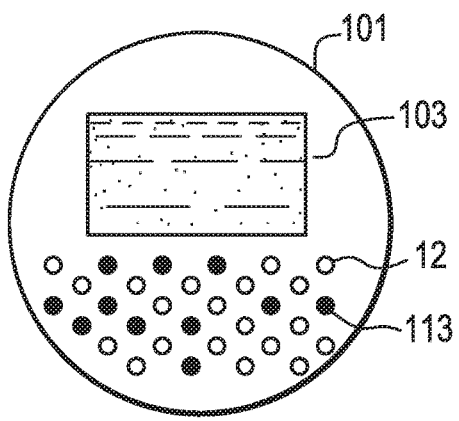
FIG. 10C schematically shows a cross-section of a freeze pack bag including water, an endothermic solute and a gelling agent in accordance with illustrative embodiments of the invention.
Figure 10D:
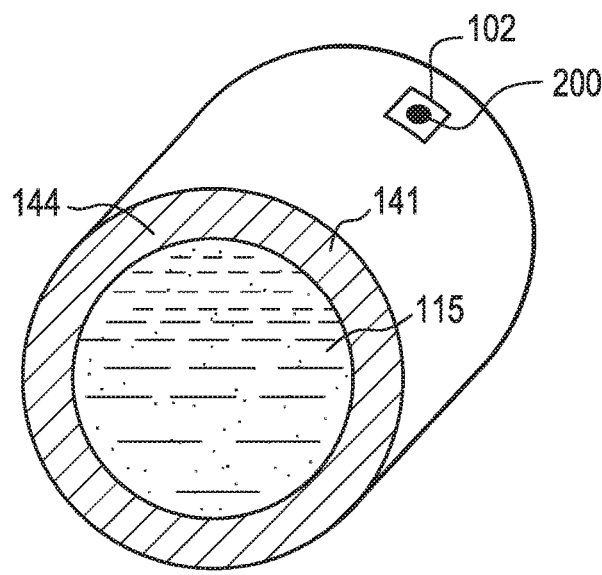
FIG. 10D schematically shows a cross section of the device in which the cooling element is a gel in accordance with illustrative embodiments of the invention.

Thus, in some embodiments, and now referring to FIGS. 10C and 10D, the outer bag 101 has a cylindrical shape, the base 109 has a tubular shape, and the outer bag is sized to fit within the tube, wherein the outer bag also contains a gelling agent 113 such as sodium polyacrylate, which gels and expands upon contact with water. Upon squeezing, the gelation and expansion of the sodium polyacrylate acts to completely fill the outer bag with gel 115 such that the entire perimeter of the cylindrical outer bag mates with the inner diameter of the tubular base, thereby providing an intimate cooling surface about its periphery, including the upper region 110 of the tube where the light emitter 102 is located.

Figure 10E:
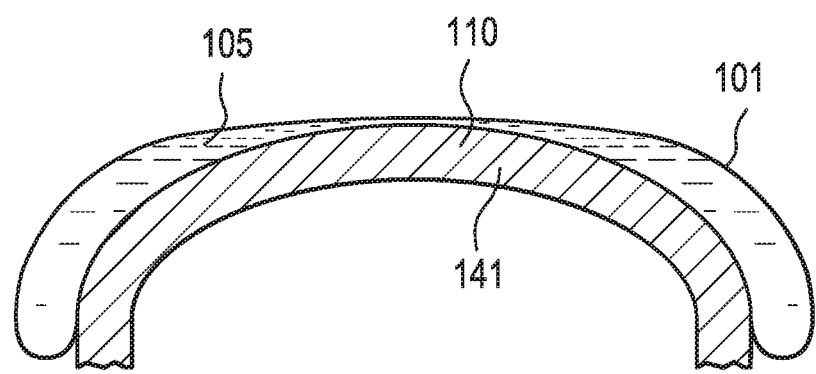
FIG. 10E schematically shows a cross-section of the device in which the coolant agent is in the liquid state in accordance with illustrative embodiments of the invention.
Figure 10F:
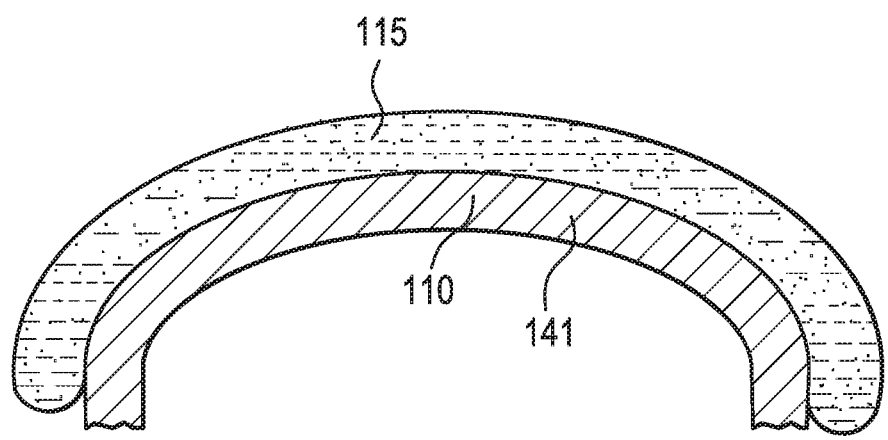
FIG. 10F schematically shows a cross-section of the device in which the coolant agent is in the gelled state in accordance with illustrative embodiments of the invention.
Figure 11A:
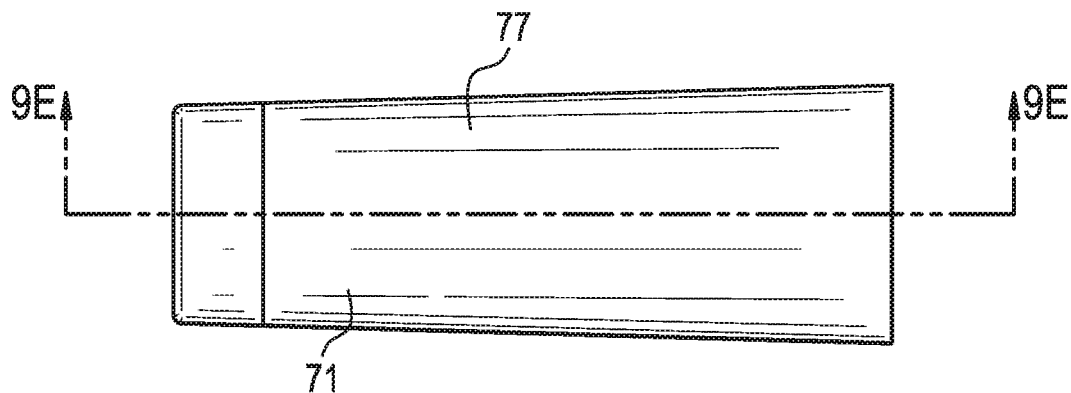
FIGS. 11A-G schematically show various views of a light in accordance with illustrative embodiments of the invention.
Figure 11B:
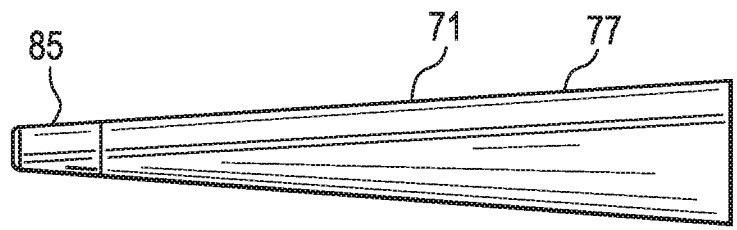
Figure 11C:
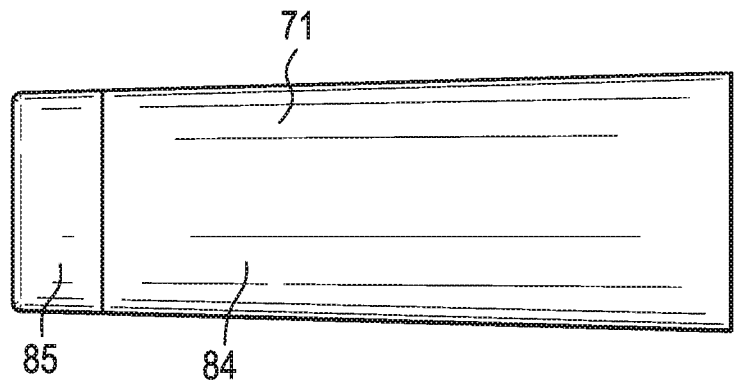
Figure 11D:
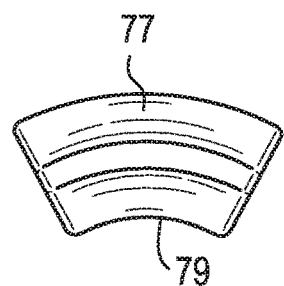
Figure 11E:
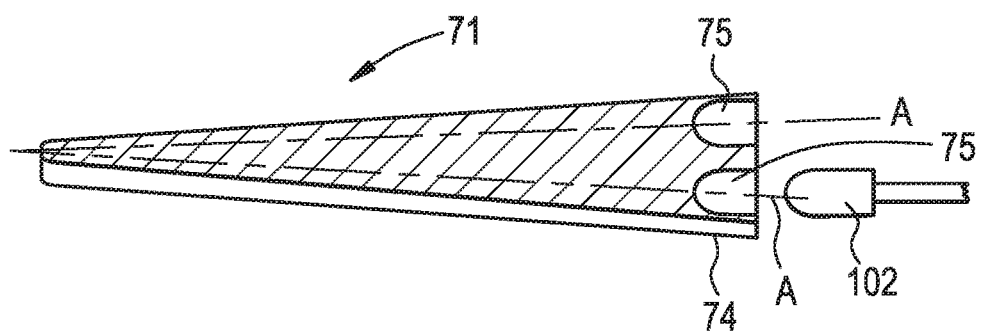
Figure 11F:
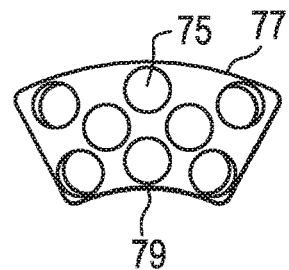
Figure 11G:
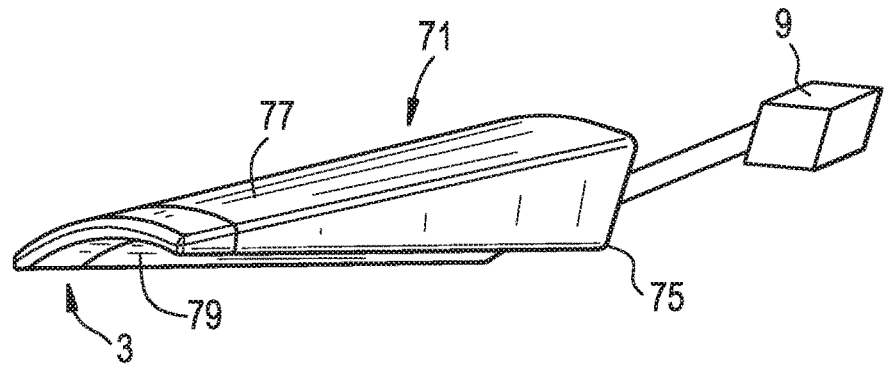

In some embodiments, and now referring to FIG. 10E, if the outer bag contains only water and the endothermal coolant but not the sodium polyacrylate and that outer bag is placed upon the tube 109 (instead of in the tube), the liquid water 105 in the bag seeks the lowest resting place and contact only the lowest portion of the bag and not the uppermost portion 110 of the tube where the light emitter resides. Thus, in some embodiments, as in FIG. 10F, the outer bag is substantially flat and is placed upon the upper surface of the base. Again, the outer bag also contains a gelling agent such as sodium polyacrylate, which gels upon contact with water, and the gel 115 expands. The expansion of the sodium polyacrylate acts to completely fill the outer bag such that substantially all of the upper surface of the base has the coolant mixture directly above it. The provides for closer approach of the coolant to the light emitter that resides at the apex of the tube.

When the LED of the light emitter is situated proximate the eyelid, there is a concern with resistive heating from the p-n junction of the LED causing overheating of the eyelid skin. Thus, in some embodiments, the light emitter is moved proximally off the eyelid and a light pipe is interposed between the light emitter and the eyelid, wherein the light pipe carries light from the LED to the eyelid. Thus, any heating caused by the LED is carried out a safe distance away from the eyelid.

In some embodiments, and now referring to FIGS. 11A to 11G, schematically shown is a light delivery device comprising:
a) a light guide, such as light pipe 71, comprising i) a substantially concavo-convex distal end portion 3 adapted to be positioned in a region between the eye and the eye socket, and ii) a proximal end portion 74 having at least one recess 75 adapted to receive at least one light emitter (preferably a plurality of light emitters); iii) an upper surface 77 and iv) a lower surface 79, wherein the concave portion thereof is displayed on the lower surface and the convex portion thereof is displayed on the upper surface;
b) at least one light emitter 81 received in the proximal end portion of the light pipe, the light emitters oriented to shine in the distal (posterior) direction;
c) a power source 9 (preferably at least one battery) electrically connected to the at least one light emitter;
d) a metallic coating 84 covering the outer surface of the light pipe, and
e) a light window 85 defined by an absence of metallic coating upon an upper surface of the a substantially concavo-convex distal end portion a substantially concavo-convex distal end portion.

Thus, preferably, the substantially concavo-convex distal end has a thickness of less than 5 mm, preferably less than 3 mm, more preferably less than 2 mm. These relatively thin sections allow for fairly comfortable distal (posterior) insertion of the element into the region between the eye and the eye socket to a distance of at least 10 mm, preferably at least 15 mm, more preferably at least 20 mm. Likewise, the substantially concavo-convex distal end section preferably has a thickness of less than 5 mm (preferably less than 3 mm) at a distance about 20 mm from the distal end, thereby keeping relatively thin the substantial majority of the light pipe that enters the eye socket.

Preferably, the light emitters are situated at least 30 mm, at least 50 mm or at least 70 mm away from the distal end of the light pipe. In this condition, any heat they generate will not affect the eyelid.

In some embodiments, the proximal end portion of the light pipe comprises recesses 75 adapted to receive light emitters. In some embodiments, the recesses are shaped as substantial cylinders in order to accommodate the conventional substantially cylindrical light emitter. In some embodiments, the recesses are shaped as substantial hemispheres in order to accommodate the conventional substantially hemispherical light emitter. In some embodiments, the light emitter recesses (and hence the light emitters themselves) are each defined by an axis that substantially intersects the distal wall of the substantially concavo-convex distal end portion, thereby pointing the light emitters substantially at the window. In some embodiments, the light emitter recesses are each defined by an axis A that substantially intersects the window, thereby pointing the light emitters directly at the window. In some embodiments, recesses that are on the upper surface are pointed at the lower surface at an angle that allows for the single reflection of light off the lower surface and into the window on the opposite upper surface. Likewise, in some embodiments comprising a linear array of light emitters spanning the medial-lateral aspect of the eye, the axes of the light emitter recesses (and hence the light emitters themselves) all substantially point directed forward so that there is a substantially equal distribution of light in the medial-lateral span.

Preferably the window 85 is situated at least 3 mm from the proximal end of the substantially concavo-convex distal end portion, thereby preventing a straight light path from the device to the eye. In some embodiments, the upper and lower surfaces of the light pipe are polished in order to better reflect incident light.

In some embodiments, the light emitters are selected to be the Vishay VSLY 5850 850 nm light emitter, which are advertised to have a very narrow emission beam (appearing to be around 10 degrees). This light saber nature of this light emitter allows targeting of the window and thus a large portion of the light emitted by these light emitters to travel directly to the window area without having been continually reflected off an upper or lower surface. Thus, in some embodiments, a majority of the light emitted by the light emitter is emitted in a 10 degree cone. In other embodiments, a majority of the light emitted by the light emitter is emitted in a 20 degree cone.

In other embodiments, the light emitters associated with the light pipe are 50 W or 10 W light emitters having an array of 850 nm LEDs, and are available, for example, from Hontiey at hontieychina.aliexpress.com In some embodiments, the light pipe is made of a substantially unitary piece of substantially NIR-transparent plastic, such as an acrylic. Typically, the unitary piece is solid. In some embodiments, however, the light pipe can be hollow with reflective material on the inside surface thereof. In some of these embodiments, the light pipe can be a hollow unitary piece of metal, or a hollow unitary piece of one material (such as plastic) whose inner surface is coated by a reflective surface (such as a metallic coating).

In some embodiments, the distal wall of the light pipe is coated with a metallic material. When this feature is combined with a window that only starts 3-5 mm inward of the distal wall, there is a measure of safety in that light emanating from the window does not have a direct path to the eye, but rather takes a more circuitous route and thereby become subject to the severe attenuation afforded by transmission through tissue.

In other embodiments, the distal wall of the light pipe is uncoated and the window on the upper surface extends to the distal wall. In this condition, the light emanating from the light emitters is afforded an unobstructed path through the distal portion of the light pipe towards the orbitofrontal cortex.

In some embodiments, the light emitters and power source of the embodiment above (elements b and c) are provided in the form of a flashlight, and the light pipe can be considered as an adapter.

In some embodiments, heat pipes are used to transport heat away from the operating light emitters. Heat pipes are generally hollow tubes containing a fully enclosed evaporative fluid that evaporates near a heat source at a first end of the tube, is transported away from the heat source and rejects heat upon condensation at the opposite end of the tube. The cooled liquid is then transported back to the heat source end of the tube by wicking. Heat pipes are typically used in order to provide cooling to an environment.

Figure 12:
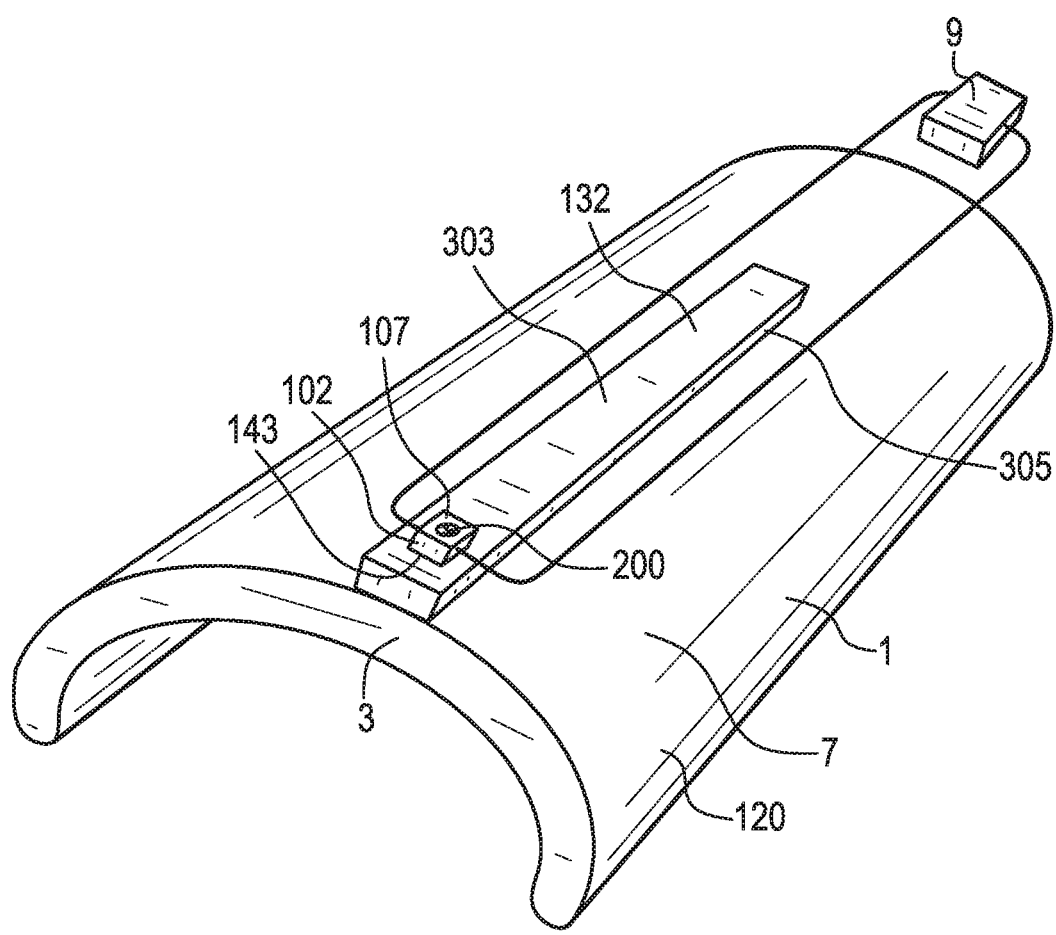
FIG. 12 schematically shows a perspective view of a device including a heat pipe in accordance with illustrative embodiments of the invention.

In some embodiments, and now referring to FIG. 12, schematically shown is a light delivery device comprising:
  a) a base 1 comprising a substantially concavo-convex distal end portion 3,
  b) a light emitter 102 having a first light emitting face 107 and a second opposite face 109, and an NIR LED 200 on the first light emitting face,
  c) a heat pipe 132 having a first side 305 attached to the convex side 7 of the substantially concavo-convex distal end portion and a second side 303 attached to the second face of the light emitter,
  d) a power source 9 in electrical connection with the light emitter, wherein the light emitter is located in the distalmost quarter 120 of the base.

Figure 13:
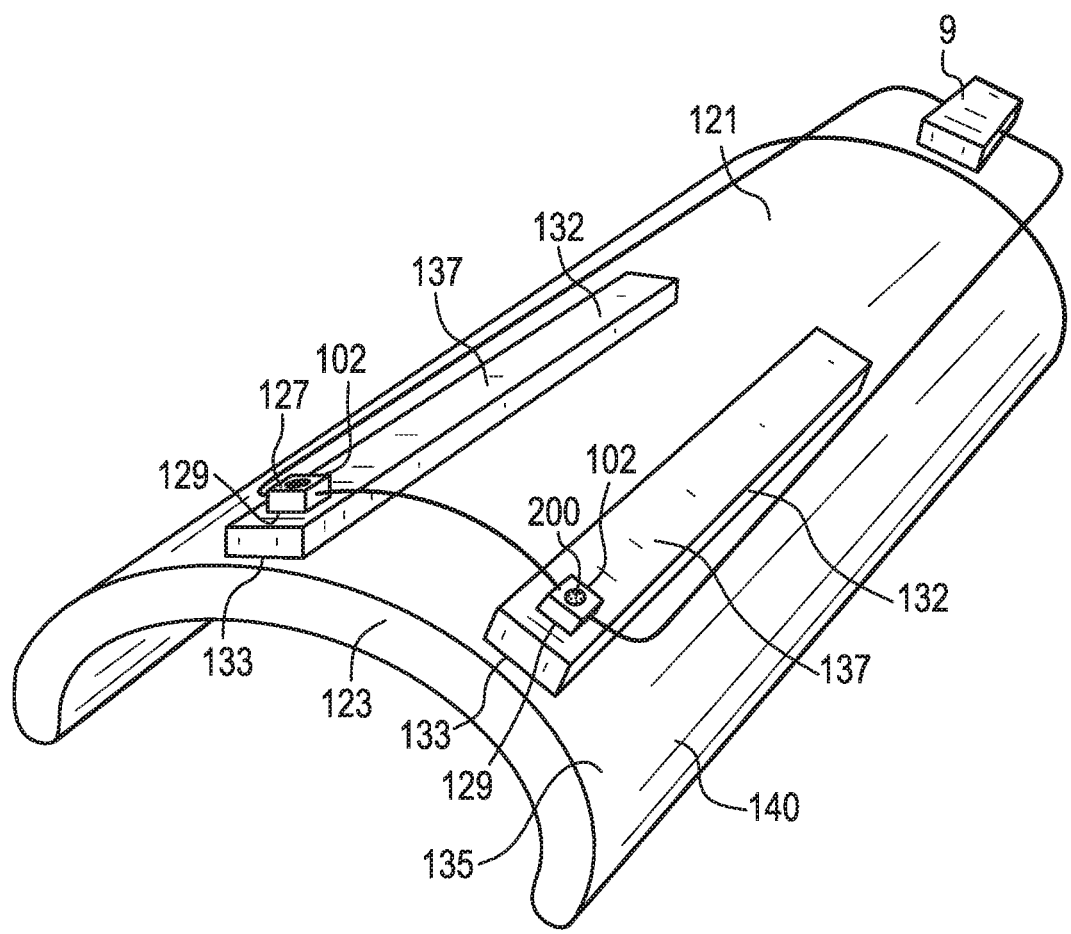
FIG. 13 schematically shows a perspective view of a device including a plurality of heat pipes in accordance with illustrative embodiments of the invention.

In some embodiments, and now referring to FIG. 13, schematically shown is a light delivery device comprising:
  e) a base 121 comprising a substantially concavo-convex distal end portion 123,
  f) a plurality of light emitters 102, each light emitter having a first light emitting face 127 and a second opposite face 129,
  g) a plurality of heat pipes 132, each heat pipe having a first side 133 attached to the convex side 135 of the substantially concavo-convex distal end portion and a second opposite side 137 attached to the respective second faces of the plurality of light emitters,
  h) a power source 9 in electrical connection with the plurality of light emitters.
wherein the light emitters are located in the distalmost quarter 140 of the base.

Figure 14:
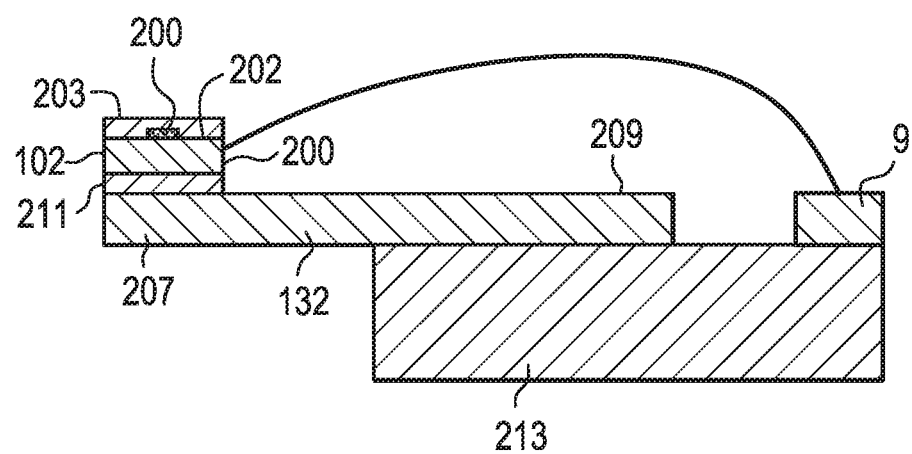
FIG. 14 schematically shows a cross-section of a device including an insulator, a heat pipe and a cooling element in accordance with illustrative embodiments of the invention.

In some embodiments, and now referring to FIG. 14, the NIR light emitting device of illustrative embodiments of the invention comprises:
  a) an NIR light emitter 102 having a lower side 200, an upper side 202, and an NIR LED 200 on the upper side, wherein NIR light is emitted only from the upper side,
  b) a substantially NIR-transparent insulator 203 (such as an optically transparent aerogel),
  c) a heat pipe 132 having a distal end portion 207 and a proximal end portion 209,
  d) a cooling element 213, and
  e) a power source 9,
  wherein the distal end portion of the heat pipe is attached to the lower side of the NIR light emitter (preferably, by double sided, thermally conductive adhesive tape 211),
  wherein the substantially transparent insulator is attached to the upper side of the NIR light emitter,
  wherein the proximal end of the heat pipe is attached to the cooling element, and
  wherein the light emitter is in electrical connection with the power source.

In some embodiments based upon FIG. 14, the insulator is removed. In some embodiments based upon FIG. 14, the cooling element is removed.

Figure 15:
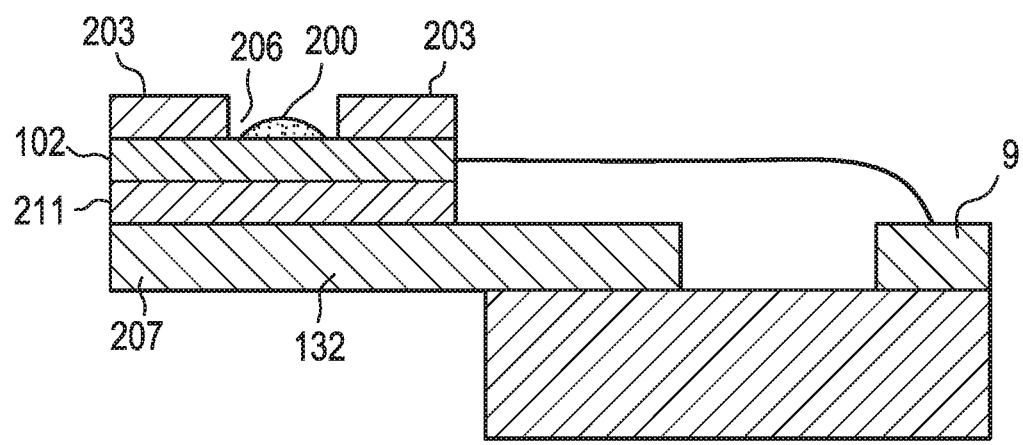
FIG. 15 schematically shows a cross-section of a device including an insulator having a hole above the LED in accordance with illustrative embodiments of the invention.

In some embodiments, and now referring to FIG. 15, the NIR light emitting device of illustrative embodiments of the invention include:
  a) an NIR light emitter 102 having a lower side 200 and an upper side 202, and an NIR LED 200 on its upper side,
  b) a thermal insulator 203 (such as a Styrofoam) having a central vertical through hole 206,
  c) a heat pipe 132 having a distal end portion 207 and a proximal end portion 209,
  d) a cooling element 213, and
  e) a power source 9,
  wherein the distal end portion of the heat pipe and the lower side of the light emitter are attached (preferably, by double side thermally conductive adhesive tape 211),
  wherein the thermal insulator is attached to the upper side of the NIR light emitter so that the through-hole is directly above the LED,
  wherein the light emitter is in electrical connection with the power source.

In some embodiments based upon FIG. 15, the insulator is removed. In some embodiments based upon FIG. 15, the cooling element is removed.

Therefore, in some embodiments, schematically shown is an NIR light emitting device comprising:
  a) an NIR light emitter having a base having a lower side and an upper side, and an NIR LED attached to the upper side of the base,
  b) a thermal insulator,
  c) a heat pipe having a distal end portion and a proximal end portion,
  d) a cooling element, and
  e) a power source,
  wherein the distal end portion of the heat pipe is attached to the lower side of the base of the NIR light emitter,
  wherein the thermal insulator is attached to the upper side of the base of the NIR light emitter,
  wherein the proximal end of the heat pipe is attached to the cooling element,
  wherein the NIR light emitter is in electrical connection with the power source.

Figure 16:
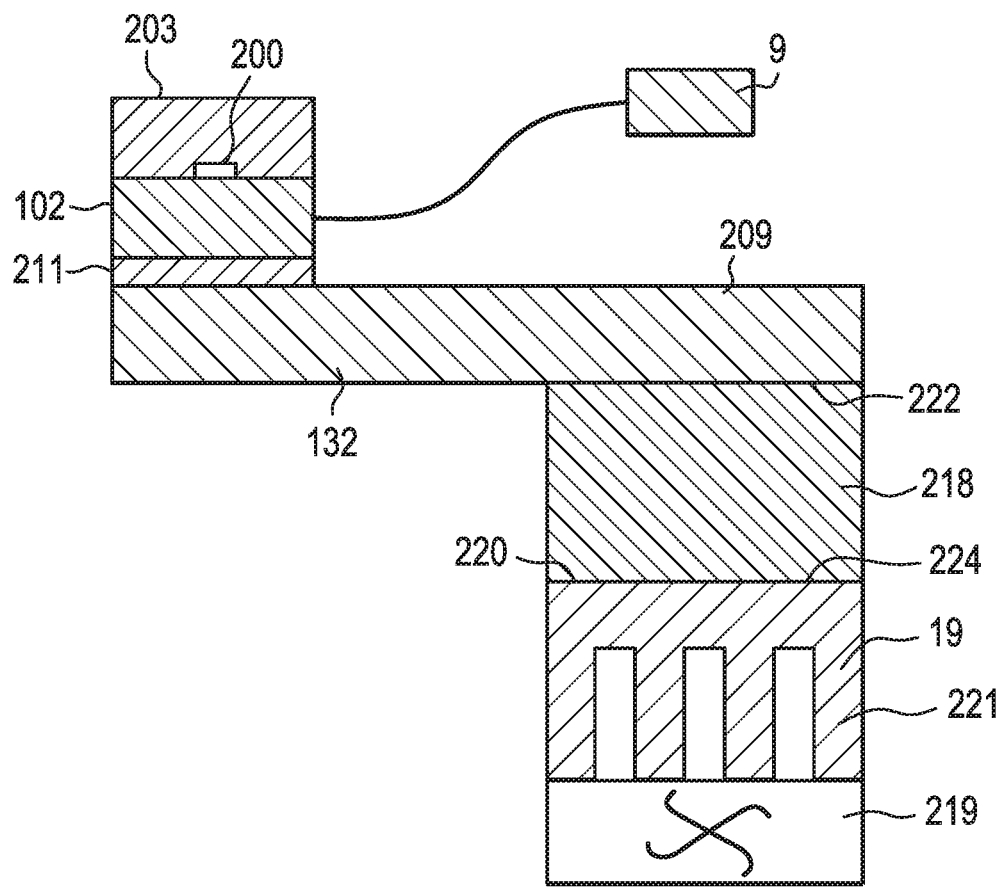
FIG. 16 schematically shows a cross-section of a device including a thermoelectric unit, a heat sink and a fan in accordance with illustrative embodiments of the invention.

In some embodiments, the cooling element comprises an ice pack or endothermic freeze pack. In other embodiments, as in FIG. 16, the cooling element comprises a peltier thermoelectric element 218 having a cool side 222 and a hot side 224, with the cool side 222 being attached to the proximal end portion 209 of the heat pipe. In some embodiments thereof, the hot side of the peltier element is attached to a first side 220 of a heat sink 217, which preferably comprises fins 221. In some embodiments, the fins are attached to a fan 219. Preferably, the peltier thermoelectric element is in electrical connection with a second power source. The fan may be in electrical connection with a third power source. In other embodiments, the cooling element comprises phase-change technology which induces cooling as a result of a phase change of a material in the cooling element. In some embodiments, the phase-change technology may include embodiments disclosed in U.S. Pat. Nos.

6,559,096; 6,688,132; 6,701,724; 6,968,711, the specifications of which are incorporated by reference in their entireties, and in the Nanocool products of Nanopore, Albuquerque, N. Mex., USA.

In some embodiments, the cooling element contacts the heat pipe in only the proximalmost third of the heat pipe. In some embodiments, the cooling element contacts the heat pipe in only the proximalmost half of the heat pipe. In some embodiments, the cooling element contacts the heat pipe in only the proximalmost two-thirds of the heat pipe. In some embodiments, the cooling element contacts the heat pipe upon substantially all but the distal most 20 mm of the heat pipe. In some embodiments, the cooling element contacts the heat pipe upon substantially all but the distal most one third of the heat pipe. In some embodiments, the cooling element contacts the heat pipe upon substantially all but the distal most one quarter of the heat pipe. In some embodiments, the cooling element contacts the heat pipe upon substantially all but the distal most one fifth of the heat pipe.

Preferably, the insulator that sits above the light emitter has a thermal conductivity of no more than 0.04 W/mK, more preferably no more than 0.03 W/mK, most preferably no more than 0.02 W/mK. In some embodiments, the insulator comprises an expanded polymer material, such as expanded polystyrene. In some embodiments, the insulator has a porosity of at least 95%, preferably at least 98%. In some embodiments, the insulator has a thickness of no more than 4 mm, preferably no more than 3 mm, more preferably no more than about 2 mm. In some embodiments, the length and width of the insulator is substantially the same as that of the light emitter it covers. In some embodiments, the insulator comprises an aerogel. In some aerogel embodiments, the base material is silica, while in others, it is a polymer. In some embodiments, the aerogel is substantially NIR transparent. In some embodiments thereof, one transparent aerogel is available from Aspen Aerogels, Inc. of Northboro, Mass., USA. In some embodiments, the transparent polymer aerogel is selected from embodiments of US 2019-0106543, the specification of which is incorporated by reference in its entirety.

In some heat pipe embodiments, the power source is a 9 Volt DC battery. In some embodiments, a lithium-based 9V battery provides a more stable, longer lasting power input. In other embodiments, the power source comprises alternating current, and in some embodiments thereof includes an AC/AC adaptor that preferably delivers energy in the form of 6V, 1 amp alternating current.

In some embodiments, electronics are included between the power source and light emitter to better manage the energy emitting by the battery or AC current. In some embodiments, the electronics includes a current driver that produces a constant non-degrading current from the DC battery. In some embodiments, the electronics includes current-limiting resistors configured to lower the current across the light emitter. In some embodiments, the electronics include a voltage splitter to lower the voltage across the light emitter while maintaining current. In some embodiments, an Arduino Uno timer is included as part of the electronics to initiate, time and end the light emitter irradiation. In some embodiments, a temperature sensor (Arduino Uno) monitors the temperature of the light emitter. In some embodiments, an optoisolator safeguards and protects the Arduino from possible power surges from the power source. In some embodiments, the optoisolator is connected to the current driver to keep the current stable and minimize temperature and current fluctuations. In some embodiments, the current driver is in series with a resistor and the light emitter in order to provide a desirable 500 mAmp, which was thought to be a desirable tradeoff amperage for producing light intensity while minimizing temperature increase. In some embodiments, a failsafe is coded into the Aruino to cut off power if the temperature of the light emitter reaches a certain maximum temperature.

In some embodiments, the electronics combined with the power source produces a voltage across the LED of about 3.2 volts and an amperage of about 0.45-0.5 amps.

The heat pipes of illustrative embodiments of the invention are typically hollow tubes with closed ends and a small amount of water under reduced pressure provided in the hollow bore. The inner surface of the heat pipe facing the bore possesses a wicking feature that can be grooved, mesh or sintered. In use, the water in the heat pipe is vaporized by heat flowing from the energized light emitter, where it travels to the cool end of the heat pipe as vapor. At the cool end, heat is rejected from the heat pipe, thereby resulting in condensation of the water vapor. The condensed liquid then travels back to the hot end of the heat pipe via the wicking structure, where the cycle is repeated. Preferably, the heat pipe has a length of between 100 mm and 250 mm; a width of between about 5 and 50 mm, and a height of between 1 mm and 5 mm. The 1 mm height heat pipe has the advantage that its profile can be easily fit into the space between the eyeball and eye socket, but has a disadvantage in that it produces a relatively low heat flux. In contrast, the 5 mm height heat pipe has the disadvantage that its profile does not easily fit into the space between the eyeball and eye socket, but has the advantage of producing a relatively high heat flux. In some embodiments, the heat pipe has a width to height ratio of at least 5:1. In some embodiments, the heat pipe has a width to height ratio of no more than 2:1. The very wide heat pipes have the advantage of carrying more than one light emitter, but they should be bent to accommodate the curvature of the eye socket in widths greater than about 10 mm. In some embodiments, the heat pipe is copper-based while in others, it is aluminum-based. In some embodiments, the heat pipe uses water as its heat flux fluid, while in other it uses acetone. As shorter heat pipes appear to transport more heat more quickly, in some embodiments, the length of the heat pipe is no more than 200 mm, preferably no more than 150 mm, more preferably no more than about 100 mm. In some embodiments, flat heat pipes from Wakefield-Vette of Pelham, N.H., USA are used.

Figure 17A:
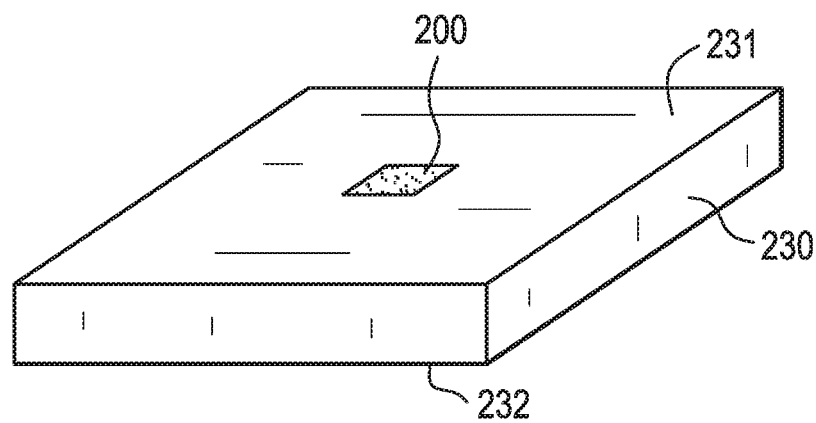
FIG. 17A schematically shows a conventional light emitter in accordance with illustrative embodiments of the invention in accordance with illustrative embodiments of the invention.

In some embodiments, and now referring to FIG. 17A, the light emitter comprises a base 230 having an upper side 231, a lower side 232, and an NIR light emitting diode (LED) 200 attached to the upper side of the base. Preferably, the dimensions of the light emitter include a height of no more than 2 mm (preferably no more than about 1 mm); a width of no more than about 10 mm (preferably no more than about 5 mm), and a length of no more than about 10 mm (preferably no more than 5 mm). In some of these embodiments, the light emitter is a Luxeon Saber Micro-Z1 850 nm light emitter, available from Quadica Developments Inc., Brantford, Ontario, CANADA. Preferably, the light emitter has a radiant power of at least about 800 mwatts, preferably at least 900 mwatts, and more preferably at least about 1000 mwatts at 1000 mamp. Preferably, the LED sits in the center of the base and has a width and length of about 1 mm.

In use, illustrative embodiments of the device may be actuated to cause irradiation from the light emitter and the distal end of the device is pressed upon the eyelid into the space between the eyeball and the top of the eye socket. In some embodiments, the heat pipe is held at an angle to the ground with the condenser end up, to take advantage of the heated vapor's tendency to rise and the condensed liquid's tendency to fall. Therapy is preferably carried out for between about 15 and 30 minutes. US 2018-0193664 (Janssen) is incorporated by reference in its entirety.

Figure 17B:
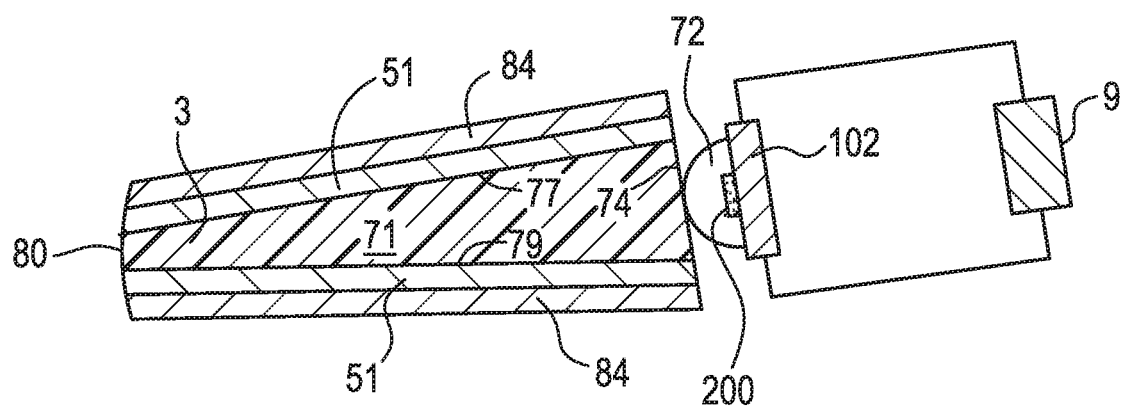
FIG. 17B schematically shows a cross-section of a light pipe in accordance with illustrative embodiments of the invention.
Figure 17C:
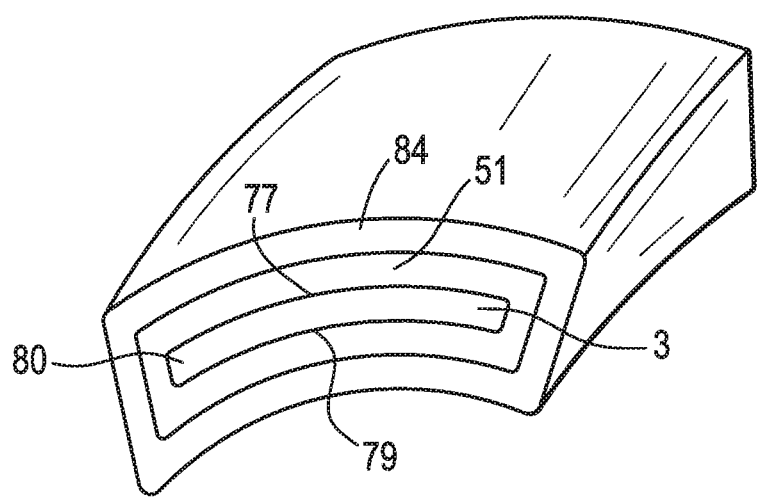
FIG. 17C schematically shows a perspective view of the distal portion of FIG. 17B.

In some embodiments, and now referring to FIGS. 17B-C, schematically shown is a light delivery device comprising:
- a) a light pipe 71 made of a substantially transparent material (such as acrylic) and comprising i) a substantially concavo-convex distal end portion 3 adapted to be positioned (e.g., inserted) in a region between the eye and the eye socket, and ii) a proximal end portion 74; iii) an upper surface 77; iv) a lower surface 79, wherein the concave portion thereof is displayed on the lower surface and the convex portion thereof is displayed on the upper surface; and v) a distal end face 80;
- b) at least one light emitter 102 positioned proximal of the proximal end portion of the light pipe, the light emitter having a NIR light emitting diode 82 oriented to shine in the distal (posterior) direction into the proximal end portion of the light pipe;
- c) a power source 9 (preferably at least one battery) electrically connected to the light emitter;
- d) a thermal insulator 51 (such as a cellulose sheet) covering at least the upper and lower surfaces of the light pipe;
- e) a metallic cladding layer 84 (such as a foil 183) covering the insulator, and
- f) a convex lens 72 positioned between the light emitter and the proximal end portion of the light pipe, the convexity of the convex lens facing distally to preferably focus light from the light emitter into the substantial center of the distal end face of the light pipe.

In some embodiments, the light emitter is a 50 W 850 nm NIR light emitter, available from Hontiey. See Hontiey Store at https://hontieychina.aliexpress.com/store/2188100. The purpose of the metal cladding layer is to protect the user from NIR light emanating through the sides of the light pipe. The purpose of the thermal insulator is to protect the user from the heat internally generated within the light pipe.

Figure 18:
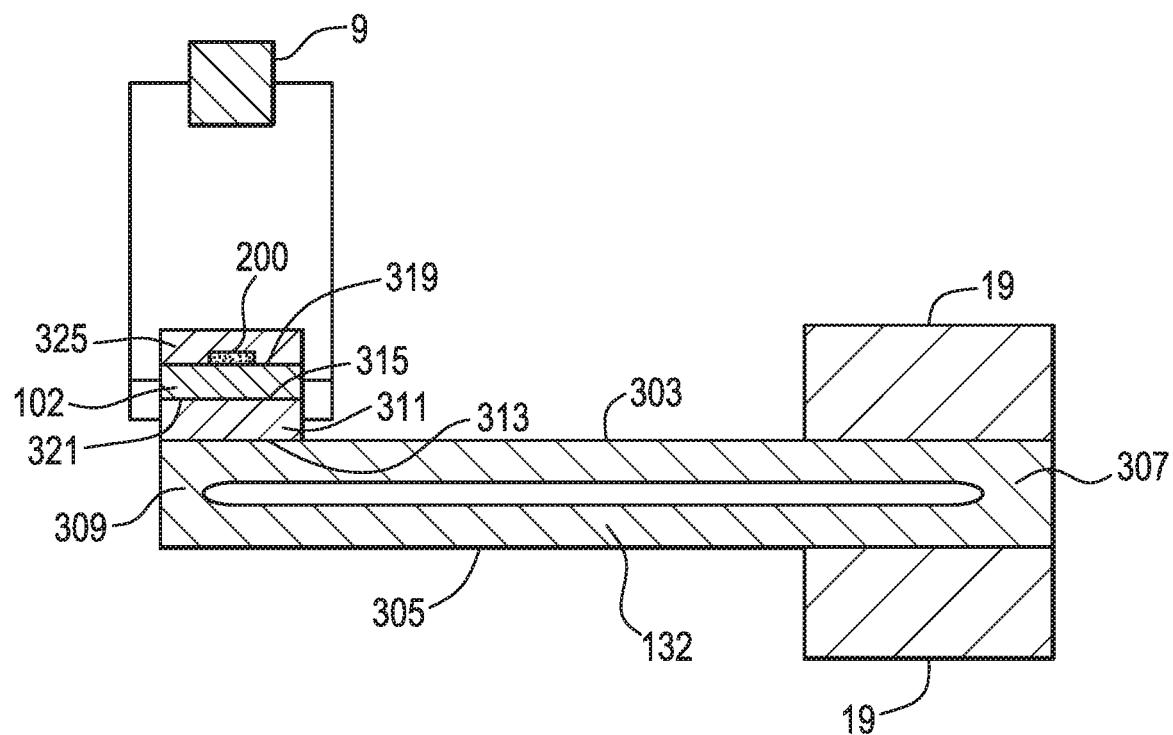
FIG. 18 schematically shows a cross-section of an embodiment having a peltier chip between the heat pipe and the LED in accordance with illustrative embodiments of the invention.

Now referring to FIG. 18, schematically shown is a light therapy device comprising:
- a) a heat pipe 132 having an upper surface 303, a lower surface 305, a proximal end portion 307 and a distal end portion 309;
- b) a Peltier thermoelectric element 311 having a lower surface 313 attached to the distal end portion of the heat pipe upon the upper surface of the heat pipe, and an upper surface 315;
- c) a light emitter 102 having an upper surface 319, a lower surface 321, and an NIR LED 200 attached to its upper surface, the lower surface of the light emitter attached to the upper surface of the thermoelectric element,
- d) an optional thermal insulator 325 (preferably an optically transparent insulator such as an aerogel) attached to the upper surface of the light emitter,
- e) at least one metallic heat sink 19 (preferably finned) attached to the proximal end portion of the heat pipe, and
- f) at least one power source 9 electrically connected to the thermoelectric element and the light emitter, wherein the power source powers the thermoelectric element to cool the upper surface of the thermoelectric element.

This embodiment is advantageous because it puts the cooling power of the Peltier chip very close to the active LED. In some embodiments of the FIG. 18, the metallic heat sink can be replaced by an ice pack, a phase change-induced cooler, or an endothermic cooler. In some embodiments, a fan can be attached to the heat sink.

Figure 19:
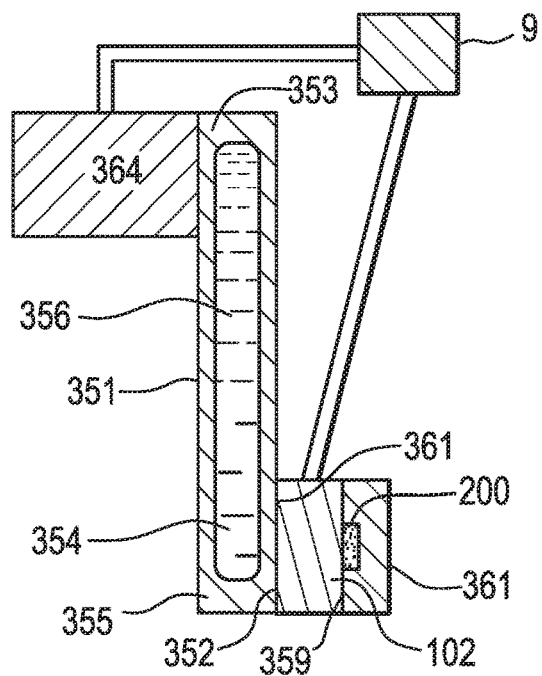
FIG. 19 schematically shows a cross-section of an embodiment in which a peltier chip cools a liquid that extends close to the LED in accordance with illustrative embodiments of the invention.

Referring now to FIG. 19, schematically shown is a light therapy device, comprising:
- a) a metal pipe 351 having a bore 354, an upper surface 352, a closed proximal end portion 353 and a closed distal end portion 355,
- b) a heat transfer fluid 356 (such as water) contained within the bore of the metal pipe,
- c) a light emitter 102 having an upper surface 359, a lower surface 361 and an NIR LED 200 attached to the upper surface 359,
- d) a thermal insulator 361 (preferably an optically transparent insulator such as a transparent aerogel) attached to the upper surface of the light emitter,
- e) a thermoelectric element 364 attached to the closed proximal end portion of the metal pipe,
- f) at least one power source 9 electrically connected to the thermoelectric unit and the light emitter, wherein the power source is adapted to power the thermoelectric unit to cool the metal pipe.

In some variants of FIG. 19, the thermoelectric element is replaced by an ice pack, a phase-change cooled unit, or an endothermically-activated unit.

Figure 20:
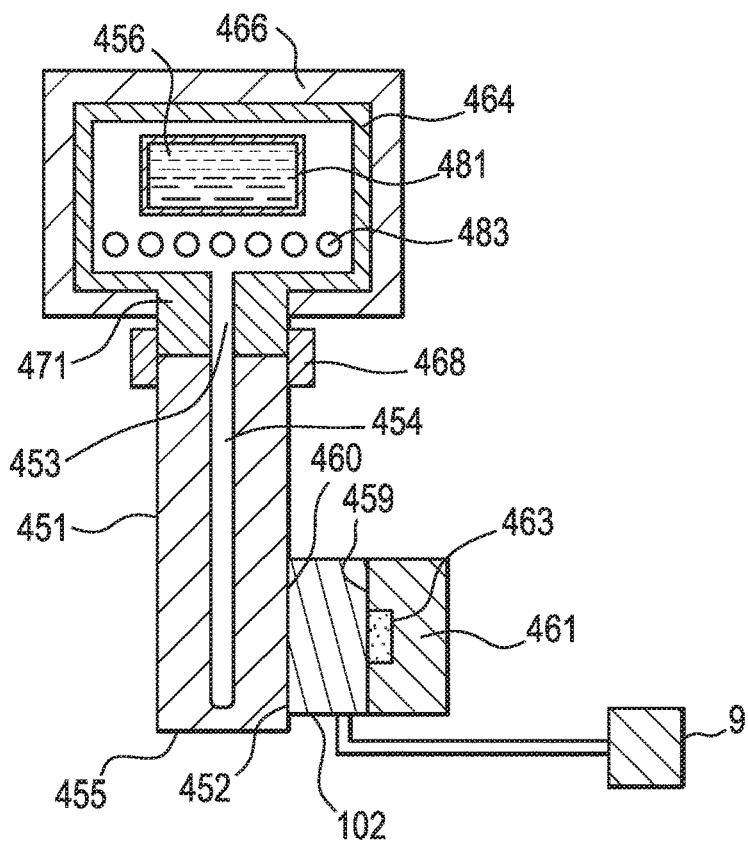
FIG. 20 schematically shows a cross-section of an embodiment in which an endothermically chilled liquid extends close to the LED in accordance with illustrative embodiments of the invention.

Referring now to FIG. 20, schematically shown is a light therapy device, comprising:
- a) a metal pipe 451 having a bore 454, an upper surface 452, an open proximal end portion 453 and a closed distal end portion 455,
- b) a light emitter 102 having an upper surface 459, a lower surface 460 and an NIR LED 463 attached to the upper surface 459,
- c) an optional thermal insulator 461 (preferably an optically transparent insulator such as a transparent aerogel) attached to the upper surface of the light emitter,
- d) a squeezable container 464 having a spout 471 fluidly attached to the open proximal end portion of the metal pipe,
- e) a burstable bag 481 located within the container,
- f) water 456 contained within the burstable bag 481,
- g) a plurality of endothermic beads 483 contained within the container,
- h) heat shrink tubing 468 surrounding the fluid attachment of the container and the metal pipe,
- i) insulation 466 surrounding the squeezable container;
- j) at least one power source 9 electrically connected to the light emitter.

In use, the squeezable container is squeezed, thereby rupturing the burstable bag containing the water and releasing the water. The water mixes with the endothermic beads, thereby solubilizing the beads, causing an endothermic reaction and lowering the temperature of the water. The chilled water travels to the closed distal end portion of the metal pipe, where it cools the active LED. Preferably, the diameter of the beads is greater than the diameter of the bore.

Figure 21A:
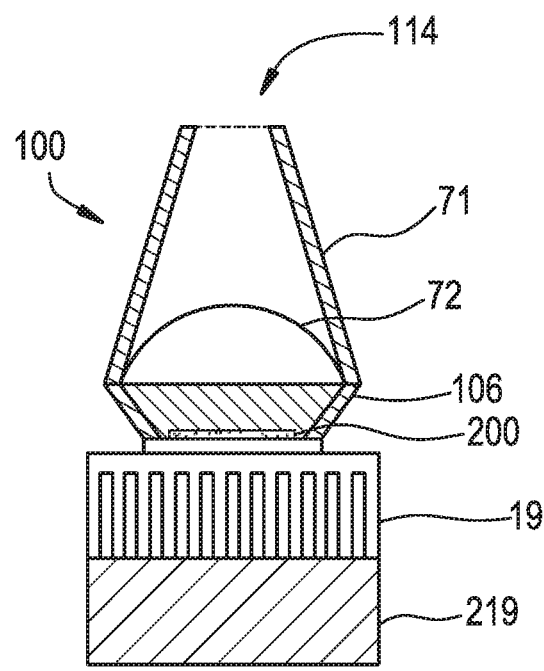
FIGS. 21A and 21B schematically show cross sections of LED devices having a light pipe, lens, heat ink and fan in accordance with illustrative embodiments of the invention.
Figure 21B:
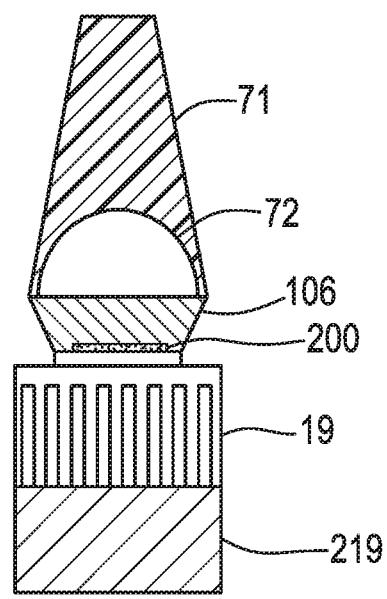

FIGS. 21A and 21B schematically show a device 100 featuring a near infrared (NIR) LED 200 placed on top of a finned heat sink 19 and fan 219 in accordance with illustrative embodiments of the invention. The heat sink 19 and fan 219 work in conjunction to remove excess heat that is produced when powering a light emitter, such as the LED 200. The light is passed into a reflector 106 that redirects low-angled divergent light towards the lens 72. The lens 72 then focuses the beam spread, towards a central focal spot at the distal end 114 of a light guide 104 (e.g., such as a light pipe). The light pipe 104 is preferably a hollow, conical piece of heat resistant plastic. The distal tip of the light pipe 104 may have a concavo-convex shape configured to match the curvature of the orbit anatomy.

In some embodiments, the hollow light pipe 104 may be formed from metal and/or internally coated with NIR reflective metal. For example, the light pipe 104 may be a metal pipe, which advantageously dissipates heat into the surrounding air throughout its whole surface area. The NIR reflective surface is advantageous for internal reflectance and maximizing the irradiance output from the light pipe 104. Furthermore, some embodiments may not include the reflector 106.

FIGS. 21A and 21B schematically show a light delivery device comprising:
- a) a light pipe (preferably hollow) having an upper surface, a lower surface, a proximal end portion and a distal end portion, wherein the lower and upper surfaces in the region of the distal end portion form a substantially concavo-convex shape,
- b) a convex lens having a convex distal surface and a proximal surface,
- c) a reflector having a proximal surface, a distal surface and a light reflective surface therebetween,
- d) a light emitter having a proximal end portion, a distal end portion having a distal end surface and a near infrared light emitting diode on the distal end surface,
- e) an optional heat sink (preferably a finned heat sink) having a proximal surface and a distal surface,
- f) an optional fan wherein the proximal surface of the convex lens is attached to the distal surface of the reflector and oriented so that the convexity faces distally, wherein the proximal end portion of the light pipe is attached to the distal surface of the reflector, wherein the distal end portion of the light emitter is attached to the proximal surface of the reflector, wherein the proximal end portion of the light emitter is attached to the distal surface of the heat sink, and wherein the fan is attached to the proximal surface of the heat sink.

While FIG. 21A shows the device 100 having a light guide (e.g., the hollow light pipe 71 formed from a light reflective material, such as a metal). In some embodiments the light pipe 71 may be solid as shown in FIG. 21B. The solid light pipe 71 may be formed from a substantially transparent material, such as acrylic.

Figure 22A:
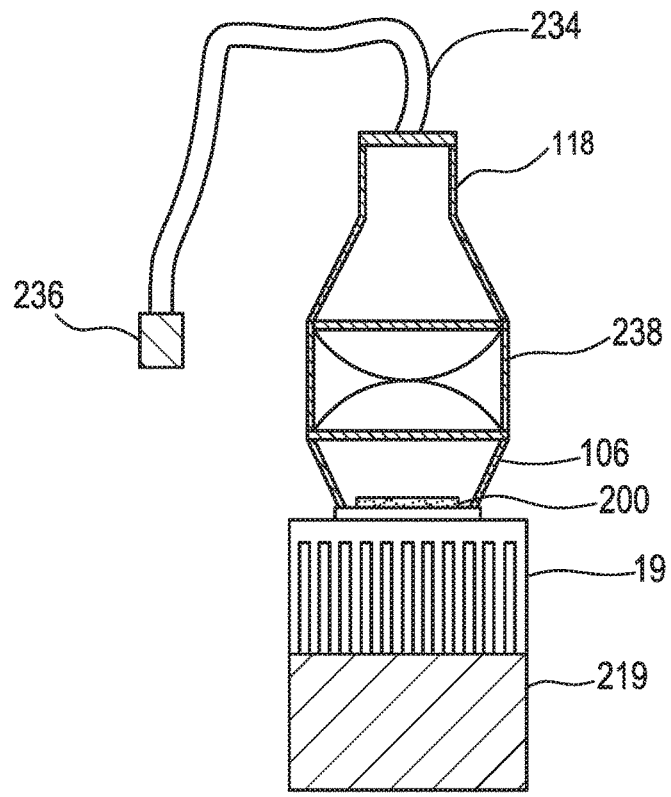
FIGS. 22A and 22B schematically show cross sections of LED devices having a fiber optic cable and eyepiece in accordance with illustrative embodiments of the invention.
Figure 22B:
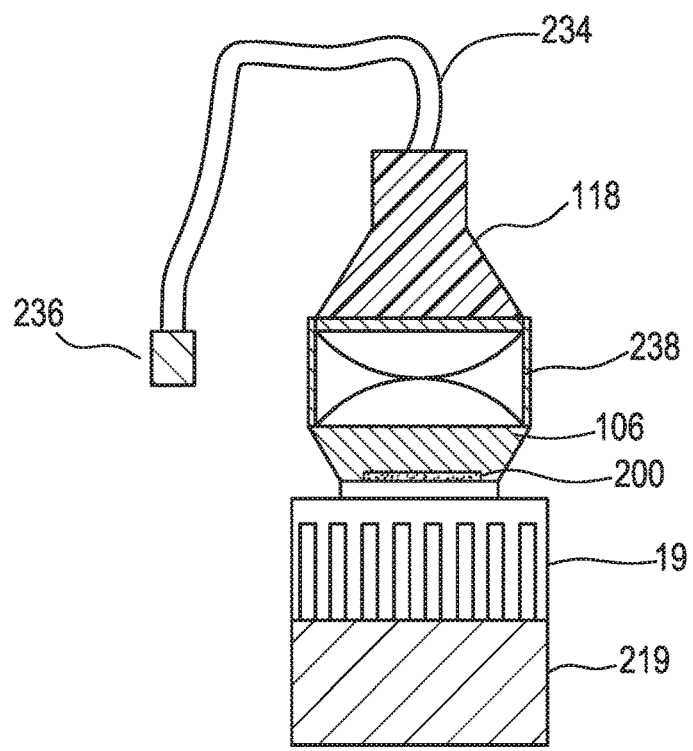

FIGS. 22A-22B schematically show the device 100 having a lens doublet 238 and a fiber optic cable 234 connected to an eye piece 236. In a manner similar to the embodiments shown in FIGS. 21A-21B, the device 100 includes a Near Infrared LED 200 chip that rests upon the finned heat sink 19 and the fan 219. The light produced by the NIR LED 200 is first directed through the reflector 106 to reflect low-angled divergent light into the above lens doublet 238 system. Illustrative embodiments collimate and focus the light from the LED 200 into the fiber optic cable 234. A housing 118 is provided for structure and to enclose the transmitted light. At the end of the fiber optic cable 234 is an eyepiece 236. The eyepiece 236 is configured to fit comfortably within the orbital socket and to direct the light towards the desired location for maximized therapeutic output.

FIGS. 22A-22B schematically show a light delivery device including:
- a) an eyepiece
- b) a fiber optic cable having a proximal end portion and a distal end portion,
- c) a hollow housing having an upper surface, a lower surface, a proximal end portion and a distal endportion,
- d) a doublet lens having a distal surface and a proximal surface,
- e) a reflector having a proximal surface, a distal surface and a light reflective surface therebetween,
- f) a light emitter having a proximal end portion, a distal end portion having a distal end surface and a near infrared light emitting diode on the distal end surface,
- g) an optional heat sink (preferably a finned heat sink) having a proximal surface and a distal surface,
- h) an optional fan, In the embodiment shown in FIGS. 22A-22B, the eyepiece is attached to the distal end portion of the fiber optic cable. The proximal end portion of the fiber optic cable is attached to the distal end portion of the housing, and the proximal surface of the doublet lens is attached to the distal surface of the reflector. The distal surface of the doublet lens is attached to the proximal end portion of the housing, and the distal end portion of the light emitter is attached to the proximal surface of the reflector, wherein the proximal end portion of the light emitter is attached to the distal surface of the heat sink. Furthermore, the fan is attached to the proximal surface of the heat sink.

Although FIG. 22A shows the device 100 with a hollow housing 118 made of a light reflective material such as a metal, in some embodiments, the housing may be solid, as shown in FIG. 22B. Among other things, the solid housing may be formed from a substantially transparent material, such as acrylic.

Figure 23A:
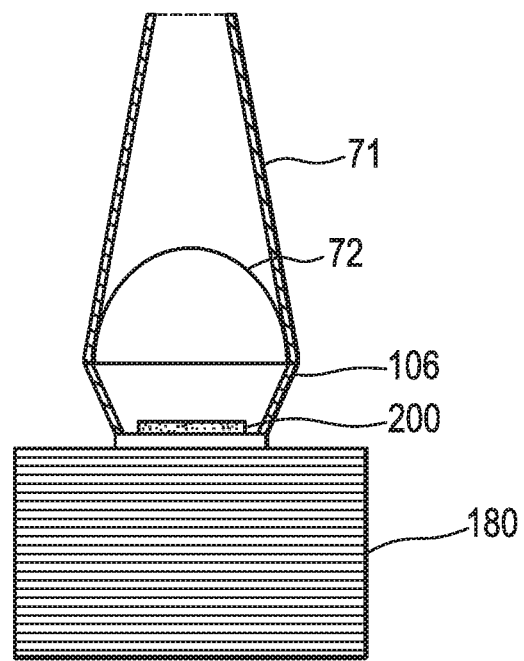
FIGS. 23A and 23B schematically show cross-sections of LED devices having a phase change cooling element in accordance with illustrative embodiments of the invention.
Figure 23B:
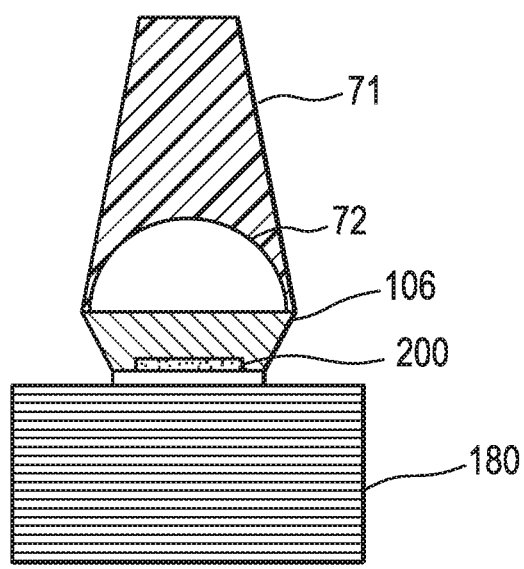

FIGS. 23A and 23B show the device 100 including a phase change based nanocool cooling system 180 in place of the finned heat sink and fan. In illustrative embodiments, the phase change cooling system may be a one-time use product.

Now referring to FIGS. 23A and 23B, schematically shown is a light delivery device comprising:
- a) a light pipe (preferably hollow) having an upper surface, a lower surface, a proximal end portion and a distal endportion, wherein the lower and upper surfaces in the region of the distal end portion form a substantially concavo-convex shape,
- b) an optional convex lens having a convex distal surface and a proximal surface,
- c) a reflector having a proximal surface, a distal surface and a light reflective surface therebetween,
- d) a light emitter having a proximal end portion, a distal end portion having a distal end surface and a near infrared light emitting diode on the distal end surface,
- e) a phase change cooling element wherein the proximal surface of the convex lens is attached to the distal surface of the reflector and oriented so that the convexity faces distally, wherein the proximal end portion of the light pipe is attached to the distal surface of the reflector, wherein the distal end portion of the light emitter is attached to the proximal surface of the reflector, and wherein the proximal end portion of the light emitter is attached to the distal surface of the cooling element.

FIG. 23B schematically shows an alternative embodiment where the light pipe 71 is solid, and formed from a substantially transparent material (e.g., acrylic).

Figure 24A:
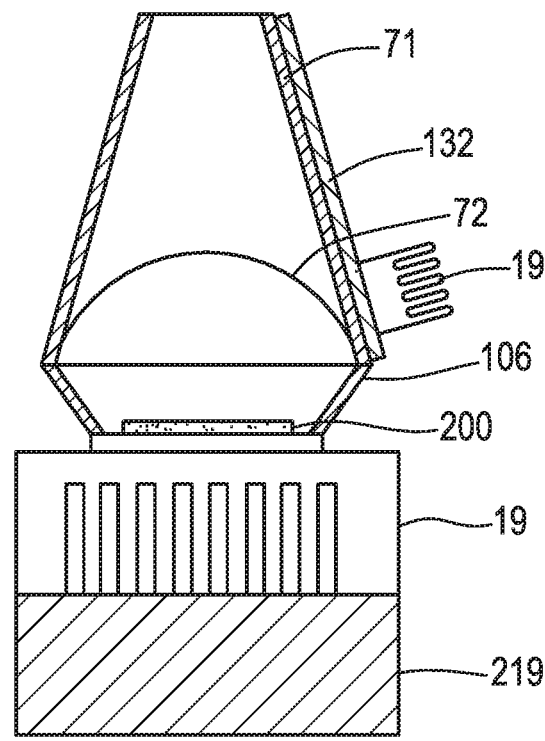
FIGS. 24A-24D schematically show side and front views of LED devices having a heat pipe in accordance with illustrative embodiments of the invention.
Figure 24B:
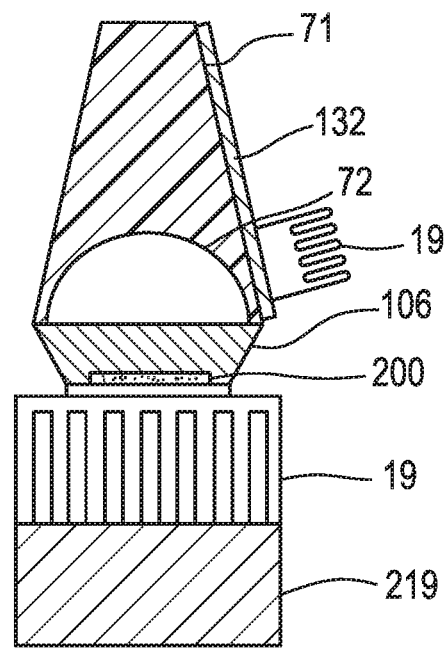
Figure 24C:
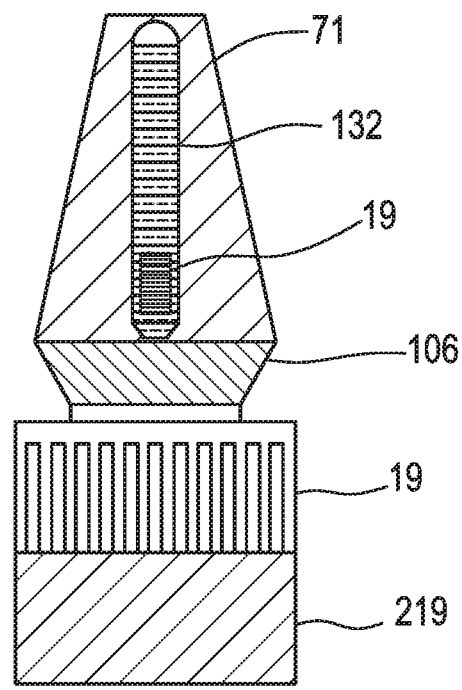

FIGS. 24A and 24C schematically show the hollow light pipe 71 in accordance with illustrative embodiments of the invention. FIG. 24A shows a front view and FIG. 24C shows a side view.

Figure 24D:
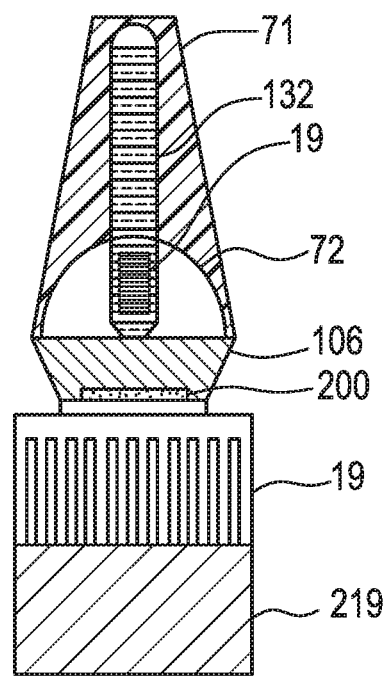

FIGS. 24B and 24D schematically show the hollow light pipe 71 in accordance with illustrative embodiments of the invention. FIG. 24B shows a front view and FIG. 24D shows a side view. As shown, the device 100 has the heat sink and fan system discussed earlier, and additionally, includes a heat pipe with a finned heat sink on the surface of the light pipe. The heat pipe transfers heat away from the distal end of the pipe, towards a second heat sink. Accordingly, illustrative embodiments reduce the temperature at the eyelid.

Now referring to FIGS. 24A-D, schematically shown is a light delivery device comprising:
a) a light pipe (preferably hollow) having an upper surface, a lower surface, a proximal end portion and a distal end portion, wherein the lower and upper surfaces in the region of the distal end portion form a substantially concavo-convex shape,
b) a convex lens having a convex distal surface and a proximal surface,
c) a reflector having a proximal surface, a distal surface and a light reflective surface therebetween,
d) a light emitter having a proximal end portion, a distal end portion having a distal end surface and a near infrared light emitting diode on the distal end surface,
e) an optional first heat sink (preferably a finned heat sink) having a proximal surface and a distal surface,
f) an optional first fan
g) a heat pipe having a proximal end portion, and
h) an optional second heat sink (preferably finned heat sink)

wherein the proximal surface of the convex lens is attached to the distal surface of the reflector and oriented so that the convexity faces distally, wherein the proximal end portion of the light pipe is attached to the distal surface of the reflector, wherein the distal end portion of the light emitter is attached to the proximal surface of the reflector, wherein the proximal end portion of the light emitter is attached to the distal surface of the heat sink, wherein the fan is attached to the proximal surface of the heat sink, wherein the heat pipe is attached lengthwise to the light pipe, and wherein the second heat sink is attached to the proximal end portion of the heat pipe.

Whereas FIGS. 24A and 24C show the device with the hollow light pipe formed of a light reflective material, such as a metal, in an alternative embodiment, schematically shown is in FIGS. 24B and D, a device substantially similar to that of FIGS. 24A and C, except that the light pipe is a solid, and formed from a substantially transparent (preferably acrylic) material.

Also, in some embodiments, the reflector is eliminated.

Figure 25:
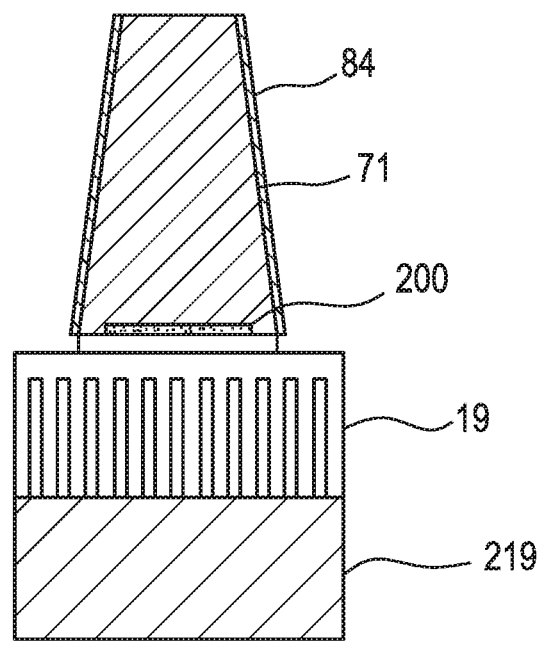
FIG. 25 schematically shows a cross section of an LED device with a metal coated acrylic light pipe in accordance with illustrative embodiments of the invention.

FIG. 25 schematically shows another embodiment of the device including the solid light pipe in accordance with illustrative embodiments of the invention. As discussed previously, the light pipe may be formed from a substantially transparent to NIR wavelength light material (e.g., acrylic). The light pipe may include a NIR wavelength reflective coating 84 to prevent and/or reduce light from leaving the light pipe unintentionally. For example, a layer of metal coating may be used to either reflect the light inward or absorb the light, as to not leak NIR light to other unintended areas of the patient's skin. Additionally, or alternatively, illustrative embodiments may have no reflector and/or lens, but may include the NIR LED, the heatsink, and the fan.

In some embodiments, the light delivery device includes:
a) a light pipe (e.g., solid) having an upper surface, a lower surface, a proximal end portion and a distal end portion, wherein the lower and upper surfaces in the region of the distal end portion form a substantially concavo-convex shape,
b) a metallic coating on the upper and lower surfaces of the light pipe,
c) a light emitter having a proximal end portion, a distal end portion having a distal end surface and a near infrared light emitting diode on the distal end surface,
d) an optional heat sink (preferably a finned heat sink) having a proximal surface and a distal surface, and
e) an optional fan The distal end portion of the light emitter may be attached to the proximal end portion of the light pipe. The proximal end portion of the light emitter may be attached to the distal surface of the heat sink. The fan may be attached to the proximal surface of the heat sink.

Figure 26A:
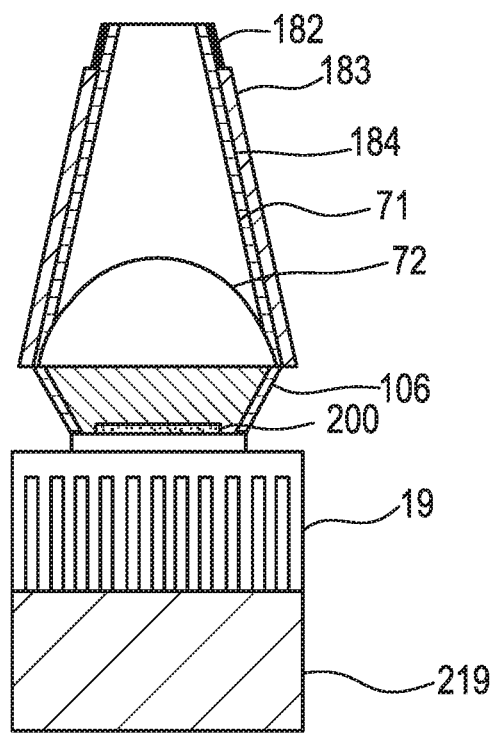
FIGS. 26A-26B schematically show cross sections of LED devices having an insulating layer on the light pipe in accordance with illustrative embodiments of the invention.
Figure 26B:
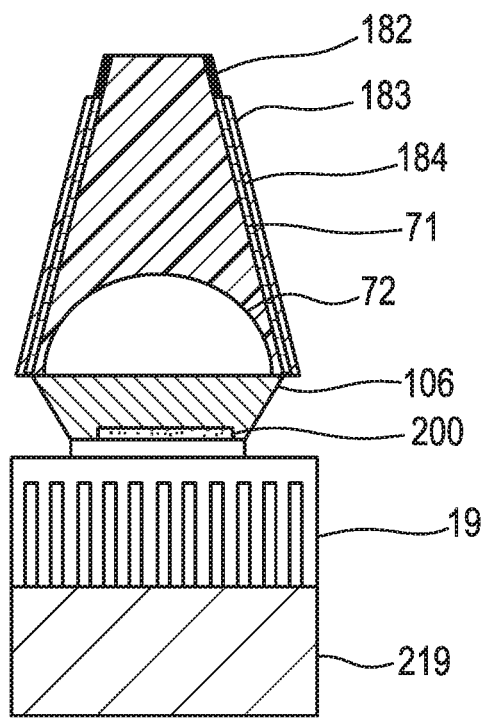

FIGS. 26A-26B schematically show the light pipe with two layers of coating and a polystyrene-coated tip, in accordance with illustrative embodiments of the invention. In the FIGS. 26A and 26B, the light pipe with layers of material on the outside surface. From the proximal base, until 1 cm from the distal tip, the pipe is covered in a base layer of a semi-transparent insulator (white paper 184). Surrounding the base layer is a film of aluminum foil. The deflects heat into the surrounding air, while the base layer shields the inner pipe from the hot foil. The surface of the light pipe's distal tip (e.g., the distal most 1 cm of the pipe) is coated in polystyrene to thermally insulate the patient's skin from the pipe.

Now referring to FIGS. 26A and 26B, schematically shown is a light delivery device comprising:
a) a light pipe (preferably hollow) having an upper surface, a lower surface, a proximal end portion and a distal endportion, wherein the lower and upper surfaces in the region of the distal end portion form a substantially concavo-convex shape,
b) a convex lens having a convex distal surface and a proximal surface,
c) a reflector having a proximal surface, a distal surface and a light reflective surface therebetween,
d) a light emitter having a proximal end portion, a distal end portion having a distal end surface and a near infrared light emitting diode on the distal end surface,
e) an optional heat sink (preferably a finned heat sink) having a proximal surface and a distal surface,
f) an optional fan
g) an optional insulation layer having an inner and outer surface, and
h) an optional metal foil
i) an optional porous plastic layer (such as Styrofoam 182)

wherein the proximal surface of the convex lens is attached to the distal surface of the reflector and oriented so that the convexity faces distally, wherein the proximal end portion of the light pipe is attached to the distal surface of the reflector, wherein the distal end portion of the light emitter is attached to the proximal surface of the reflector, wherein the proximal end portion of the light emitter is attached to the distal surface of the heat sink, and wherein the fan is attached to the proximal surface of the heat sink, wherein the inner surface of the insulating layer is attached to the upper and lower surfaces of the light pipe, wherein the metal foil is attached to the outer layer of the insulating layer.

wherein the porous plastic layer is attached to the distal end portion of the light pipe on the upper and lower surfaces thereof.

Whereas FIG. 26A shows the device with a hollow light pipe made of a light reflective material such as a metal, in an alternate embodiment, there is provided in FIG. 26B, a device substantially similar to that of FIG. 26A, except that the light pipe is a solid, substantially transparent (preferably acrylic) component.

Figure 27:
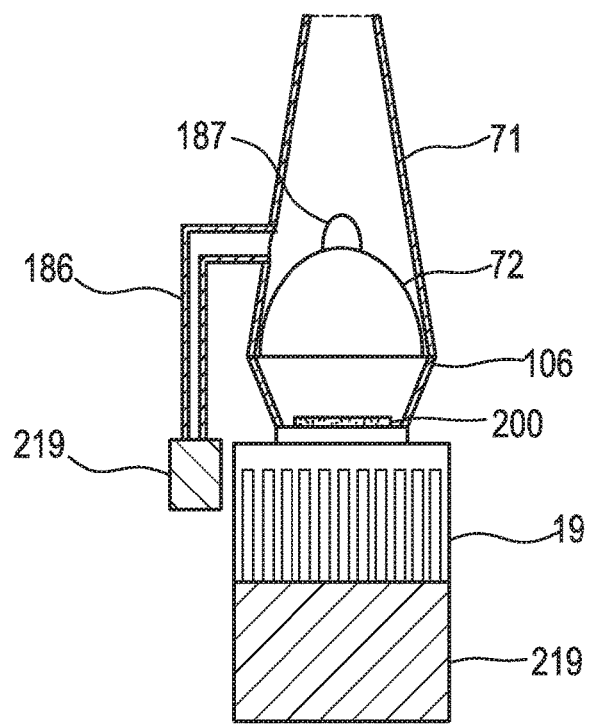
FIG. 27 schematically shows a cross-section of an LED device with an actively ventilated light pipe in accordance with illustrative embodiments of the invention.

FIG. 27 schematically shows a light pipe with ventilation in accordance with illustrative embodiments of the invention. In the FIG. 27, the hollow light pipe has been modified to include a ventilation system. The hollow pipe has holes on each side to allow for airflow, with one being attached to a fan via some tubing. This will act as a way to pump cool air into the hot light pipe in order to slow the heating of the device.

Now referring to FIG. 27, there is provided a light delivery device comprising:
 a) a hollow light pipe having an upper surface, a lower surface, a proximal end portion and a distal endportion, wherein the lower and upper surfaces in the region of the distal end portion form a substantially concavo-convex shape, wherein at least one of the upper and lower surfaces has a port
 b) a convex lens having a convex distal surface and a proximal surface,
 c) a reflector having a proximal surface, a distal surface and a light reflective surface therebetween,
 d) a light emitter having a proximal end portion, a distal end portion having a distal end surface and a near infrared light emitting diode on the distal end surface,
 e) an optional heat sink (preferably a finned heat sink) having a proximal surface and a distal surface,
 f) an optional first fan
 g) tubing having a first and second end,
 h) a second fan
wherein the proximal surface of the convex lens is attached to the distal surface of the reflector and oriented so that the convexity faces distally,
wherein the proximal end portion of the light pipe is attached to the distal surface of the reflector,
wherein the distal end portion of the light emitter is attached to the proximal surface of the reflector,
wherein the proximal end portion of the light emitter is attached to the distal surface of the heat sink, and
wherein the first fan is attached to the proximal surface of the heat sink,
wherein the first end of the tubing is connected to the port, and
wherein the second end of the tubing is connected to the second fan.

Also, in some embodiments, the reflector is eliminated.

Figure 28A:
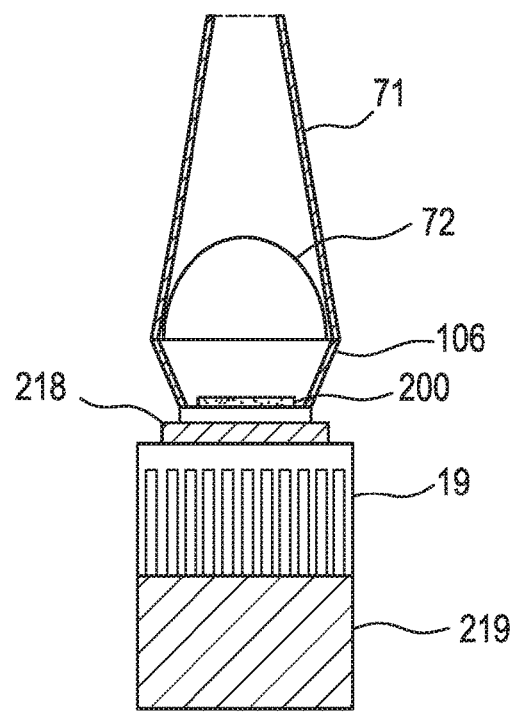
FIGS. 28A-28B schematically show cross-sections of LED devices with a peltier chip attached to the LED in accordance with illustrative embodiments of the invention.
Figure 28B:
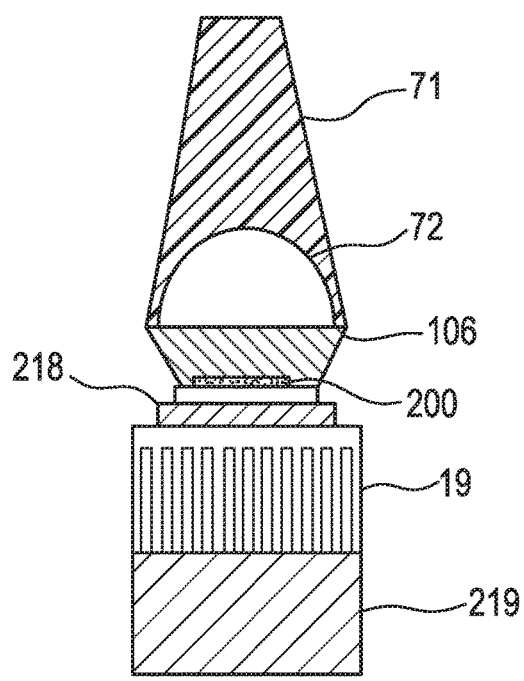

FIGS. 28A-28B schematically show the light pipe with the peltier chip, the lens, the heat sink, and the fan, in accordance with illustrative embodiments of the invention.

In the FIGS. 28A-28B, the Peltier chip has been placed in between the finned heat sink and the NIR LED chip. This quickens the heat exchange between the heat sink and the NIR LED chip by polarizing temperatures on its opposite surfaces, creating a cool interface with the NIR LED array while transferring heat to the heat sink and fan system to be dissipated.

Now referring to FIGS. 28A-28B, there is provided a light delivery device comprising:
 a) a light pipe (preferably hollow) having an upper surface, a lower surface, a proximal end portion and a distal endportion, wherein the lower and upper surfaces in the region of the distal end portion form a substantially concavo-convex shape,
 b) a convex lens having a convex distal surface and a proximal surface,
 c) a reflector having a proximal surface, a distal surface and a light reflective surface therebetween,
 d) a light emitter having a proximal end portion, a distal end portion having a distal end surface and a near infrared light emitting diode on the distal end surface,
 e) an optional heat sink (preferably a finned heat sink) having a proximal surface and a distal surface,
 f) an optional fan
 g) a peltier thermoelectric element having a proximal surface and a distal surface,
wherein the proximal surface of the convex lens is attached to the distal surface of the reflector and oriented so that the convexity faces distally,
wherein the proximal end portion of the light pipe is attached to the distal surface of the reflector,
wherein the distal end portion of the light emitter is attached to the proximal surface of the reflector,
wherein the proximal end portion of the light emitter is attached to the distal end surface of the peltier thermoelectric element,
wherein the proximal end surface of the peltier thermoelectric element is attached to the distal surface of the heat sink, and
wherein the fan is attached to the proximal surface of the heat sink.

Whereas FIG. 28A shows the device with a hollow light pipe made of a light reflective material such as a metal, in an alternate embodiment, there is provided in FIG. 28 B, a device substantially similar to that of FIG. 28A, except that the light pipe is a solid, substantially transparent (preferably acrylic) component.

Also, in some embodiments, the reflector is eliminated.

Figure 29:
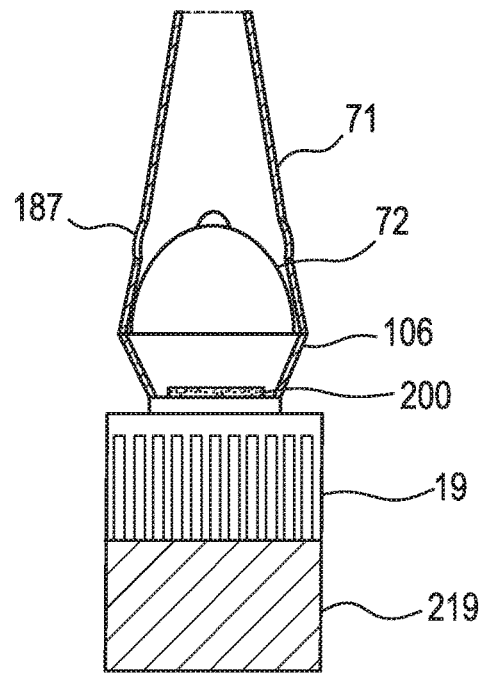
FIG. 29 schematically shows a cross-section of an LED device having a passively ventilated light pipe in accordance with illustrative embodiments of the invention.

FIG. 29 schematically shows a ported light pipe in accordance with illustrative embodiments of the invention. FIG. 29 is the hollow light pipe design with air ports. This design is similar to the ventilation embodiment, however, this simply lets the air flow out without the assistance of a fan.

Now referring to FIG. 29, there is provided a light delivery device comprising:
 a) a hollow light pipe having an upper surface, a lower surface, a proximal end portion and a distal endportion, wherein the lower and upper surfaces in the region of the distal end portion form a substantially concavo-convex shape, wherein at least one of the upper and lower surfaces has a port 187 connecting an inside of the light pipe to an outside of the light pipe,
 b) a convex lens having a convex distal surface and a proximal surface,
 c) a reflector having a proximal surface, a distal surface and a light reflective surface therebetween,
 d) a light emitter having a proximal end portion, a distal end portion having a distal end surface and a near infrared light emitting diode on the distal end surface,
 e) an optional heat sink (preferably a finned heat sink) having a proximal surface and a distal surface,
 f) an optional first fan
wherein the proximal surface of the convex lens is attached to the distal surface of the reflector and oriented so that the convexity faces distally,
wherein the proximal end portion of the light pipe is attached to the distal surface of the reflector,
wherein the distal end portion of the light emitter is attached to the proximal surface of the reflector,
wherein the proximal end portion of the light emitter is attached to the distal surface of the heat sink, and
wherein the first fan is attached to the proximal surface of the heat sink.

Also, in some embodiments, the reflector is eliminated.

Figure 30A:
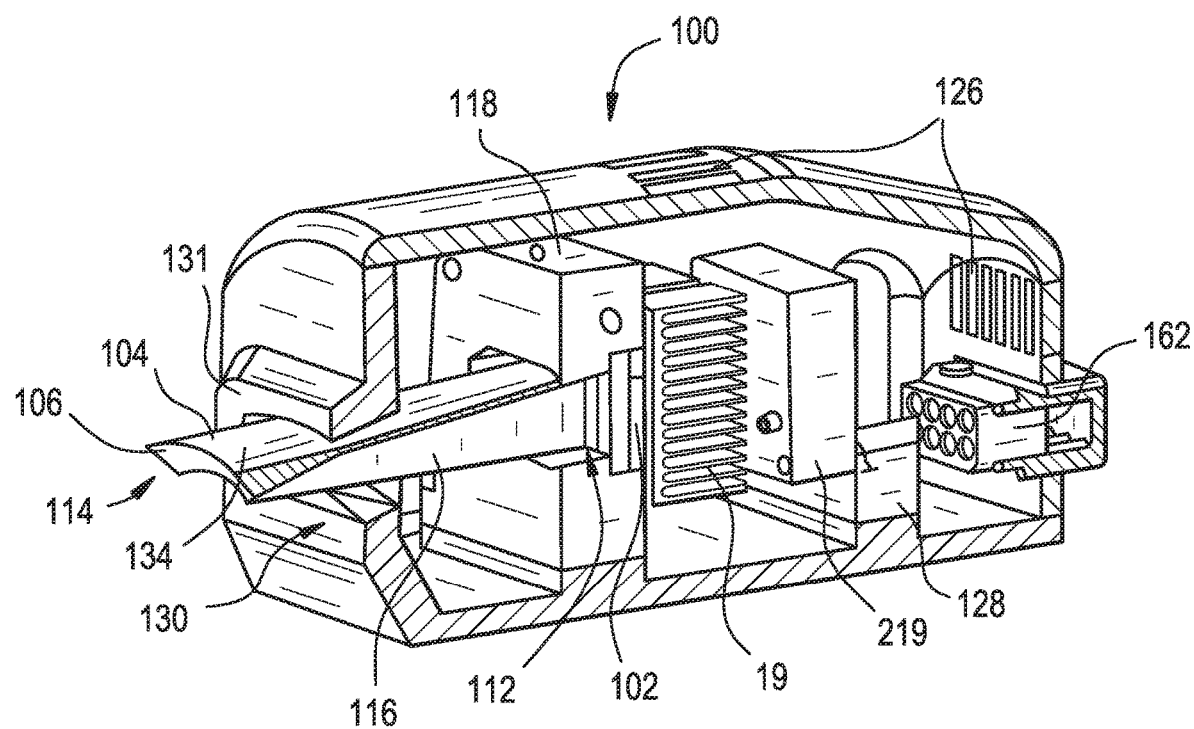
FIGS. 30A and 30B schematically shows a device that treats a patient in accordance with illustrative embodiments of the invention.
Figure 30B:
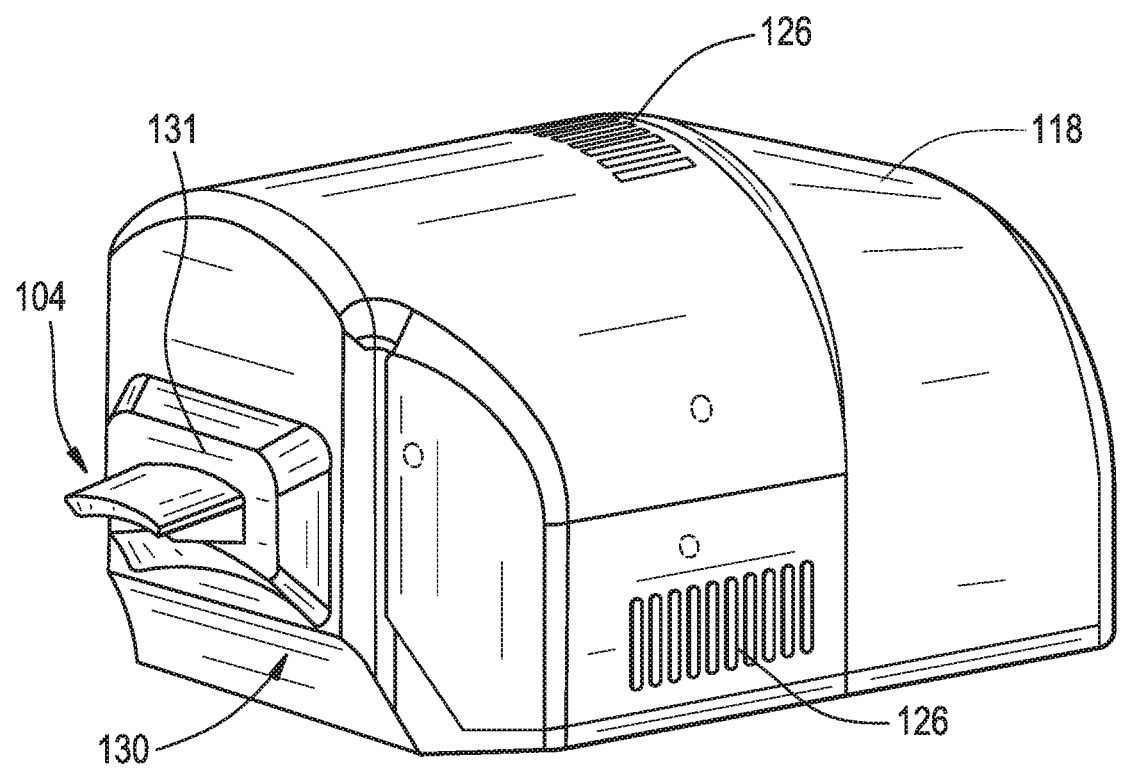

FIGS. 30A and 30B schematically shows a device 100 that treats a patient in accordance with illustrative embodiments of the invention. As described previously, the device 100 treats the patient by providing light in the near-infrared (NIR) spectrum to the brain. To that end, the device 100 has at least one NIR light source 102, such as an LED or laser. Although illustrative embodiments below are discussed with reference to transorbital delivery, it should be understood that various embodiments may additionally, or alternatively, apply to transcranial, intracranial, oral, and/or intranasal delivery.

To deliver NIR light transorbitally, illustrative embodiments position the device 100, or a portion thereof, in the orbital socket of the patient, such that the NIR light is emitted towards the frontal lobe of the brain. The emitter 102 has a light emitting surface that emits the NIR light towards a light guide 104. The light guide 104 guides the light towards a first direction. In some embodiments, the first direction is generally towards a distal end 130 of the housing 118 of the device 100. Additionally, or alternatively, the first direction may be towards a reflector 106 that is configured to reflect the light towards a second direction (discussed further below).

The light guide 104 may be formed from a solid material, such as a transparent acrylic material. While the light guide 104 can take alternate forms (e.g., hollow), in this embodiment the light guide may be formed from a solid material. In some embodiments, the light guide 104 has a proximal end 112 configured to receive the emitted NIR light from the emitter 102, and a distal end 114 through which the light exits the guide 104. In some embodiments, the light may enter and exit the guide 104 near the proximal end 112 and the distal end 114, respectively. Accordingly, illustrative embodiments should not be considered as being limited to receiving and/or transmitting light from end surfaces of the guide 104. Indeed, in some embodiments, the upper distal surface of the light guide 104 has an opening and/or a window through which the NIR light escapes.

During transorbital NIR light delivery, a tip 134 of the light guide 104 is positioned between the patient's eyelid and eye socket (i.e., in the periorbital space around the patient's eye). Accordingly, as discussed further below with reference to FIGS. 32A-32B, the tip 134 and/or the entire light guide 104 may have a concavo-convex shape configured to conform to the shape of the eye. In illustrative embodiments, the tip 134 extends past the distal face 131 of the housing 118 and/or from a flange that couples with the housing 118 by at least 6 mm. In some embodiments, the tip 134 extends between about 5 mm and about 20 mm. In some embodiments, the tip 134 extends about 15 mm. Illustrative embodiments preferably have a tip 134 with a length that is greater than the thickness of the human frontal bone in the skull.

In some embodiments, the reflector 106 may be formed by an exposed portion of reflective material 116 on the light guide 104. The reflective material 116 is configured to transmit all or substantially all of the received light from the proximal end 112 to the distal end 114 of the light guide 104. To that end, the material 116 may be configured to cause total internal reflection of the NIR light between the proximal end 112 and the distal end 114 of the light guide 104. The material 116 may be formed of a metal, such as aluminum. In some embodiments, the metallic material 116 may form a coating around the solid light guide 104. Thus, the NIR light may reflect off the inner surface of the reflective material 116 as it travels through the light guide 104 towards the reflector 106.

In some embodiments, the reflective material 116 may be coated on all of the surfaces of the device 100 except for the light guide-emitter interface and an opening 152 or a NIR light transparent window on the distal tip 134 (e.g., the dorsal face of the tip 134). A portion of the reflective material 116 is configured to reflect light towards the periorbital space through the opening 152 and/or window, and thus, acts as the reflector 106.

Because the reflective material 116 may absorb some of the light as it travels along the guide 104, illustrative embodiments may use a higher intensity light emitter 102 (also referred to as a light source 102) than may otherwise be required to deliver the effective dosage if none of the light was absorbed. For example, the light source 102 may be, for example, a Hontiey or Chanzon 10 W 850 nm LED. However, some other embodiments may include a 50 W 850 nm Hontiey or Chanzon LED.

During operation the light source 102 may produce heat that undesirably impacts patient comfort (e.g., burning the skin). The device 100 may include one or more thermal management systems to help manage excess heat. For example, illustrative embodiments may include a heat sink 19 coupled with the non-light emitting surface of the light source 102. The heat sink 19 may have fins to enhance heat transfer. Alternatively, or additionally, a heat pipe may be coupled with the light emitter 102. Some embodiments may include a fan 219 configured to convectively cool the heat sink 19 and/or the heat pipe. The fan 219 may be mounted to the housing 118 via a fan mount 128. The housing 118 may also include air vents 126 to assist with air circulation and cooling. Other thermal management systems that may be used with illustrative embodiments are described, for example, with reference to FIGS. 43-64, below.

In some embodiments, the device 100 has the reflector 106 (e.g., the portion of the material 116 that reflects light towards the brain) at or near the distal end 130. The reflector 106 is configured to change a direction of the NIR light towards the frontal lobe of the patient. For example, the reflector 106 may redirect the light towards the orbitofrontal cortex and/or away from the back of the patient's eye. To that end, the light guide 104 may have an opening and/or a NIR light transparent window through which the NIR light exits the light guide 104. In some embodiments, the reflector 106 may be a mirror (e.g., coupled to the light guide 104 or another portion of the device 100). Alternatively, the reflector 106 may be an exposed inner surface of the material 116. For example, the reflector 106 may be an inner surface of the aluminum coating. In various embodiments, the reflector 106 has a reflectance of at least 80% for NIR light and/or red light. Furthermore, in some embodiments, the reflector 106 may have a reflectance of at least 90%, at least 93%, at least 95%, or at least 99%, for NIR light and/or red light.

Figure 31A:
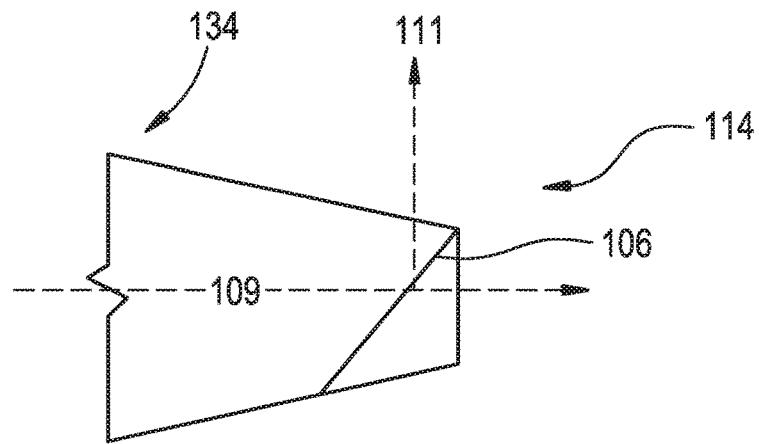
FIGS. 31A-31C schematically show variations of the tip of the light guide in accordance with illustrative embodiments of the invention.
Figure 31B:
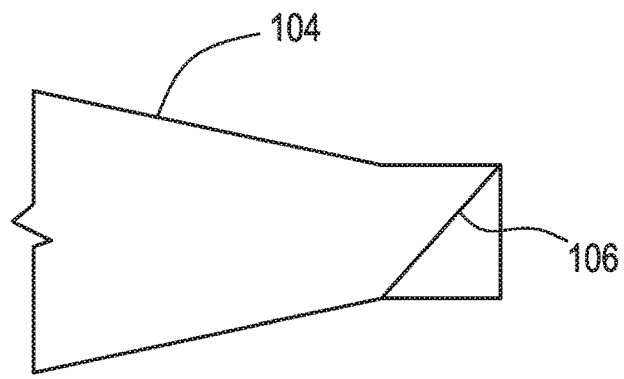

FIGS. 31A-31B schematically show variations of the tip 134 of the light guide 104 in accordance with illustrative embodiments of the invention. For illustration purposes, the light is shown as travelling generally towards the distal end 114 of the light guide 104 in a first direction 109. For ease of discussion, the first direction 109 is shown as a straight line along the longitudinal axis. However, it should be understood that in illustrative embodiments the light may not travel in a collimated line (e.g., the light may reflect off the inner surface of the material 116 as it travels along the guide 104). Thus, while the light is shown as travelling in a single collimated line, it should be understood that light may be travelling in multiple parallel and non-parallel paths. Regardless of the travel path of the light, the guide 104 is configured such that at least some of the light contacts the reflector 106 in a first direction 109 and is reflected in a second direction 111 towards the frontal lobe of the patient's brain, preferably the orbito-frontal cortex. In a similar manner, although the second direction 111 is shown as being a single line that is perpendicular to the first direction 109, this is merely for ease of discussion. A person of skill in the art understands how light reflects off of the reflector 106 (e.g., depending on the angle of incidence, etc.) and can adjust the angle of the reflector 106 as desired.

As shown in FIG. 31A, the reflector 106 redirects the light from the first direction 109 towards the second direction 111. During use, when the device 100 is positioned between the patient's eyelid and orbital bone, the second direction 111 is generally towards the orbito-frontal cortex. Thus, a thin reflector 106 may be cast inside the acrylic guide 104 at an angle configured to direct light towards the top surface. While the device 100 may be oriented in a number of directions, for discussion purposes, orientations such as "top" or "bottom" of the device are with reference to the patient when the device is in use. As shown in FIG. 31A, the end of the light guide 104 may have a frustoconical shape.

Figure 31C:
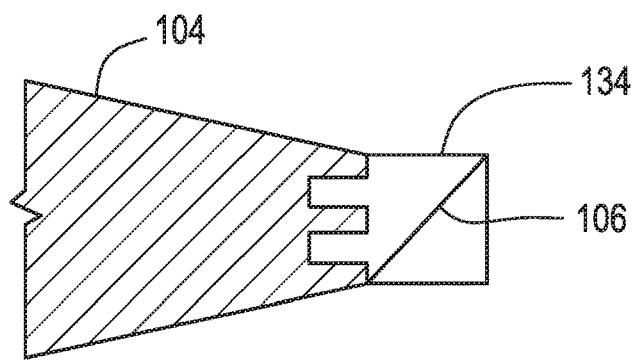

FIG. 31B schematically shows an alternative embodiment of the light guide 104 having an integral distal nosepiece with the reflector 106 inside the nosepiece. FIG. 31C shows an alternative embodiment where the extruded tip 134 with the reflector 106 is a separate component that mates with (e.g., plugs into) the end of the light guide 104. Advantages of the mateable tip 134 include easy replacement (e.g., for different patients), and also for ease of alterations in reflector 106 angle relative to the longitudinal axis.

The reflector 106 can be formed from a portion of NIR reflective metal, and/or NIR reflective coated metal or plastic. In some embodiments, the reflector 106 is positioned in a straight extruded tip. This provides the advantage of minimizing internal reflectance at the light guide-air interface.

Figure 32A:
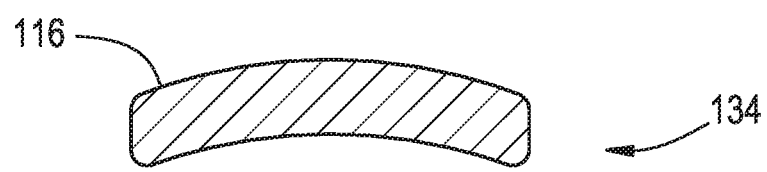
FIGS. 32A and 32B schematically shows a cross section of the tip of the light guide in accordance with illustrative embodiments of the invention.
Figure 32B:
Figure 33A:
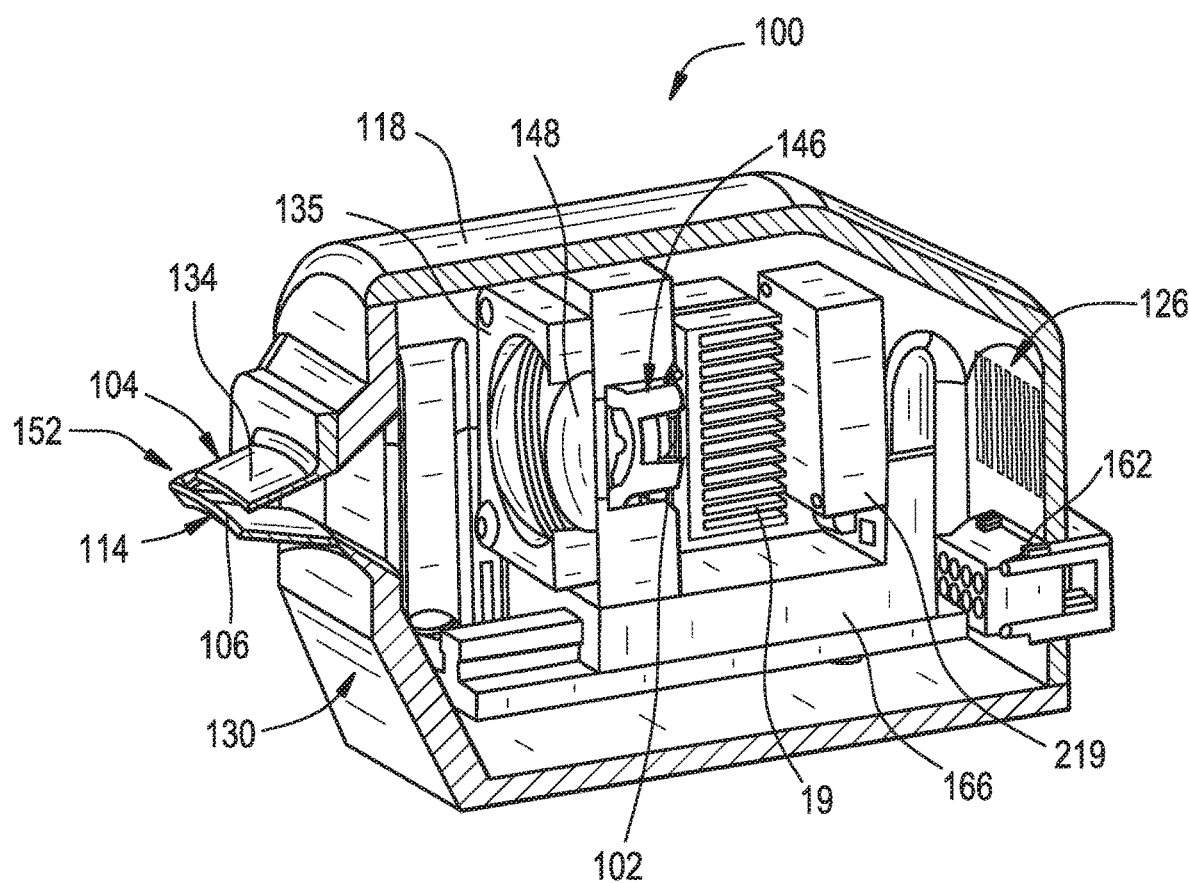
FIGS. 33A and 33B schematically shows an alternative embodiment of the device in accordance with illustrative embodiments of the invention.

FIGS. 32A and 32B schematically shows a cross section of the tip 134 of the light guide 104 in accordance with illustrative embodiments of the invention. In some embodiments, the tip 134 has a substantially concavo-convex shape to fit the curvature of the eye. This shape may improve patient comfort and the optical interface. FIG. 32A schematically shows a solid light guide 104 having a thin coating material 116 configured to cause total internal reflection. FIG. 32B schematically shows a hollow light guide 104, discussed with reference to FIG. 33, below.

FIG. 33 schematically shows an alternative embodiment of the device 100 in accordance with illustrative embodiments of the invention. The device 100 shown in FIG. 33 leverages a projection system that focuses light on the reflector 106 of the light guide 104. Some NIR light sources 102, such as LEDs, emit radiant light in a divergent beam. Accordingly, illustrative embodiments may include an optics mount 135 that orients a focusing element 148 (also referred to as a lens 148) in front of the NIR light source 102 to focus the light beam.

The device 100 has a hollow light guide 104 with the reflector 106 configured to redirect light emitted by the light source 102 (e.g., an LED array). As discussed further below, illustrative embodiments additionally contain optics that provide a number of advantages, including increasing the net effective dosage of NIR light that reaches the brain. Illustrative embodiments increase the net effective NIR light that reaches the brain while remaining within maximum permissible exposure limits. To that end, the device 100 may include a collimator 146 and an optic 148 configured to focus the NIR light to increase the effective amount of light that reaches the brain without surpassing the permissible exposure limit.

The collimator 146 is configured to receive and collimate the NIR light emitted by the light emitter 102. Typically, when the light is emitted by the source 102, it spreads into a wide cone. By positioning the collimator 146 distal to the light emitting surface, the collimator 146 collects the light beams and collimates them after they are emitted. In various embodiments the collimator 146 may be, for example, a parabolic mirror, an ellipsoidal mirror, a Fresnel lens, and/or a convex lens. Preferably, the collimator 146 is configured to cause total internal reflection.

To further enhance the amount of NIR light that reaches the brain, illustrative embodiments may include a focusing optic 148, such as a cylindrical lens, configured to focus the NIR light. In some embodiments, the optic 148 may be positioned distal to the collimator 146 (e.g., with or without an air gap between the collimator 146 and the optic 148). Accordingly, the optic 148 may focus collimated light. However, in some other embodiments, the device 100 may include the optic 148 without the collimator 146, or vice-versa. Thus, in some embodiments, the optic 148 may focus uncollimated light.

In illustrative embodiments, the focusing optic 148 focuses the light in the first direction 109 towards the reflector 106. Thus, a complete light guide 104 may not be necessary (e.g., because the light is not diffusively spreading). Accordingly, illustrative embodiments may merely include the tip 134 of the light guide 104. The focusing optic 148 may focus the NIR light towards the reflector 106. Indeed, some embodiments may include no light guide 104 at all, and instead may merely have the reflector 106 (e.g., coupled with the housing 118 via a mechanical support).

Figure 34A:
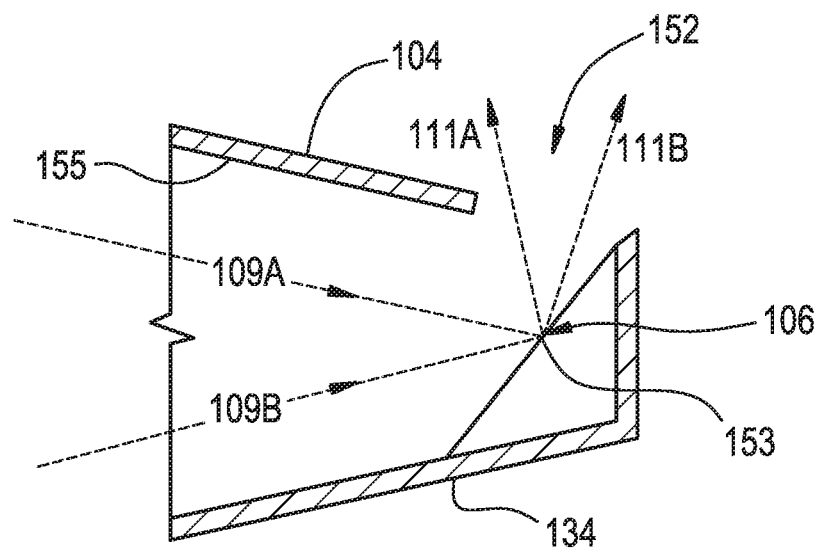
FIG. 34A schematically shows the reflector changing the direction of a focused light beam traveling in a first direction.

FIG. 34A schematically shows the reflector 106 changing the direction of a focused light beam traveling in a first direction 109A and 109B. The reflector may be angled with respect to a longitudinal axis of the light pipe 104. As known by those of skill in the art, a focused light beam has a focal point 153 at a particular focal length. As shown in FIG. 34, the focal point coincides with the surface of the reflector 106. However, as will be discussed further below with reference to FIG. 35B, illustrative embodiments may have the focal point 153 proximal or distal to the reflector 106.

The light is shown as traveling the first direction 109A and 109B. When the focused light contacts the reflector 106, the light is reflected towards the second direction 111A and 111B, respectively. The light exits the light guide 104 through the opening 152. During use, the tip 134 is positioned in the periorbital space, and the opening 152 faces up towards the patient's brain. Accordingly, illustrative embodiments are configured such that the focused beam is redirected by the reflector 106 to transmit light transorbitally towards the patient's brain. As an additional advantage, the tip 134 may shield the eye from light exposure (e.g., backscatter).

In some embodiments, the hollow light guide 104 is formed of metal and may have a polished inner face 155 that acts as the reflector 106. The light travels in the second direction 111 towards the patient's brain through the opening 152 in the light guide 104. Instead of the opening 152, some embodiments may include an NIR transparent window. In some embodiments, the hollow light guide 104 may be purely structural, merely supporting the reflector 106 at its tip 134. In some embodiments, custom focusing optics 148 may be used to produce an output light spot shape that matches the geometry of the reflector 106, as discussed with reference to FIGS. 37-38.

Figure 34B:
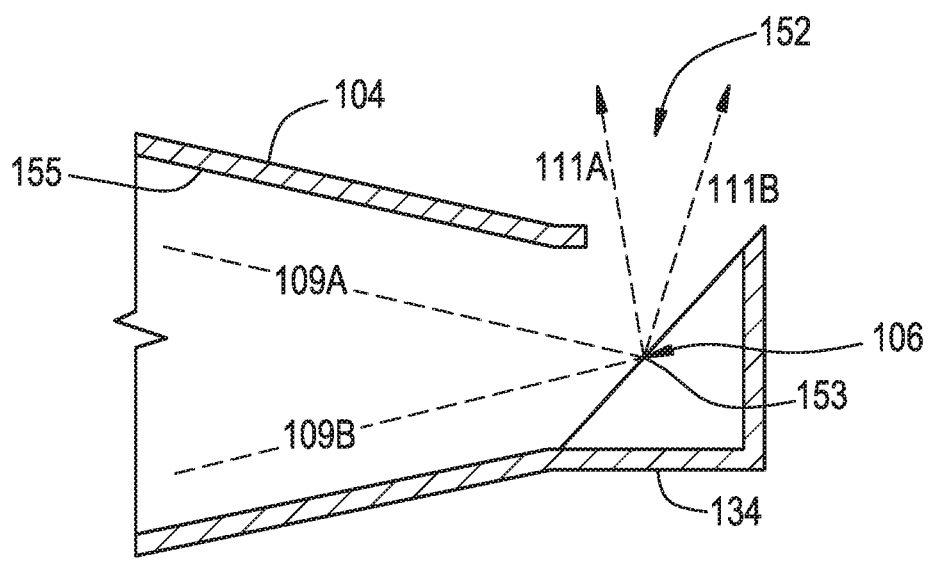
FIG. 34B schematically shows an alternative embodiment of the tip of FIG. 34A.
Figure 35A:
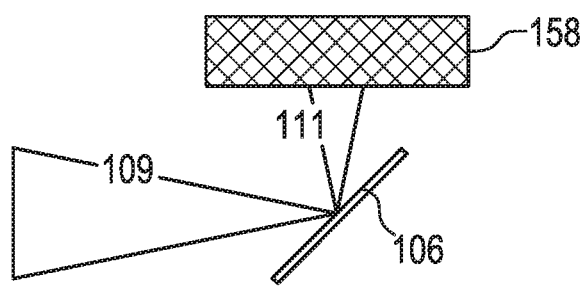
FIGS. 35A-35D schematically show the reflector changing the direction of the light as a function of various focal lengths.
Figure 35B:
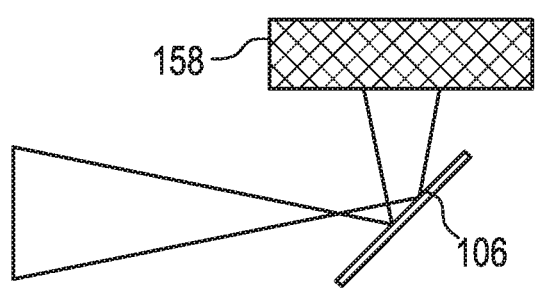
Figure 35C:
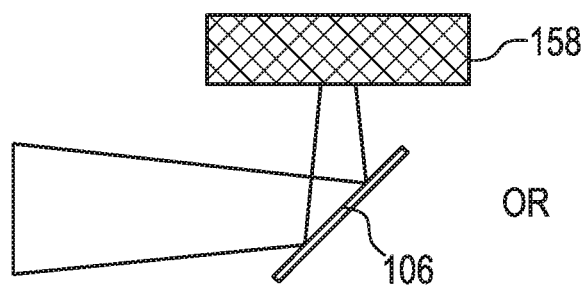
Figure 35D:
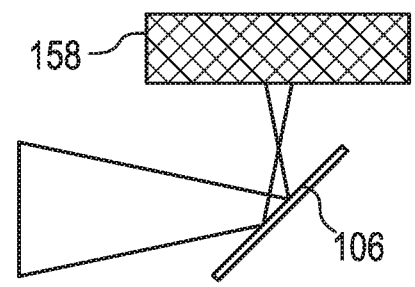

FIG. 34B schematically shows an alternative embodiment of the tip 134 of FIG. 34A. The reflector 106 is in an extended area of the light pipe 104. This allows the light to focus tighter before being reflected, thereby allowing more light to reach the opening 152 and/or providing for a larger opening 152. It also serves to reflect the light upward into the orbit to protect the eye and maximize the amount of light reaching the prefrontal cortex.

In illustrative embodiments, the reflector 106 is angled relative to a longitudinal axis of the hollow light pipe 104. In some embodiments, the reflector 106 is angled such that the light exits the window and/or opening 152 at an angle substantially perpendicular to the longitudinal axis of the light pipe.

The tip 134 of the hollow light pipe 104 may be formed from a light reflective material. The tip 134 has an upper wall, a lower wall, and opposing side walls connecting the upper and lower walls. Preferably, the lower and upper walls of a distal end of the tip 134 form a substantially concavo-convex shape, wherein the upper wall has the opening 152

Figure 33B:
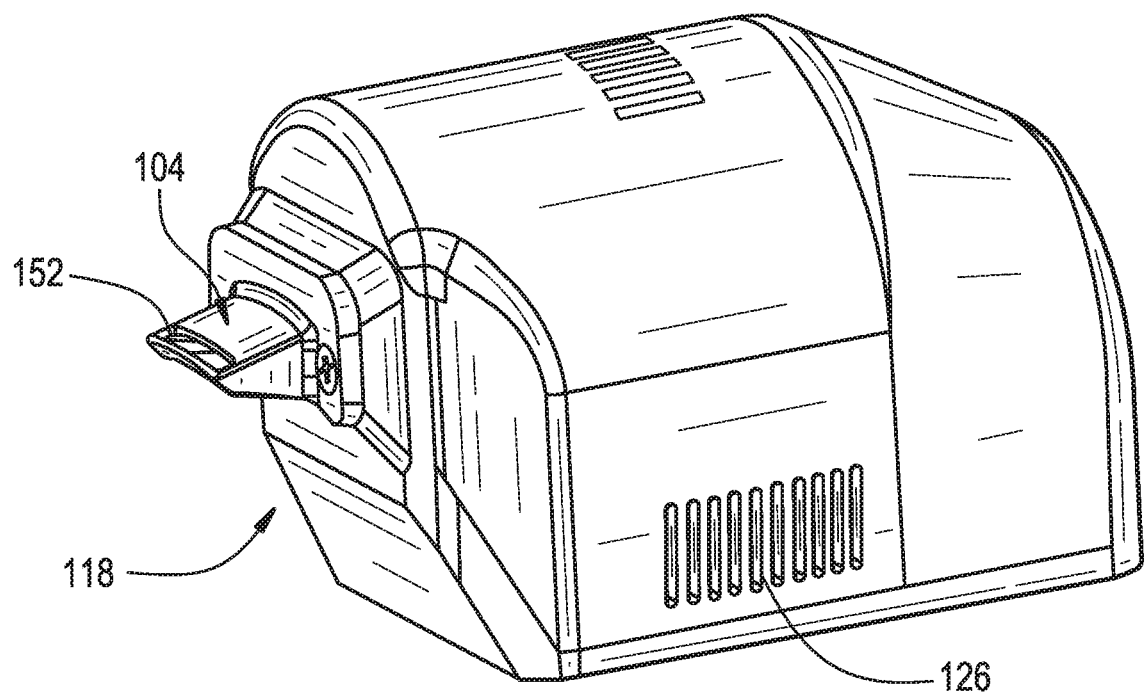

FIGS. 35A-35D schematically show the reflector 106 changing the direction of the light as a function of various focal lengths. Beam power density on the skin is related to the focal length of the optics. In some embodiments, such as in FIG. 33A, the device 100 is configured so that the focal length is equal to the distance to the reflector 106. As a result, the light beam is divergent upon incidence with the skin 158. In some other embodiments, as shown in FIG. 33B, the device 100 is configured so that the focal length is shorter than the distance to the reflector 106. As a result, the beam is also divergent, but of a lower power density relative to FIG. 33A upon incidence with the skin 158. In some other embodiments, such as in FIGS. 35C and 35D, the device 100 is configured so that the focal length is greater than the distance to the reflector 106. The beam may be convergent (FIG. 33C) or divergent (FIG. 33D) upon incidence with the skin 158 and at a higher power density relative to the conditions shown in FIG. 35A-35B.

There is, however, an operational risk associated with using a convergent light source. If the device 100 is held at such a length outside of the intended operating parameters, such that the focal point is on or close to the skin 158 surface, the high power density can damage the skin 158. The penetration depth of light in tissue is inversely related to beam divergence and directly related to power density. In the case of the three focal length conditions, the penetration depth may increase as the focal length of the optics becomes greater than the distance to the reflector 106. The desirability of each embodiment lends to the depth and desired irradiance of the target neural tissue, as well as operational safety.

While the embodiments shown in FIGS. 35A-35D show the light as converging or diverging after reflecting from the reflector 106, some embodiments may include a collimator 146 configured to collimate the light after it is reflected (e.g., on the distal tip 134 after the light changes direction on the reflector 106). The collimator 146 provides the additional advantage of promoting uniformity while also increasing the penetration depth of the light spot that would otherwise be divergent or convergent upon incidence with the skin 158. In some embodiments, the device 100 has a plurality of the collimators 146 (e.g., proximal of focusing optic 148 and on the distal tip 134 in the path of the second direction 111).

Figure 36A:
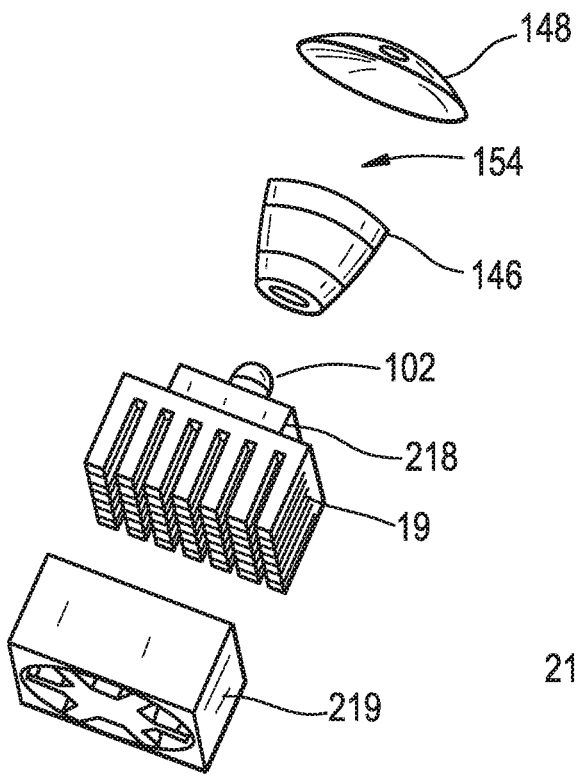
FIG. 36A schematically shows an exploded side view of internal components of the device in accordance with illustrative embodiments of the invention.
Figure 36B:
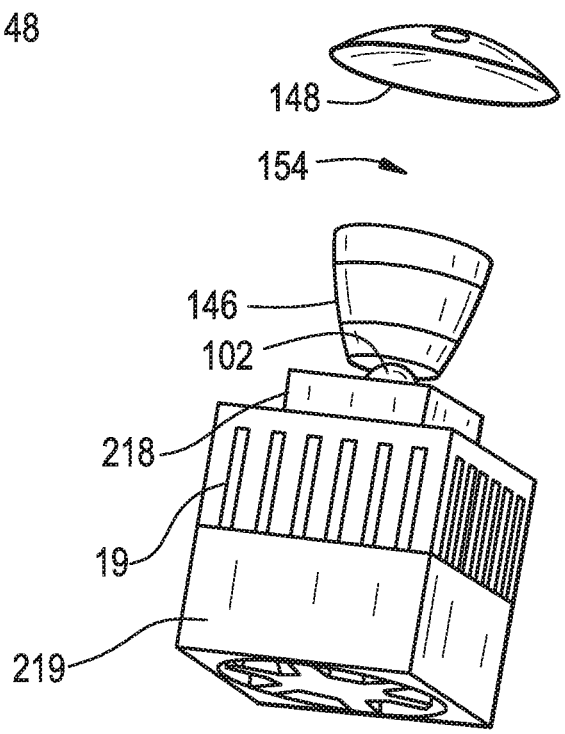
FIG. 36B schematically shows an assembled view of FIG. 36A.

FIG. 36A schematically shows an exploded side view of internal components of the device 100 in accordance with illustrative embodiments of the invention. FIG. 36B schematically shows an assembled view of FIG. 36A. As described previously, the device 100 may include the fan 219 configured to cool the heat sink 19. As shown, the heat sink 19 may be coupled with the hot side of the peltier chip 218 (described previously), while the cool side is coupled with the light source 102. The collimator 146 may be positioned to receive light emitted by the source 102. The focusing optic 148 then receives the collimated light and focuses it to produce an output spot shape.

Focusing optics 148 can be leveraged to control the output of the light source 102 to the desired uniformity, spot shape, and size. Optics 148 can also improve power efficiency by controlling the path of divergent light from a light source 102. To collimate the divergent beam of the light source 102, a Total Internal Reflection (TIR) collimator 146 is placed at the interface of the light source 102. In the instances where a round spot is desired, the spherical lens optic 148 shown in FIGS. 36A-36B may be used to both focus and maintain the round spot output from the TIR collimator 146. Illustrative embodiments include an air gap 154 between the collimator 146 and the optic 148 to allow the light to refract in the intended path of the collimator 146, prior to passing through the focusing optic 148. As an additional advantage, the air gap 154 allows the optic 148 to remain some distance away from the heat-generating light source 102.

Figure 37:
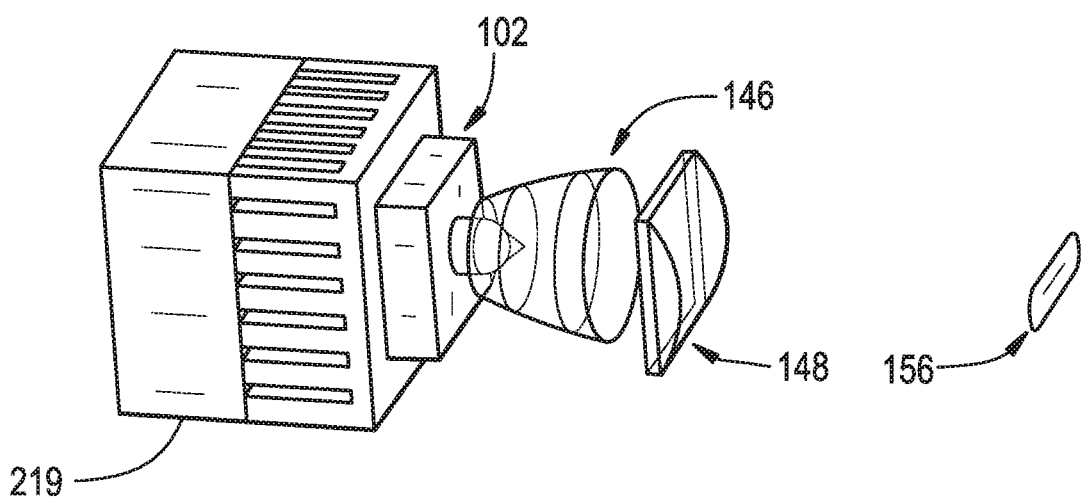
FIG. 37 schematically shows an alternative embodiment of the focusing optic in accordance with illustrative embodiments of the invention.

FIG. 37 schematically shows an alternative embodiment of the focusing optic 148 in accordance with illustrative embodiments of the invention. In the figure, the focusing optic 148 is a cylindrical optic 148, as opposed to a semi-spherical optic 148. A cylindrical optic 148 is preferred where a linear or racetrack-shaped output spot 156 is desired. Similar to the focusing optic 148 described previously, the cylindrical optic 148 (e.g., a cylindrical lens) may be positioned distally of the collimator 146. Additionally, the air gap 154 may be between the collimator 146 and the optic 148.

Figure 38:
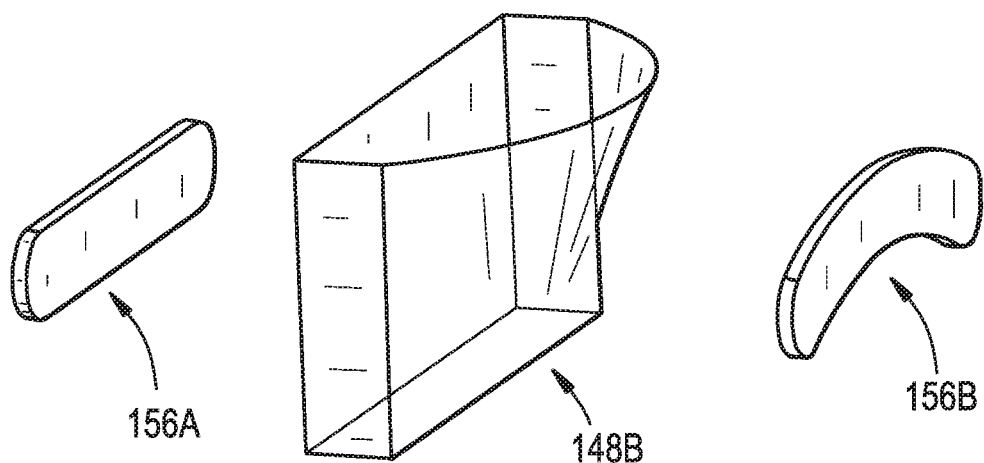
FIG. 38 schematically shows a second focusing optic configured to produce an alternative output spot shape.

FIG. 38 schematically shows a second focusing optic 148B configured to produce an alternative output spot 156 shape. As shown, the optic 148B may have a unique shape. Some embodiments may desire a unique output spot 156 shape. For example, the desired output shape 156 may be an arc, which is intended to match the curvature of the periorbital space above the eye. Some embodiments of the device 100 achieve the arc output spot shape 156 by adding an additional optic 148B after the first optic 148 (e.g., after the cylindrical lens not shown in this figure). The second optic 148B uses refraction to shift the light path away from the horizontal at greater magnitudes for rays at the center of the linear spot. Accordingly, the second optic 148B receives the first output spot shape 156A, and outputs a second arc-shaped spot 156B.

Figure 39A:
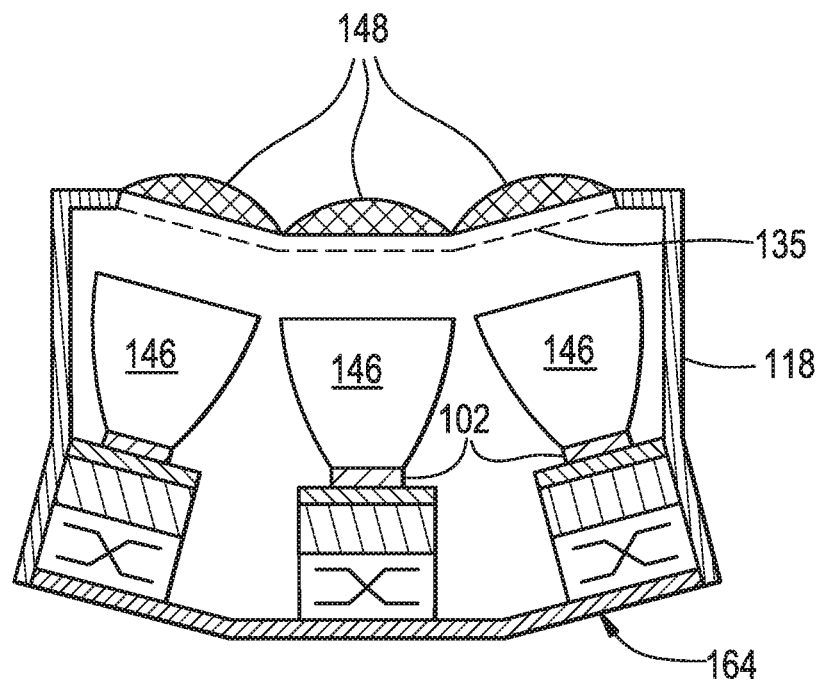
FIGS. 39A-39B schematically show view of assembled internal components of an alternative embodiment of the device in accordance with illustrative embodiments of the invention.
Figure 39B:
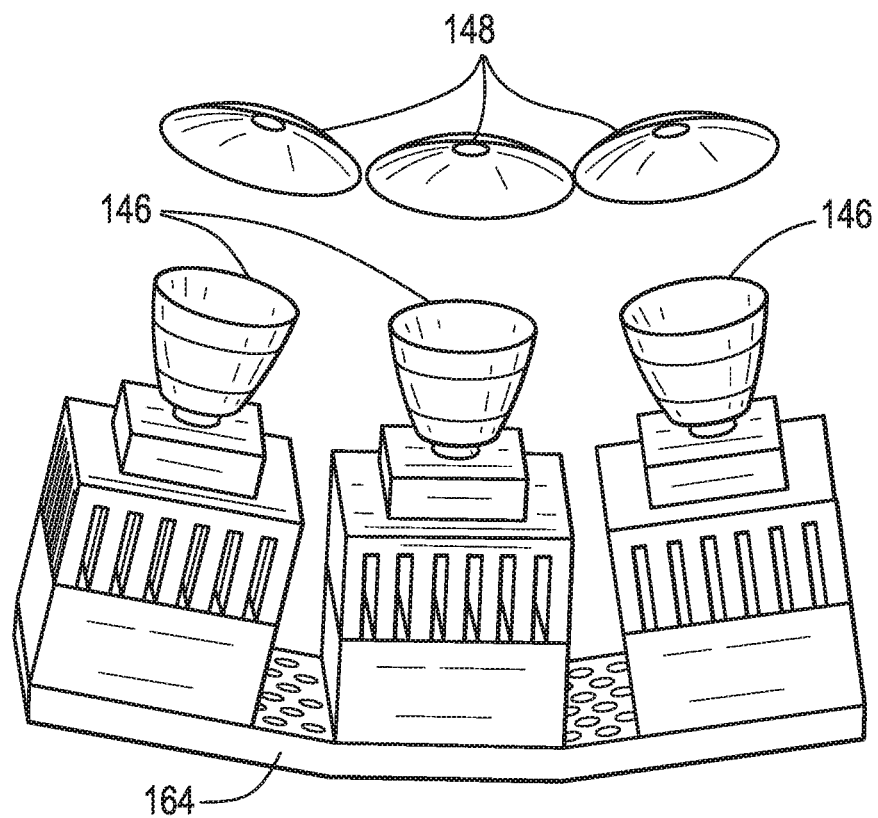

FIGS. 39A-39B schematically show view of assembled internal components of an alternative embodiment of the device 100 in accordance with illustrative embodiments of the invention. As shown, some embodiments may use a plurality of light sources 102, collimators 146, and/or focusing lenses 148. The plurality of assembled components may share a common ventilation mount 164 that acts to focus all three arrays towards the intended output spot. Such an arrangement may provide for increased light intensity at the focal spot while reducing the amount of intensity produced by any particular light source 102. The mount 164 allows the bottom side of each assembly to ventilate, but secures the units in such a way that they are pointing at a similar focal spot location with a given focal length (e.g., preferably the same focal length). Additionally, the housing 118 may protect the components and keep the lenses 148 in the correct location and orientation.

Figure 40:
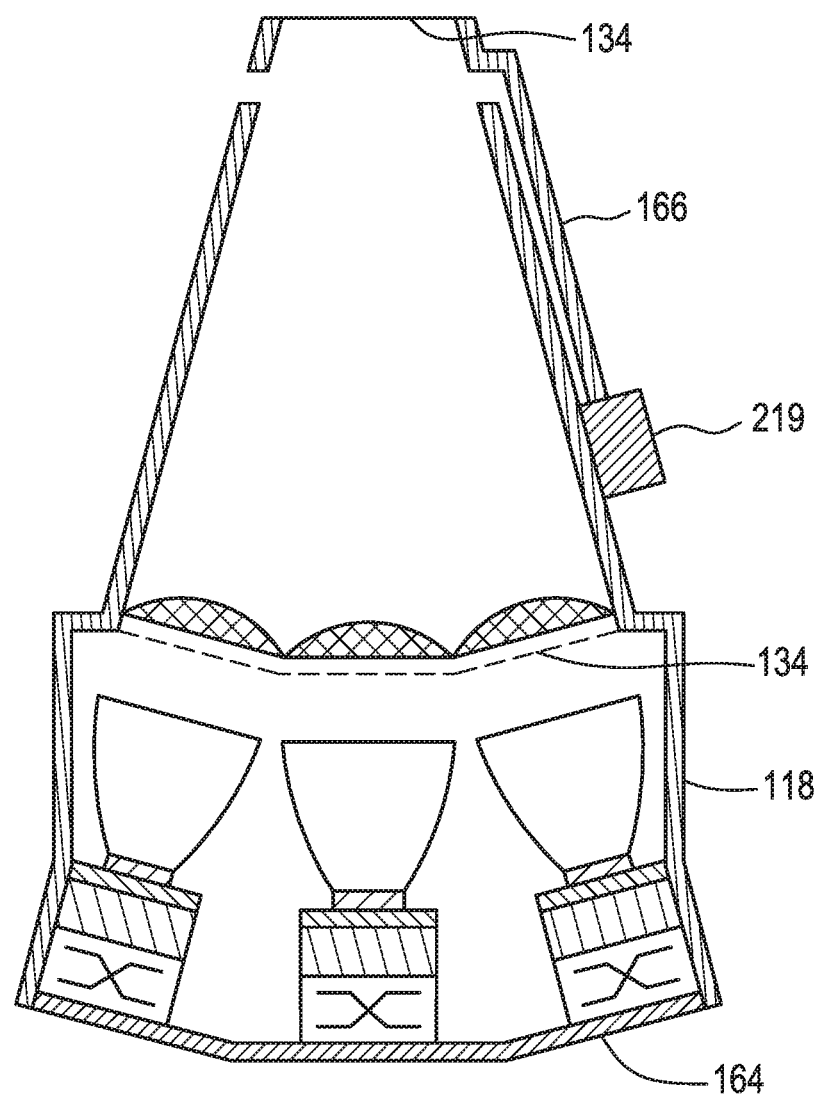
FIG. 40 schematically shows the triple emitter, the collimator, and the focusing lens arrangement of FIGS. 39A-39B with the light guide in accordance with illustrative embodiments of the invention.

FIG. 40 schematically shows the triple emitter 102, the collimator 146, and the focusing lens 148 arrangement of FIGS. 39A-39B with the light guide 104 in accordance with illustrative embodiments of the invention. The triple lensed arrangement includes an added fan 219 or pump system and the light guide 104. The shape of the housing 118 is configured to allow the light from all three systems to converge at the distal end of the tip 134 in order to maximize power density at the desired output location. The ventilation system allows for a pump or fan 219 to direct fluid flow down the side channel 166 and out into the body of the device 100. On the opposite side is an exhaust vent for the warmed air to escape out of. The cool fluid helps mitigate temperature rise at the targeted area produced by the thermalization of light. In some embodiments, the cooling method helps cool the LED chips. Depending on the cooling ability of the fan/pump system, the flow could reach down to the LEDs where the fluid is exhausted. The system cools both using conduction and convection to cool the eyelid and potentially the LED.

Figure 41A:
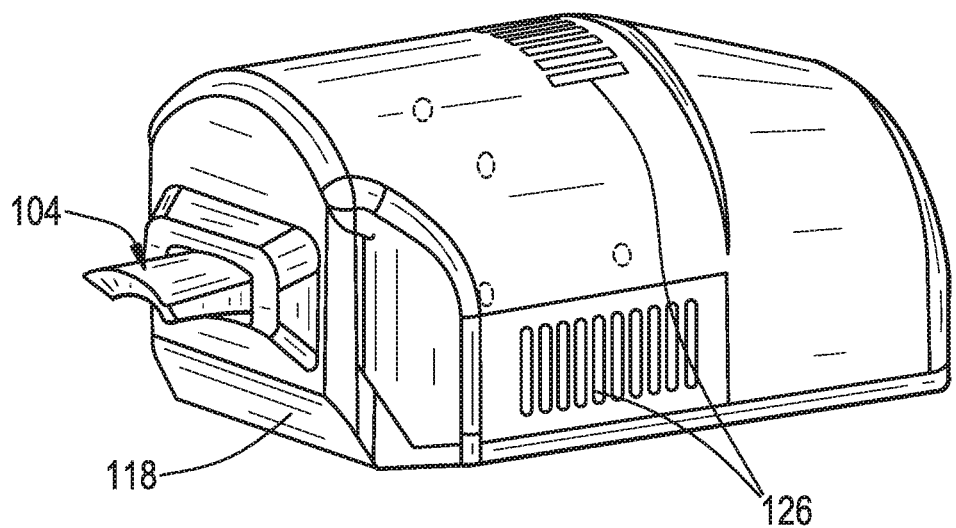
FIGS. 41A-41B schematically show an alternative embodiment of the device in accordance with illustrative embodiments of the invention.
Figure 41B:
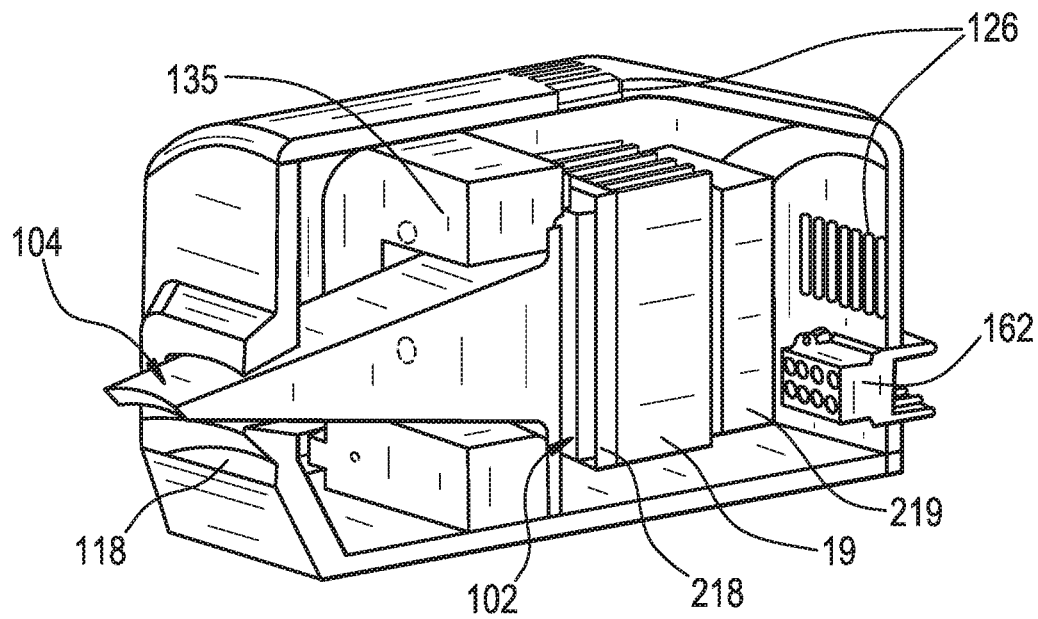

FIGS. 41A-41B schematically show an alternative embodiment of the device 100 in accordance with illustrative embodiments of the invention. The light source 102 may be, for example, a Hontiey or Chanzon low 850 nm LED. The device 100 is similar to the device 100 shown in FIGS. 30A-30B1, with the exception that a thermoelectric cooler 218 (TEC) mounts to the non-light emitting surface of the light source 102 to assist with increased heat transfer between the light source 102 and the heat sink 19. Additionally, illustrative embodiments may include a cable harness 162 on the rear face of the housing 118 that leads to a power controller input. The controller may enable pulse width modulation of the LED light source 102 and/or power to the fan 219.

FIG. 42 shows a process 400 of treating the brain in accordance with illustrative embodiments of the invention. It should be noted that this method is substantially simplified from a longer process that may normally be used. Accordingly, the method shown in FIG. 42 may have many other steps that those skilled in the art likely would use. In addition, some of the steps may be performed in a different order than that shown, or at the same time. Furthermore, some of these steps may be optional in some embodiments. For example, steps 424 and 426 may be optional in some embodiments. Accordingly, the process 42 is merely exemplary of one process in accordance with illustrative embodiments of the invention. Those skilled in the art therefore can modify the process as appropriate.

The process 400 begins at step 420, which positions the device 100 in the peri-orbital space of the patient. Specifically, the tip 134 at the distal end 130 of the housing 118 is positioned between the eye lid and orbital bone. To that end, the tip 134 preferably has a substantially concavo-convex shape to better fit within the concavo-convex cavity between the eye and the orbital bone and to improve compliance and optical interface. Additionally, the tip 134 is thin to assist with better positioning within the small periorbital space. Accordingly, the tip 134 may have a thickness of less than 5 mm, less than 3 mm, or less than 2 mm. These relatively thin sections allow for fairly comfortable distal (posterior) insertion of the tip 134 into the region between the eye and the eye socket to a distance of at least 8 mm, at least 10 mm, or at least 15 mm. Additionally, or alternatively, some embodiments may position the tip 134 into the orbital socket at most about 25 mm, or at most about 20 mm. In some embodiments, the substantially concavo-convex tip 134 preferably has a thickness of less than 5 mm at an insertion depth of about 20 mm from the distal end 130, thereby keeping the substantial majority of the light pipe 104 that enters the eye socket relatively thin. In some embodiments, a flange on the hollow light guide 104 connects to the housing 118 at 15 mm from the distal point of the tip 134, limiting insertion depth into the orbit. In some embodiments, this distance is in the range of 5 mm to 20 mm.

When the tip 134 is positioned in the periorbital space, an NIR light transparent window and/or an opening 152 is preferably facing upward towards the brain, such that any light that escapes the light guide 104 is directed towards the brain. To that end, the tip 134 has a reflector 106 configured to change the direction of light pulsed by the light source 102 from the first direction 109 to the second direction 111.

In some embodiments, light thermalization at the skin 158 may limit the amount of light that can be pulsed towards the brain is the biggest barrier in the development of this device. In addition to the various thermal management systems described through the application, another attempt to mitigate the thermalization may include applying a cooling gel at the eyelid in contact with the distal tip 134 of the device 100. For example, menthol or lidocaine rub may be utilized to lower the temperature at the eyelid, and/or to provide a cooling sensation to the eyelid and give a tactile stimulus to the patient.

The process 400 then proceeds to step 422, which pulses light from the light source 102. As described previously, the light source 102 is configured to pulse NIR light to treat the brain. Some embodiments may have a plurality of light sources 102 (e.g., as shown in FIGS. 39A and 39B). Additionally, one or more of the light sources 102 may pulse red light and/or short-wavelength infrared light. Furthermore, the light source 102 may be a laser and/or an LED.

Because the light source 102 tends to run hot after use, the device 100 includes a thermal management system, such as a heat sink 19 and/or fan 219 attached to the back face of the LED to maintain the emitter 102 temperature at the recommended, safe operating point. This ensures quality and consistency of light throughout the treatment, as well as prevents the LED from operational damage. Air vents 126 are built into the housing 118 adjacent to the intake face of the fan 219 and the sides of the heat sink 19 for thermal exhaust. Lastly, a cable harness 162 on the posterior face of the housing 118 leads to a power controller input. The controller enables pulse width modulation input to the light source.

The process 400 then proceeds to step 424, which collimates the light emitted by the light source 102. To that end, the collimator 146 is positioned distally of the light source 102, such that it receives all or substantially all of the emitted light, and collimates it. In illustrative embodiments, the collimator 146 assists with increasing the energy density of the emitted light that ultimately reaches the brain. The collimator may be, for example, a TIR optic.

The process 400 then proceeds to step 426, which focuses the collimated light by passing it through the focusing optic 148. The focusing optic 148 may be, for example, a spherical lens used to focus the beam. Additionally, or alternatively, the focusing optic 148 may be a cylindrical lens, or a custom shaped lens. Furthermore, some embodiments may use a plurality of lenses in series to produce a custom output spot 156 shape (as shown in FIG. 38).

Focusing the light results in a focal point for the light. In some embodiments, the device 100 is configured such that the focusing optic 148 has a focal point at the distal tip 134 of the light guide 104. For example, the tip 134 may include a hollow metal portion whose inner face is polished to work as a reflector 106 that changes the light path direction. In some other embodiments, however, the focal point may be proximal to, or distal to, the reflector. FIGS. 35A-35D schematically show a variety of focal lengths and how the treatment outcomes are affected by the focal length of the focused light. Furthermore, the optical mount 135 and thermal management components may rest on a linear tuning track 166. This track 166 adjusts the distance between the focal point of the optics 148 and the landing spot 156 on the reflector 106. As previously described, this distance assists with controlling the convergence and power density of light at the skin 158 surface.

The process 400 then proceeds to step 428, which reflects the light towards the brain. To that end, the tip 134 and/or the light guide 134 has a reflector 106 configured to change a direction of the light from the first direction 106 towards the reflector 106 to the second direction 111 towards the brain. In some embodiments, the first direction 109 may be the direction that light is emitted from the source 102. In some other embodiments, the first direction 109 may be the direction that the light comes from prior to reaching the reflector. In some embodiments, the first direction 109 may be the direction of light collimated by the collimator 146 and/or focused 148 by the focusing lens 148. The reflector 106 may be, for example, a mirror, a polished metal surface of the tip 134, and/or the internal surface of an NIR light reflective coating on the solid light guide 104 (e.g., inner surface of material 116 in FIG. 30).

The process 400 then asks, at step 430, whether more light is needed for the treatment. If more light is needed, then the process returns to step 422, where light is pulsed again. Illustrative embodiments dose between 0.1-1.0 $J/cm^2$ across different regions of the orbitofrontal cortex. In some embodiments, the process 400 is repeated until 0.1-10 $J/cm^2$ of light reaches the brain. In some embodiments, the process is repeated at intervals, to allow the device 100 to cool off, and to prevent or reduce the risk that maximum permissible exposure limits are reached for the skin 158 receiving the light. The maximum permissible exposure limit for 850 nm light is approximately 400 $mW/cm^2$ at the skin 158. In some embodiments, a therapeutic dose of emitted light is about 400 $mW/cm^2$, so as to maximize the light reaching the brain without overcoming the maximum permissible exposure limit. In some embodiments, the light may be dosed every 48 hours. In some embodiments, the process may be repeated for three consecutive days, at hours 0, 24, and 48.

If no more light is needed for treatment, then the device 100 is removed from the periorbital space and the process comes to an end. Although step 432 is shown as coming after step 430, it should be understood that in some protocols having an extended wait between dosing (e.g., every 5 minutes or more) the device 100 may be removed from the periorbital space, and simply repositioned at the time of the subsequent dose.

FIG. 43 schematically shows a thermal management system including liquid pressurized gas (LPG) cooling in accordance with illustrative embodiments of the invention. Illustrative embodiments use LPG, such as $CO_2$, $N_2O$, 134a, and/or other common refrigerants. When gas is released from an LPG tank 168, the pressure in the tank 168 drops, and the remaining liquid inside begins to evaporate. The tank 168 and its contents cool due to the spontaneous liquid evaporation.

Illustrative embodiments use the temperature drop of the disposable tank 168 and its contents to cool the non-light emitting surface of the LED light source 102. The tank 168 may be fitted with two brackets: a thermal insulator like rubber to reduce heat exchange on the side opposite of the LED, and a metal, thermally conductive bracket 170 attached to the non-light emitting surface of the LED 200. In some embodiments, the thermally insulating bracket 172 encompasses the majority of the exposed surface area of the tank 168. Heat exchange occurs between the LED light source 102 and the LPG tank 168 through the metal bracket 170.

Compressed air escaping the tank 168 can be leveraged to cool other aspects of the device 100. As more gas is released, the gas cools relative to room temperature when the heat transferred to the tank 168 by the LED is less than that consumed by the phase change in the tank 168. In some embodiments, the cold gas may be used to cool the skin-device interface.

Figure 44A:
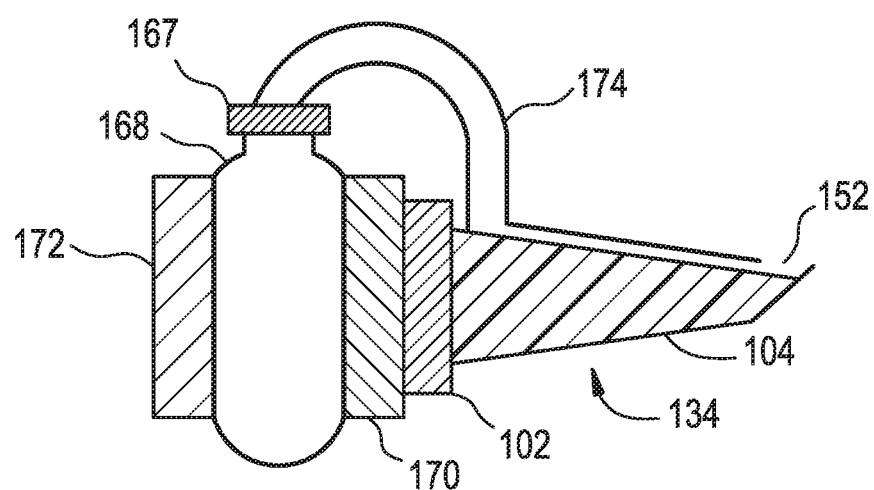
FIG. 44A schematically shows a cross-sectional view of the LPG thermal management system being used with a solid light pipe.

FIG. 44A schematically shows a cross-sectional view of the LPG thermal management system being used with a solid light pipe 104. In FIG. 44A, the cold compressed gas flows at a regulated pressure through a channel on the surface of the solid light pipe 104 towards the distal tip 134. The superior surface of the channel at the distal tip 134 has the opening 152 to allow the cold gas to flow across the skin at the skin-device interface. Ventilation of the gas may occur at the distal tip 134 or through openings at the side of the gas channel. Cooling of the skin hinders and/or prevents temperature rise at the periorbital space caused light thermalization, improving comfort and enabling the use of higher power treatment. Some embodiments include a flow regulator 167.

Figure 44B:
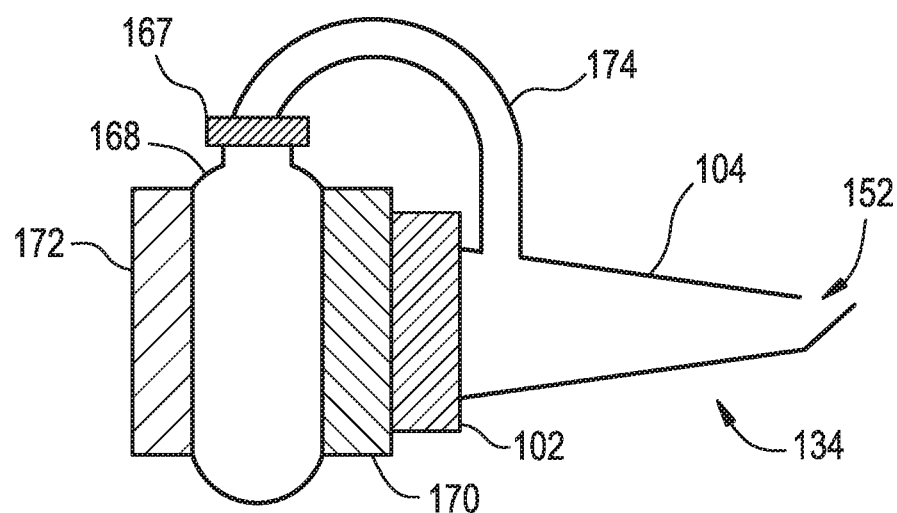
FIG. 44B schematically shows a cross-sectional view of the LPG thermal management system being used with a hollow light pipe.

FIG. 44B schematically shows a cross-sectional view of the LPG thermal management system being used with a hollow light pipe 104. As shown, the circulation of the gas cools both the pipe 104 and the skin 158. While the figure shows that the compressed gas channel 174 connects with the light guide at a proximal portion of the tip 134, in some embodiments, the compressed gas channel may connect to the light guide 104 closer to a distal end of the tip 134.

Figure 45A:
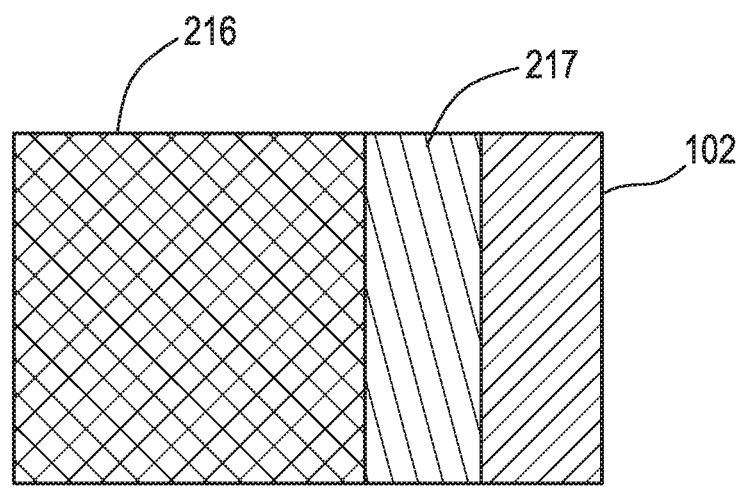
FIG. 45A schematically shows a disposable cooling component in accordance with illustrative embodiments of the invention.

FIG. 45A schematically shows a disposable cooling component in accordance with illustrative embodiments of the invention. As discussed previously, thermal management helps extend the lifespan of the light source 102, as well as the consistency of output power and wavelength. A chemical reaction can be leveraged to cool the light source. Some embodiments of the device 100 leverage an endothermic reaction cartridge on the backside of the light source 102 to maintain operating temperature. FIG. 43 shows the cartridge that cools the LED 200. Heat flows from the LED, through a metal plate backing, then into the cartridge. Some embodiments do not have a metal plate between the LED and cartridge. The plate may both absorb and transfer heat at a desired rate.

Figure 45B:
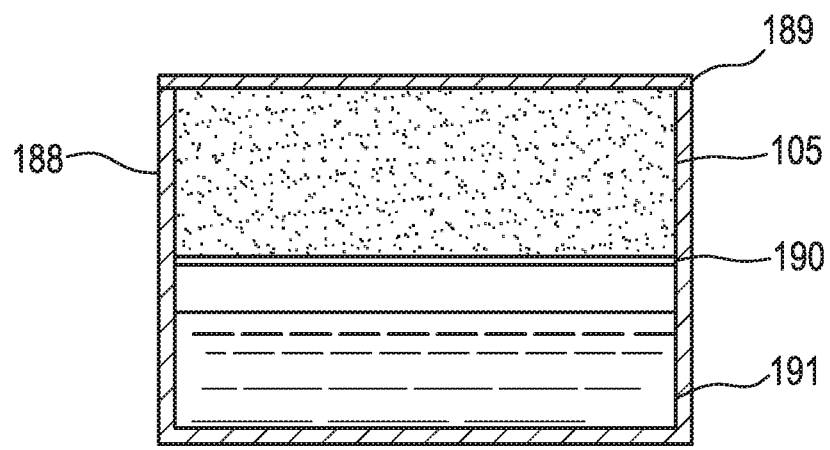
FIG. 45B schematically shows the cartridge of FIG. 45A.

FIG. 45B schematically shows the cartridge of FIG. 45A. The reaction in the cartridge may be caused by dissolution of solid reactant urea or ammonium nitrate in water. As known to those of skill in the art, a similar reaction occurs in cold packs. The cartridge isolates the two reactants until a pressure puncture barrier between the two is broken upon use. Pressure is applied to a flexible seal to puncture the barrier and combine reactants. The cartridge includes at least one metal wall at the interface with the metal plate or LED. The wall may be formed of copper or aluminum. In some embodiments the cartridge is collapsible via the walls or flexible seal to promote the mixing of reactants at the side proximal to the LED.

Figure 46A:
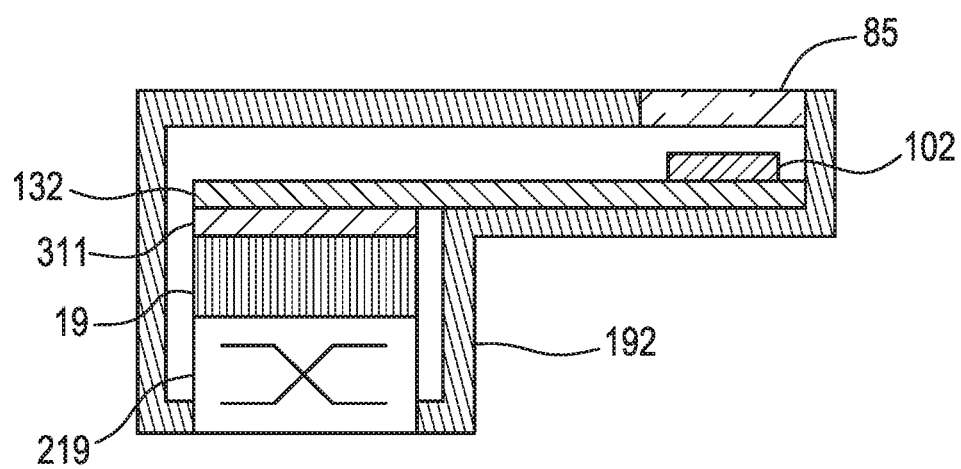
FIGS. 46A-46B schematically shows a thermal management system including a heat pipe in accordance with illustrative embodiments of the invention.
Figure 46B:
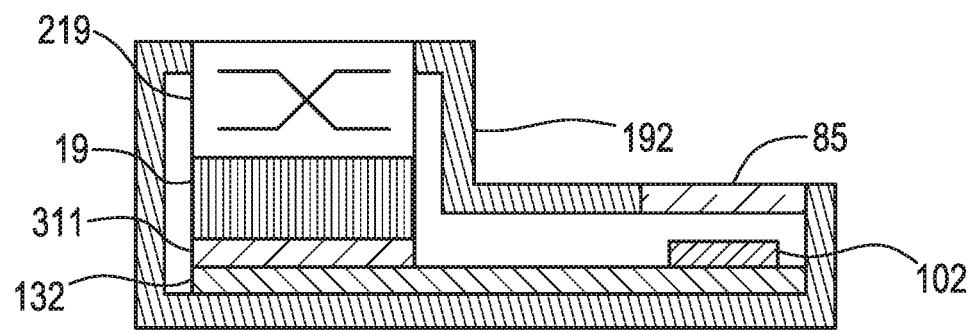

FIGS. 46A-46B schematically shows a thermal management system including a heat pipe in accordance with illustrative embodiments of the invention. The heat pipe may be included in various embodiments of the device 100. The heat pipe designs includes a thermally conductive length of material that preferably contacts the distal end of the LED. This serves as a way to conduct heat away from the hot LED to protect the skin exposed to the distal tip.

FIGS. 46A and 46B show the same cooling mechanisms, just one is the mirror image of the other. In both designs, the LED is just below the transparent window 85. This window 85 serves to thermally isolate the area being irradiated by the LED from the heat generated by the LED. This material could be any transparent thermal insulator (i.e., glass, acrylic, aerogel, etc.). However, some embodiments do not have the window 85. Instead, a collimator and/or focusing optic may be used here instead.

The LED is mounted on a thermally conductive heat pipe configured to wick heat from the hotter evaporative side to the cooler condensing side. Some embodiments could also be used with a typical thermally conductive material like copper. On the cooler side is mounted a Thermoelectric cooling (Peltier) chip. This acts to keep the cool side of the heat pipe cool at all times. The hot side of the TEC is then mounted on a heat sink and fan in order to dissipate heat quickly and efficiently.

Figure 47A:
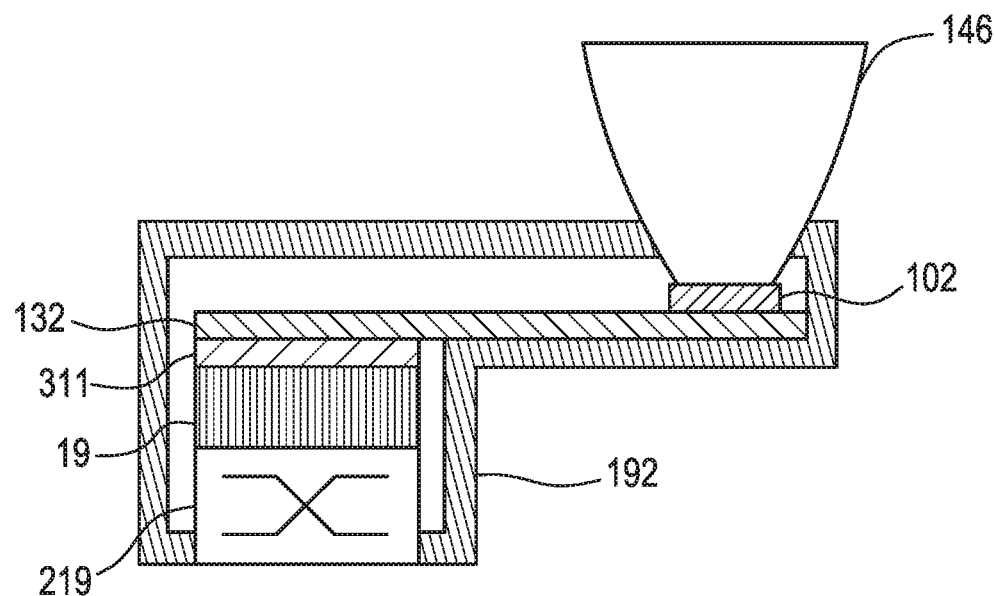
FIGS. 47A-47B schematically show the heat pipe being used with the collimator and the focusing lens in accordance with illustrative embodiments of the invention.
Figure 47B:
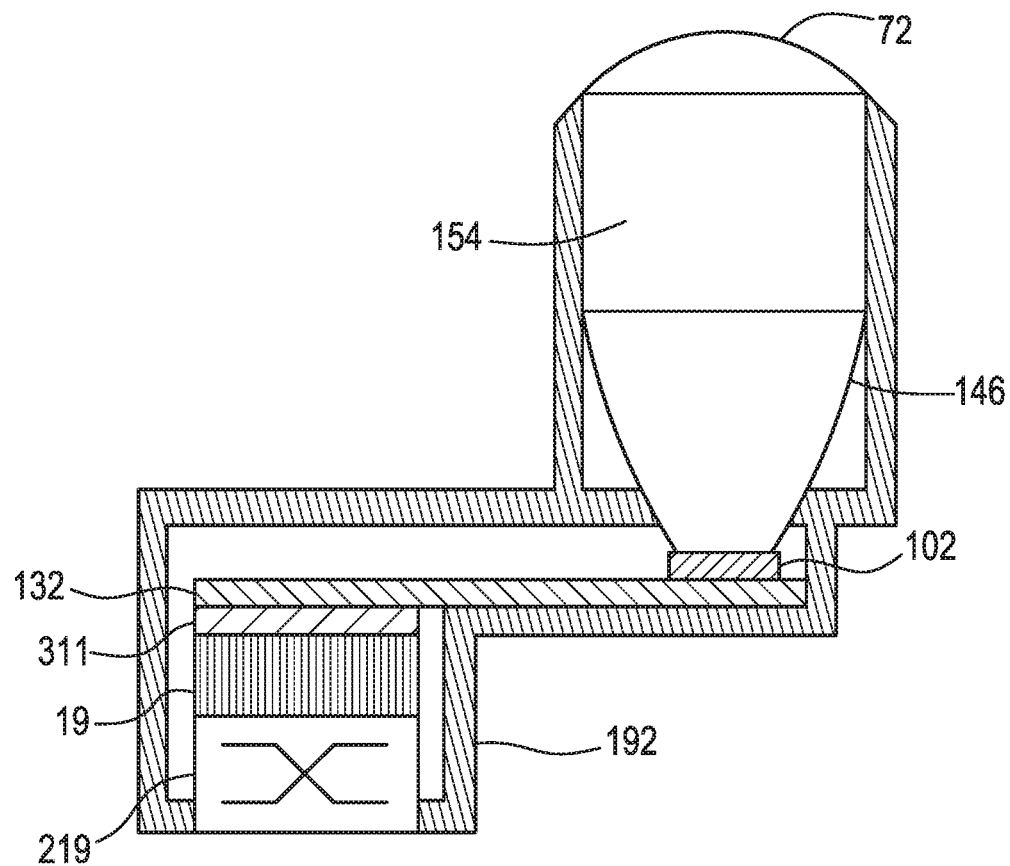

FIGS. 47A-47B schematically show the heat pipe being used with the collimator and the focusing lens in accordance with illustrative embodiments of the invention. These two figures are similar to FIGS. 46A-46B, but include the collimator attachment for the LED. As described previously, the collimator takes the uncollimated light from the LED source 200 and collimates it. This assists with increase the penetration depth achieved by the LED light. Collimated light shown to penetrate deeper into tissue than uncollimated light of the equal power. Additionally, by maximizing the power density at the point of delivery, a lower electrical power could be used allowing for less demand on the cooling system. Aside from the collimator, the system is the same. The heat dissipation system uses a Peltier module, heat sink, and fan to cool the condensing side of the heat pipe. The second image shows a lens on the collimator while the first does not. The collimator requires space between it and any lens so a buffer space is created by making the frame support the lens with a small air gap. Depending on the LED chosen and the desired spot size on the skin decided to be optimal, a Lens may or may not be necessary.

Figure 48A:
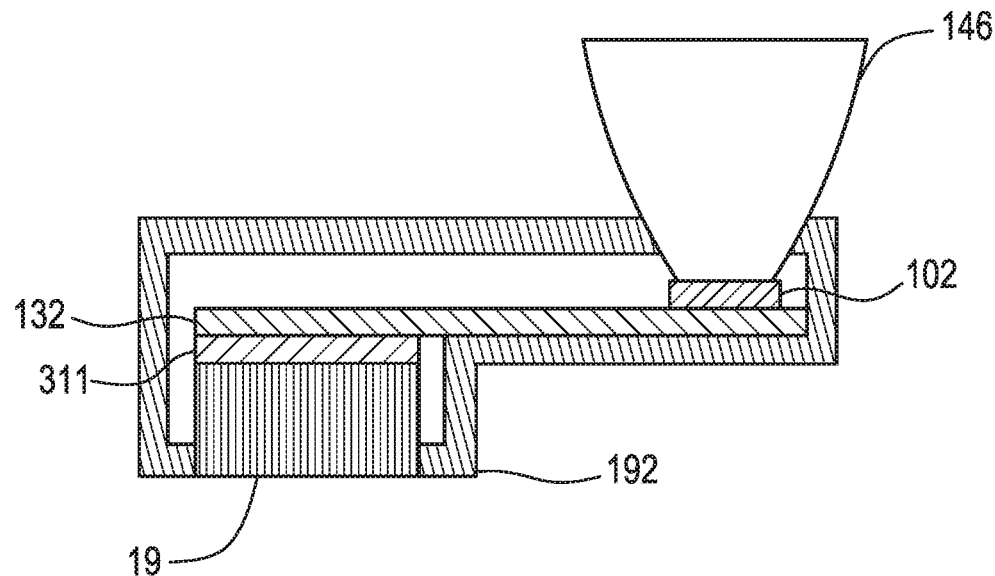
FIGS. 48A and 48B schematically show the device of FIGS. 47A-47B without a fan, respectively.
Figure 48B:
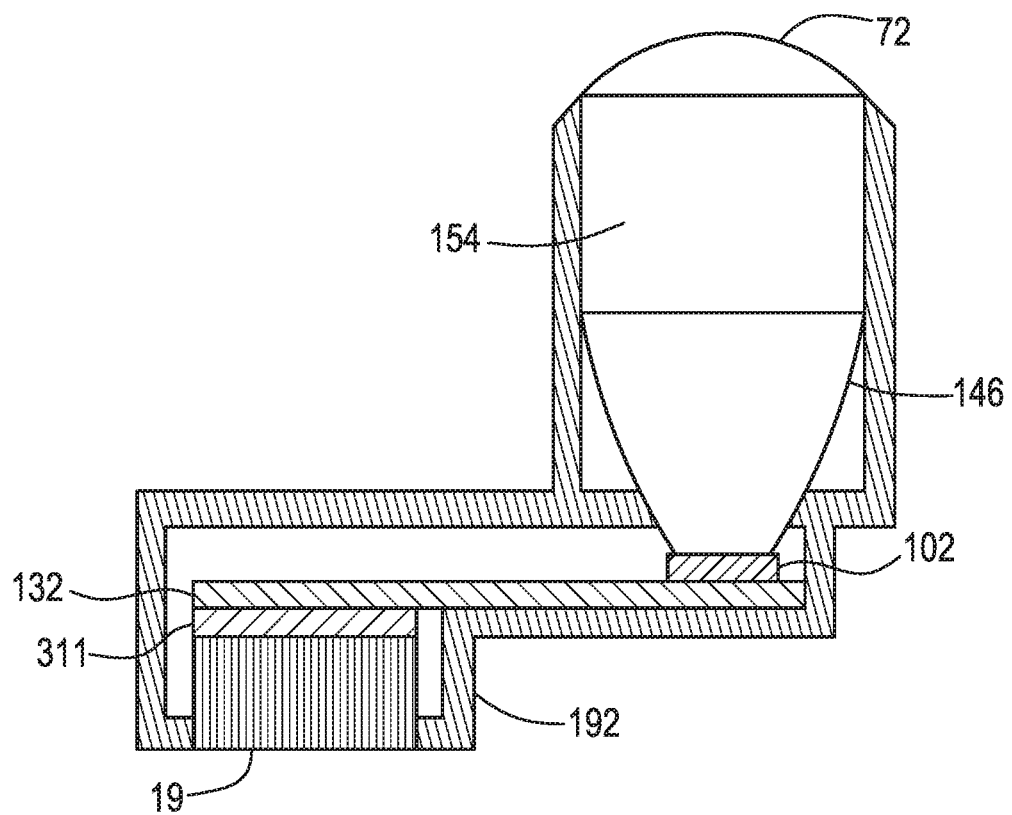

FIGS. 48A and 48B schematically show the device 100 of FIGS. 47A-47B without a fan, respectively. Some embodiments, based on how high the LED temperature peaks, may not need a fan. For some embodiments, the peltier module and heat sink may be capable of dissipating enough heat alone. For this reason, the fan could be removed to keep a lower profile on the device. In the same sense, the peltier module may prove to be unnecessary and may be removed as well. The lens system may still require additional casing to leave space between the collimator and the lens.

Figure 49A:
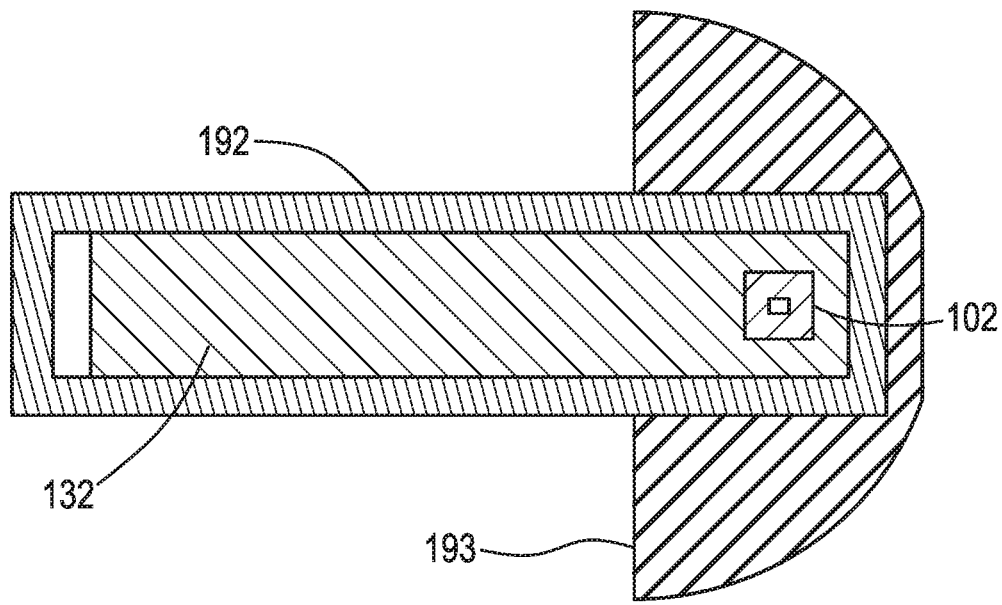
FIGS. 49A-49B schematically show a top view of the heat pipe in accordance with illustrative embodiments of the invention.
Figure 49B:
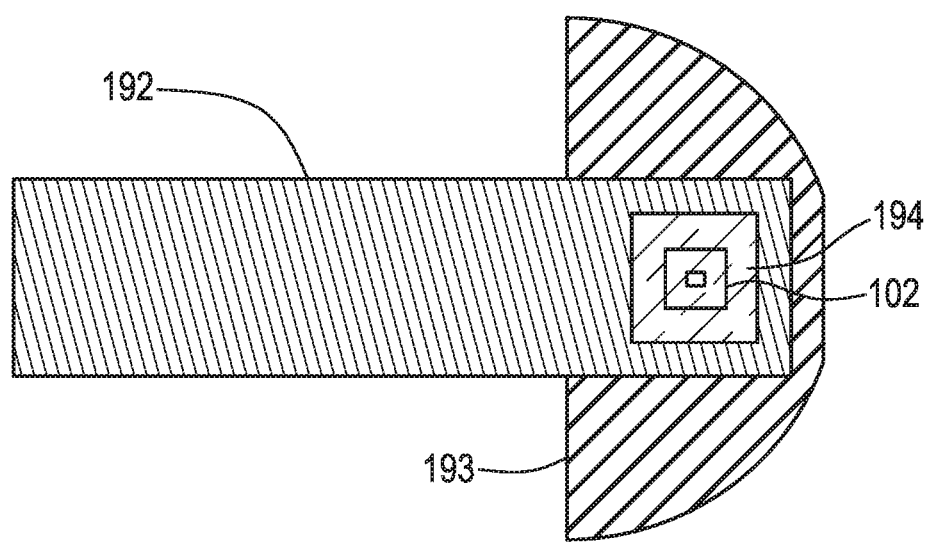

FIGS. 49A-49B schematically show a top view of the heat pipe in accordance with illustrative embodiments of the invention. FIG. 49A is a section view showing the heat pipe running the length of the device with the LED chip resting atop it on the distal end. Surrounding that is a rubber guide meant to be an ergonomic interface between the device and the upper eyelid. This is to provide the patient with a comfortable treatment experience while also ensuring that the light is penetrating in the correct area of the orbit. FIG. 49B shows a typical top-down view highlighting the outer case structure and the transparent glass plate above the LED source. Neither of these renderings show systems using the Collimator or Collimator and Lens.

Figure 50A:
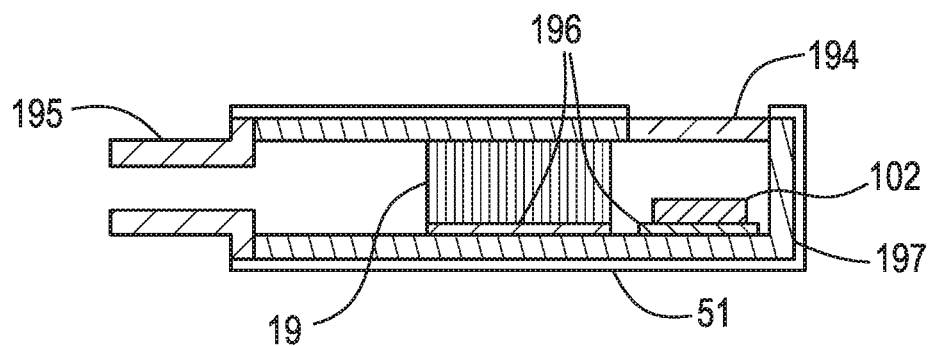
FIGS. 50A-50B schematically show side views of the device configured to use straight forced air in accordance with illustrative embodiments of the invention.
Figure 50B:
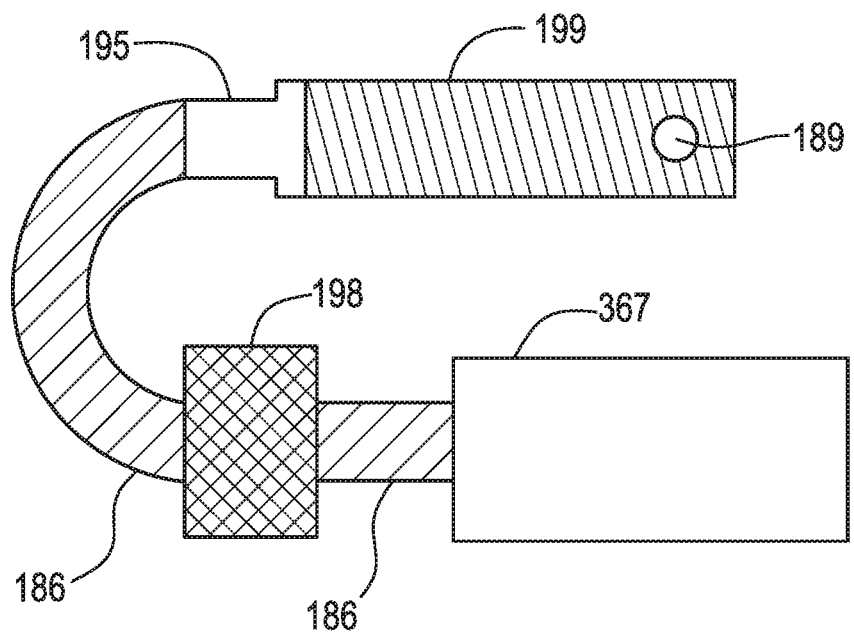

FIGS. 50A-50B schematically show side views of the device configured to use straight forced air in accordance with illustrative embodiments of the invention. FIG. 50A shows a sectioned view showing the internal structure featuring a heat sink anchored to a metal frame designed to conduct heat away from the base of the LED that is also attached to the metal frame via a Thermoelectric Cooling unit. The Pneumatic Fitting is designed to be an interface between the internal section of the pipe and the source of airflow. The air flows through the heat sink, cooling down the fins and thus the metal frame as well. The heat sink is also attached to the metal frame via a Thermoelectric Cooling unit to speed up heat transfer between the fins and the frame. The glass plate on the top serves to seal the flow from escaping out of the top of the device while allowing the LED light to still transmit through to the intended area. Surrounding the whole metal frame is a thermally insulating layer that is designed to contain the heat produced by the LED in an effort to protect the skin from excessive temperature rise. FIG. 50B the side view showing a Compressed Gas Source, this could be a tank of compressed gas or some other kind of source. From there the gas flows through tubing into a control valve that regulates how much gas can escape into the chamber of the device. This will serve as a control for how cool the device is designed to stay. Then more tubing will transport the gas to the Pneumatic Fitting on the proximal end of the pipe. The gas will exit from the Exhaust Port 187 designed to dissipate the excess heat generated by the LED system.

Figure 51:
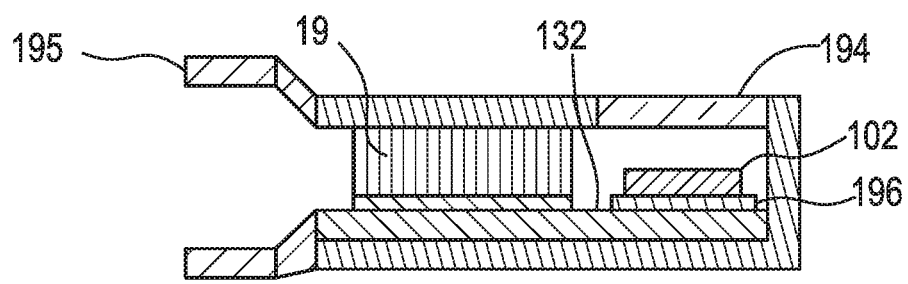
FIG. 51 schematically shows an alternative embodiment using forced air in accordance with illustrative embodiments of the invention.
Figure 52:
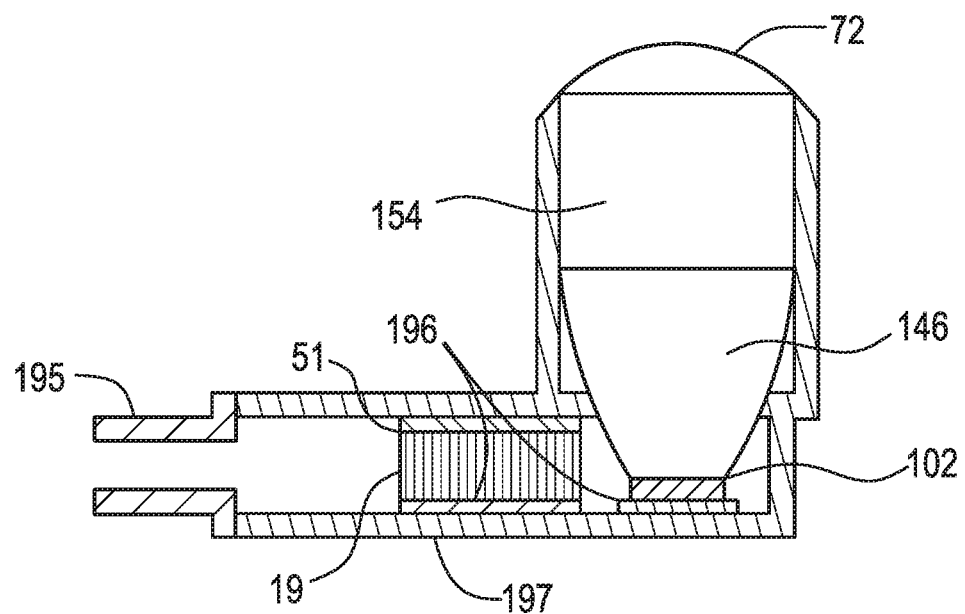
FIG. 52 schematically shows an alternative embodiment including forced air with collimator and lens.

FIG. 51 schematically shows an alternative embodiment using forced air in accordance with illustrative embodiments of the invention. The device uses a slightly different geometry in order to optimize the potential difference in the cross-sectional area from the Pneumatic tubing to the heat pipe. This unit also uses a TEC unit for additional heat transfer rates between both the metal frame and heat sink, and the metal frame and the LED FIG. 52 schematically shows an alternative embodiment including forced air with Collimator and Lens. This embodiment is similar to FIG. 51, with the exception being the Collimator system. The LED now has a Collimator placed around it in order to collimate the light in an effort to direct the light towards the target tissue at a more direct angle which increases penetration depth. The Lens placed on top of the Collimator is then able to focus the collimated light to better direct the light towards the desired treatment area. The Collimator and Lens system also acts as a thermal buffer between the LED and the tissue in order to keep the skin within a safe temperature range. The Lens must be off the Collimator a given distance so the frame will produce an air gap between the two. In addition, there is a small thermal insulator on top of the heat sink. This is to thermally isolate the bottom metal frame as the only one being cooled by the heat sink as it is the only surface in contact with the hot LED. The metal frame is interfaced with TEC units at the LED and the Heat sink in order to facilitate heat exchange.

Figure 53:
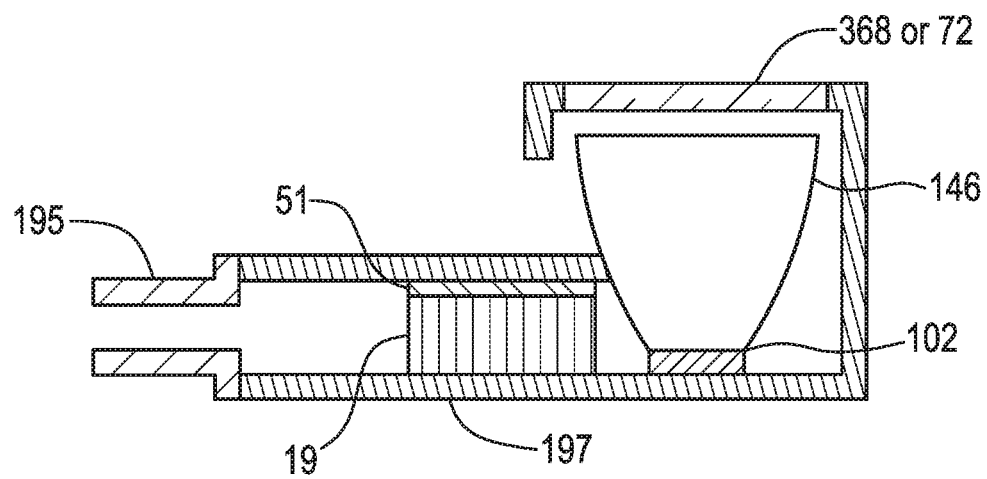
FIG. 53 schematically shows an alternative embodiment having forced air above the collimator.

FIG. 53 schematically shows an alternative embodiment having forced air above the collimator. This embodiment shows the metal frame encapsulates the Collimator instead of having the Collimator protrude from the casing. In this embodiment, the airflow would surround the Collimator and there would be an air gap between the Collimator and the clear material above it. The material could be clear glass/acrylic, some kind of lens, or another optically transparent thermal insulator. This device would not have an exhaust port 187 at the distal end of the pipe. Instead, the air would escape out of an opening between the Collimator and the Heat sink after flowing around the Collimator.

Figure 54:
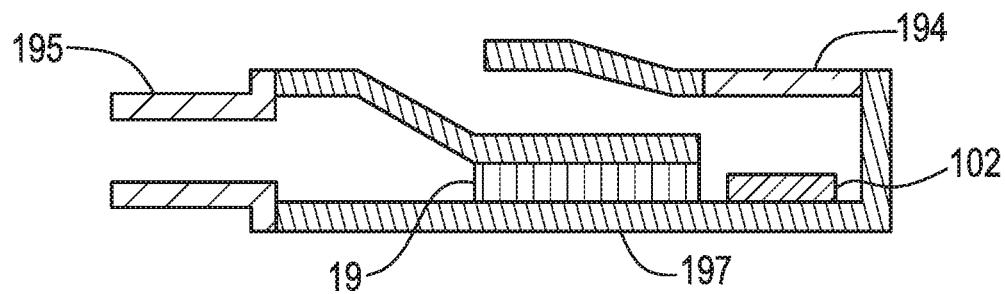
FIG. 54 schematically shows an alternative embodiment having a top vent.

FIG. 54 schematically shows an alternative embodiment having a top vent. FIG. 54 is similar to FIG. 53, (e.g., uses the same top-side air vent as FIG. 53) but this iteration does not have the Collimator. Instead, it is just the LED and an optically transparent thermal isolator like glass or acrylic.

Figure 55:
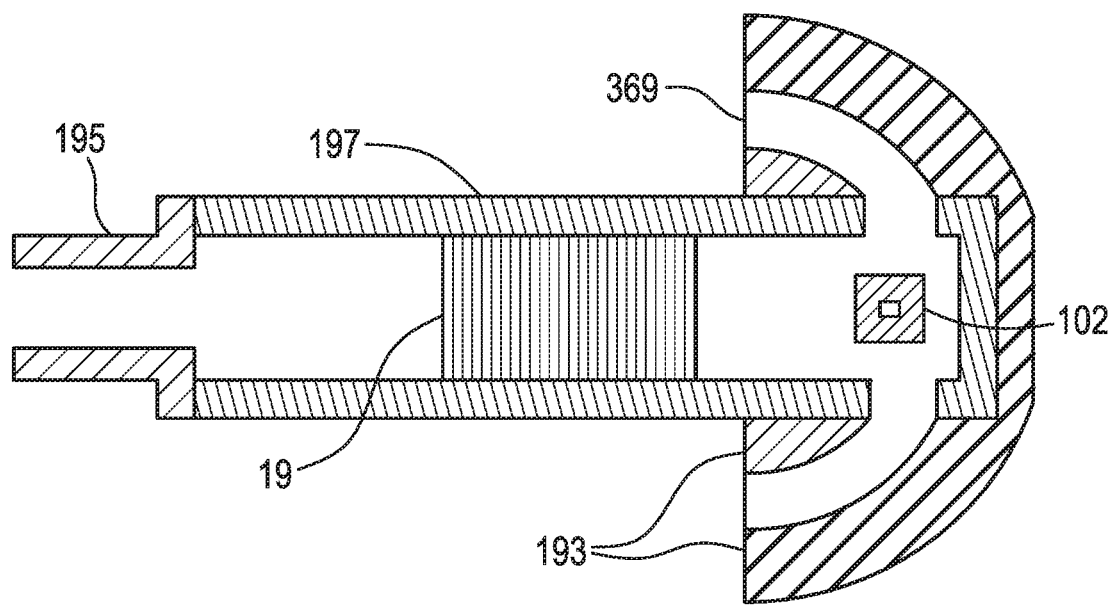
FIGS. 55-56 schematically shows an alternative embodiment using forced with a rubber guide in accordance with illustrative embodiments of the invention.
Figure 56:
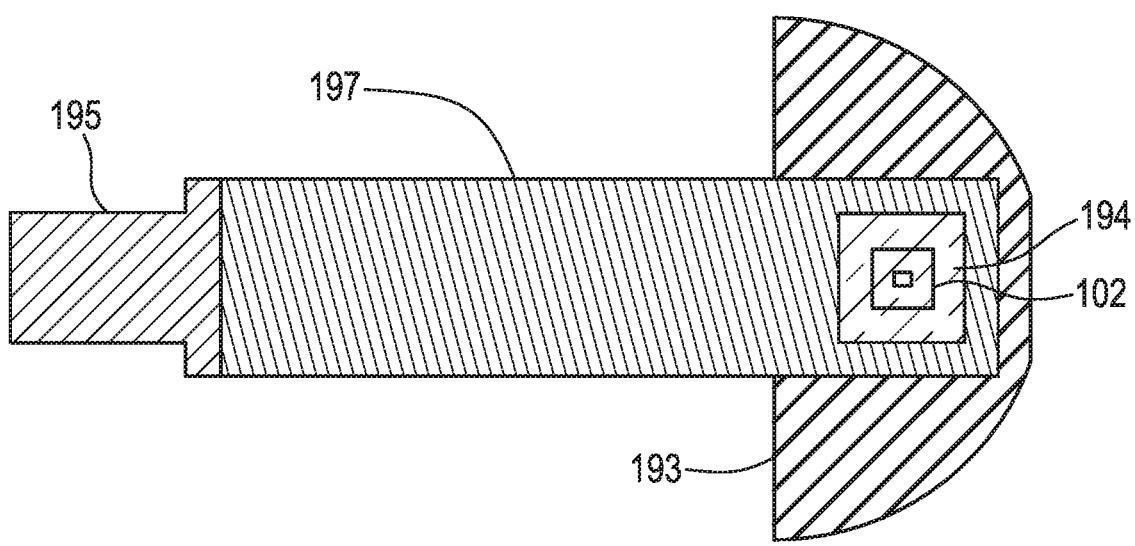

FIGS. 55-56 schematically shows an alternative embodiment using forced with a rubber guide in accordance with illustrative embodiments of the invention. These are top views of the Forced Air design. FIG. 55 is a section view showing the Rubber Guide shape with a channel for the exhaust to escape. In this design, the exhaust exits there from the guide instead of the side exhaust ports as shown in other designs. FIG. 56 shows a plain top side view of the design. This shows the shape of the Rubber Guide and the clear glass plate above the LED.

Figure 57:
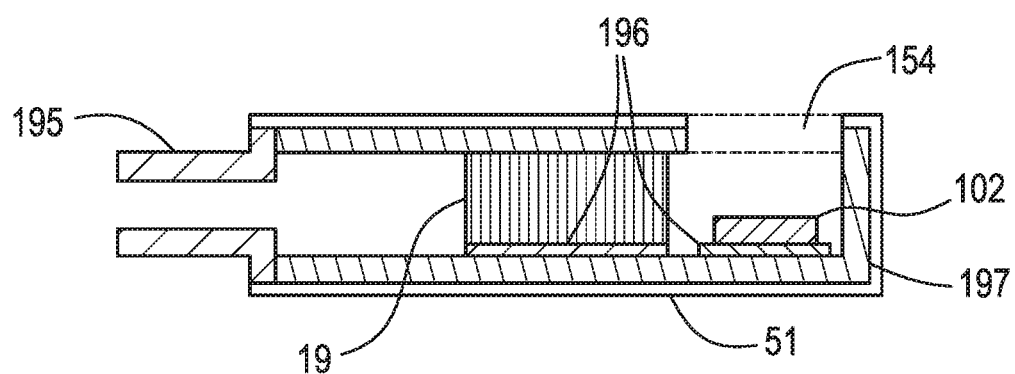
FIGS. 57-58 schematically show straight Pipe Reverse Air Flow in accordance with illustrative embodiments of the invention.
Figure 58:
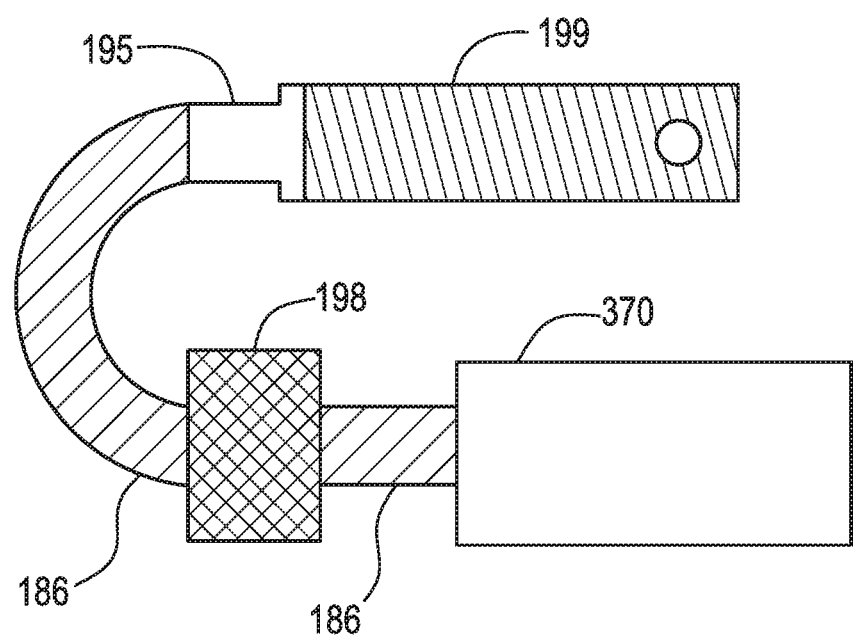

FIGS. 57-58 schematically show straight Pipe Reverse Air Flow in accordance with illustrative embodiments of the invention. Illustrative embodiments are very similar to the Straight Forced Air design, with the exception being the direction of the air flow. This embodiment utilizes a vacuum source to draw air in the opposite direction as the other pipes. The exhaust port 187 on the side of the device now acts as an air intake and the glass plate between the LED and the eye has been removed. This is for two reasons. One, the air is as cool as possible while passing over the LED, in the forward flow designs the air was heated by the heat sinks before passing over the LED. Second, the air can cool the skin first before being heated by the LED and heat sink. The air is passed directly over the skin through the opening directly above the LED. This cooling is acting to mitigate the heat generated by the thermalization of light in the tissue. This system is designed in a way that the air flow can cool the eyelid, then the LED, then pass through the heat sink fins and be exhausted.

Figure 59:
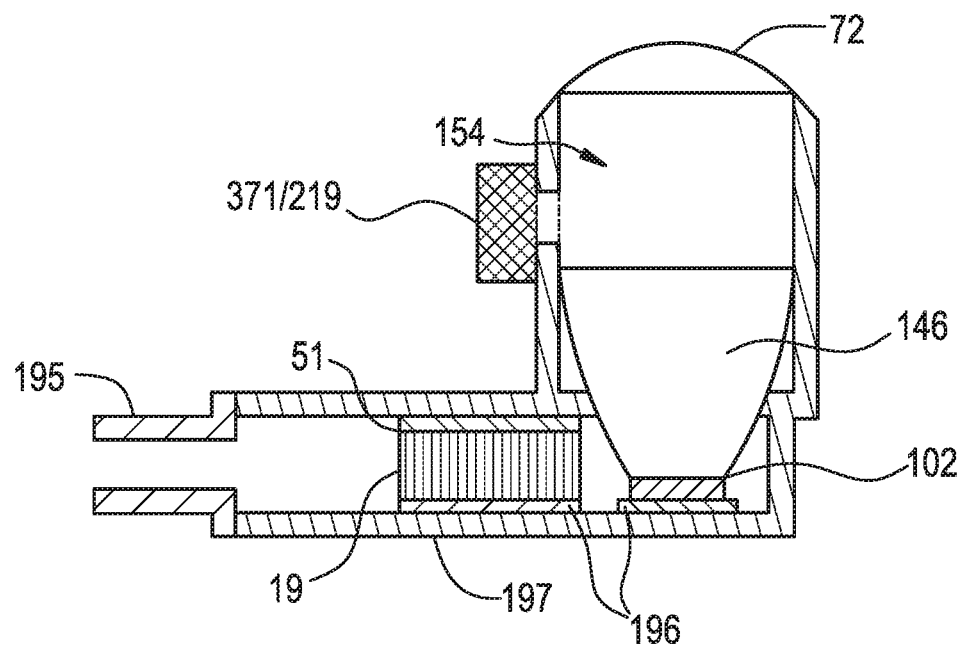
FIGS. 59-60 schematically show Reverse Air Flow with Collimators and Lens in accordance with illustrative embodiments of the invention.
Figure 60:
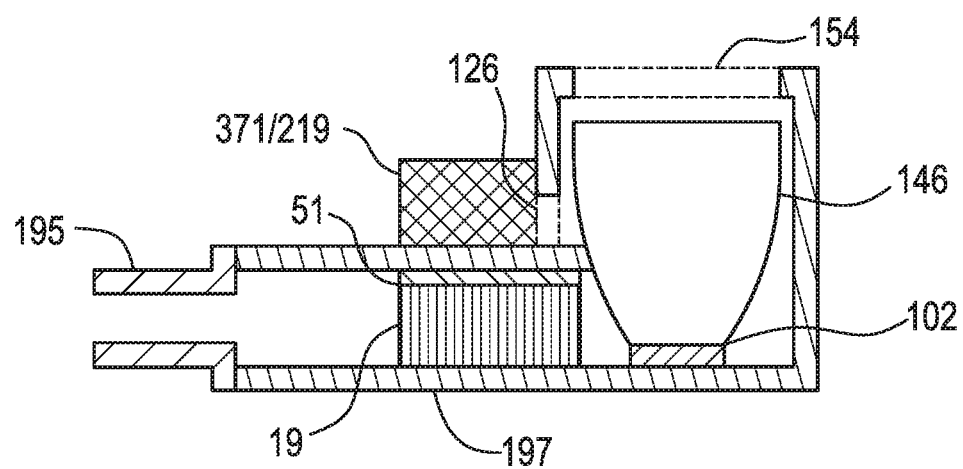

FIGS. 59-60 schematically show Reverse Air Flow with Collimators and Lens in accordance with illustrative embodiments of the invention. This embodiment features the Collimator configurations of the straight forced air embodiments, but again with the airflow being reversed. This iteration uses a pump or fan system to push cool air into the air gap surrounding the collimator. In FIG. 58, the air serves to cool the lens and thus indirectly the eyelid as well. On the second design the cool air comes into direct contact with the skin through an opening above the collimator. The air is then forced down to cool the LED, then towards the heat sink and finally exhausted out where the Pneumatic Fitting. This embodiment could also function with a vacuum pump being attached to the Pneumatic Fitting, the Fan on the top would then become an air intake vent.

Illustrative embodiments may include a second reflective surface may be added distally of the collimator in order to guide collimated light away from the eyeball and towards the orbitofrontal cortex.

Figure 61:
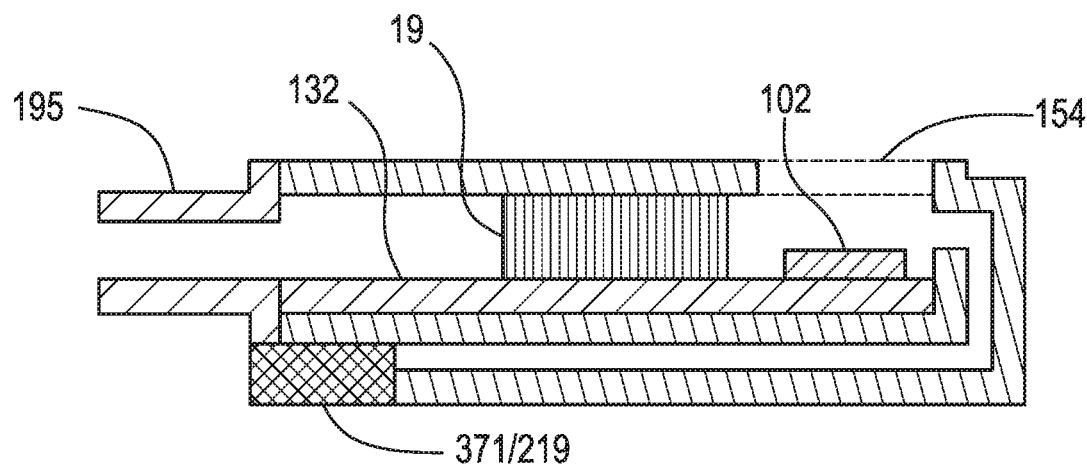
FIGS. 61-62 schematically show Alternative Reverse Air Flow in accordance with illustrative embodiments of the invention.
Figure 62:
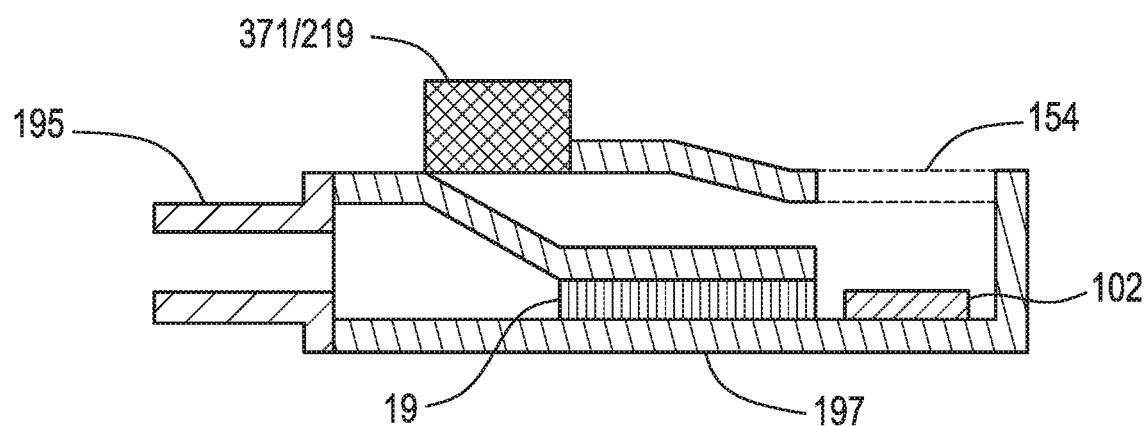

FIGS. 61-62 schematically show Alternative Reverse Air Flow in accordance with illustrative embodiments of the invention. FIGS. 61-62 are similar to the Straight Pipe Reverse Air Flow design. The difference is that these iterations have a fan or pump that is connected to a channel on one side of the pipe. This channel is to direct cool air to the distal end of the pipe. This cool air will cool the skin and LED first before passing through the heat sink and being heated further. The air will then be exhausted out the Pneumatic Fitting.

Figure 63:
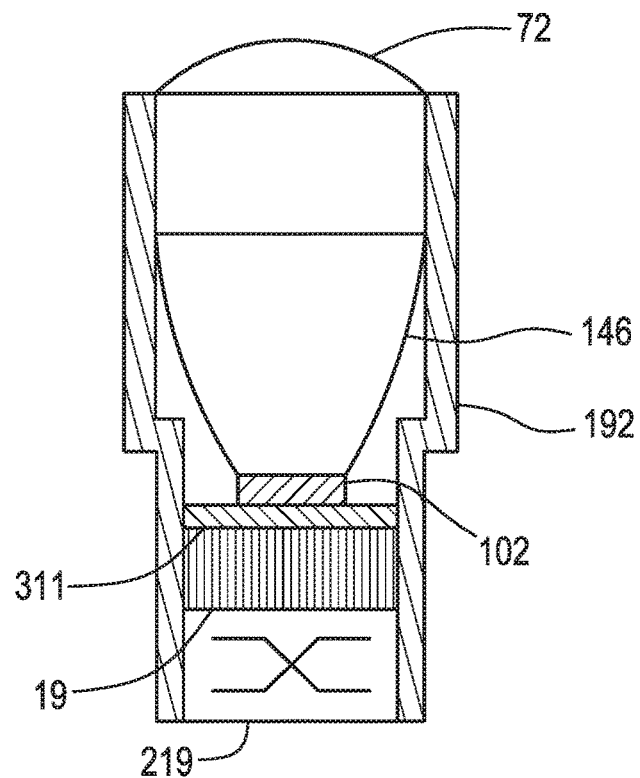
FIGS. 63-64 schematically show a collimator mounted on an LED chip in accordance with illustrative embodiments of the invention.
Figure 64:
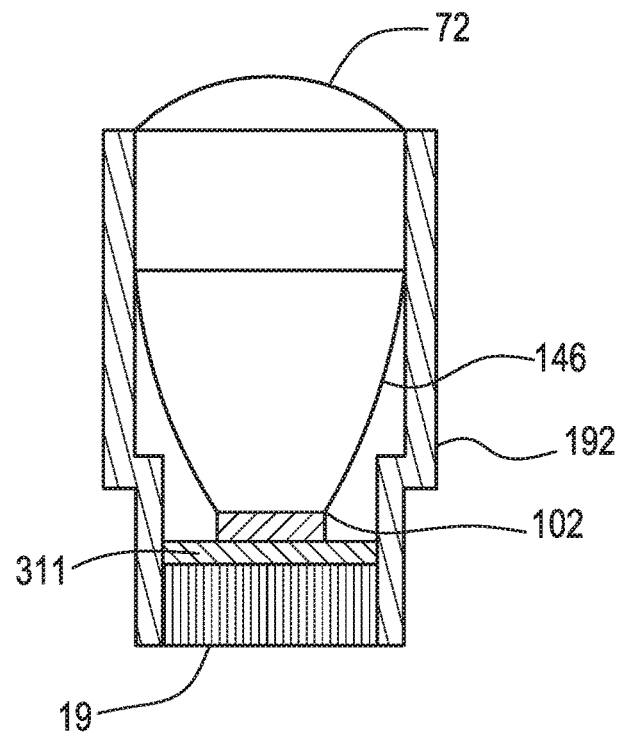

FIGS. 63-64 schematically show a collimator mounted on an LED chip. This serves to collimate the uncollimated light from the LED source. The light from the Collimator is then focused down using a Lens that is some distance away from the Collimator leaving an air gap so the Lens does not heat up. The LED is attached to a Peltier Module to keep the bottom side of the LED cool. This is beneficial for a number of reasons. Most important to us is that when an LED gets too hot it will begin to degrade and perform worse. In our case, this could lead to a change in output wavelength which could lead to lessened therapeutic impact. The Peltier Module is then mounted to a heat sink which can work in conjunction with a fan if deemed necessary. This system is configured to keep the LED cool for optimal performance while keeping the LED off the eye as much as possible.

Figure 65:
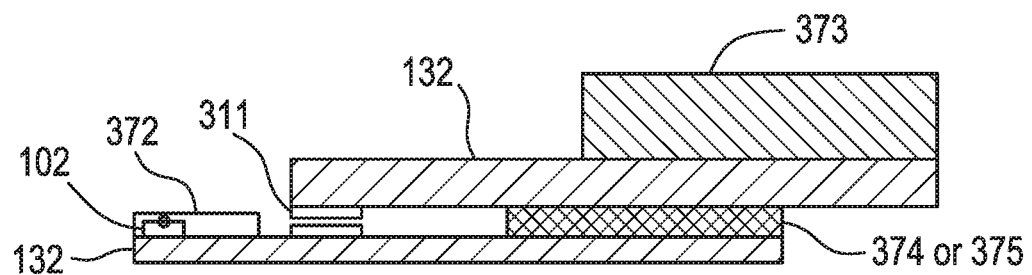
FIG. 65 schematically shows an alternative embodiment of a heat pipe concept in accordance with illustrative embodiments of the invention.

FIG. 65 schematically shows an alternative embodiment of a heat pipe concept in accordance with illustrative embodiments of the invention, the light emitting device comprises:
  a) a first heat pipe having a proximal end portion, a distal end portion, and an upper surface,
  b) a light emitter comprising a lower surface, an upper surface, and an NIR LED on the upper surface,
  c) a peltier thermoelectric element having a cold surface and a hot surface,
  d) a second heat pipe having a proximal end portion and a distal end portion, and
  e) a cooling element (such as a phase change cooling device)
wherein the lower surface of the light emitter is attached to the upper surface of the distal end portion of the first heat pipe, wherein the cold surface of the peltier thermoelectric element is attached to the proximal end portion of the first heat pipe, wherein the hot surface of the peltier thermoelectric element is attached to the distal end portion of the second heat pipe, wherein the cooling element is attached to the proximal end portion of the second heat pipe.

Figure 66:
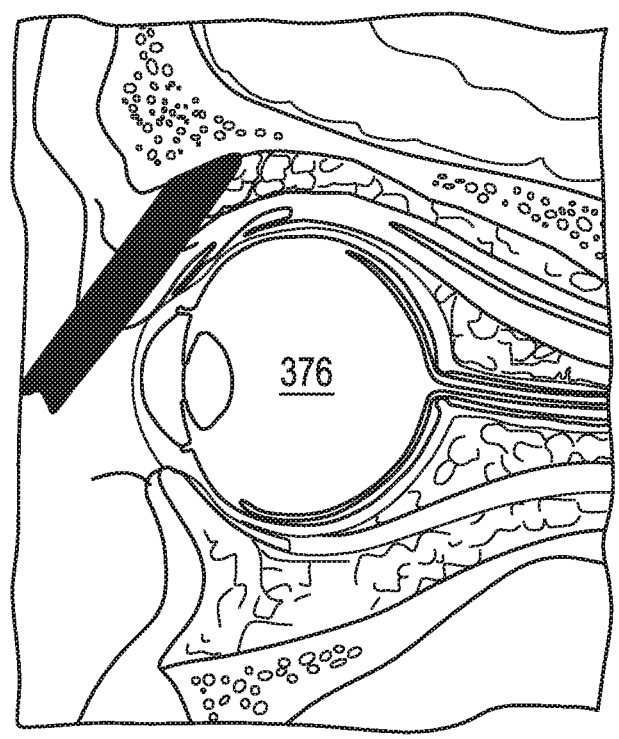
FIG. 66 schematically shows a portion of the device in the periorbital space in accordance with illustrative embodiments of the invention.

FIG. 66 schematically shows a portion of the device in the periorbital space in accordance with illustrative embodiments of the invention. In some embodiments, the distal tip of the convex side of the light pipe is angled, and light proceeds straight out of the distal end of the light pipe. This allows the light pipe to be comfortably placed on the orbit rim while allowing both maximum light flux and protection of the eyeball.

Therefore, there is provided, as in FIG. 65, a solid light pipe made of a light transparent material and having an upper surface, a lower surface, opposing side surfaces connecting the upper and lower surfaces, a proximal end portion and a distal endportion, wherein the lower and upper surfaces in the region of the distal end portion form a substantially concavo-convex shape, wherein the upper (convex) surface has an angled portion in the distal end portion extending distally inwards towards the lower (concave) surface. Preferably, an NIR LED is attached to the proximal end portion of the light pipe.

While illustrative embodiments refer to the optic as focusing collimated light, it should be understood that some embodiments do not have a collimator. Accordingly, the above discussion referring to focusing collimated light also applies to light that is not collimated.

A person of skill in the art understands that illustrative embodiments provide a number of advantages. For example, advantages include that a reflector positioned in the periorbital cavity is used to enable pulsing of light transorbitally. Otherwise, it is difficult to deliver light transorbitally. Illustrative embodiments also provide a light guide, collimator, and/or focusing optic to assist with delivering all, or substantially all, of the light to the reflector. Furthermore, illustrative embodiments optimize the amount of light delivered to the brain while minimizing the exposure of tissue (e.g., skin) to high amounts of light and remaining within the maximum permissible exposure limit.

Disclosed embodiments, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments. Additionally, although some components and/or features of the device 100 may be described as optional, illustrative embodiments should not be interpreted as requiring components and/or features that have not explicitly been described as optional.

The embodiments of the invention described above are intended to be merely exemplary; numerous variations and modifications will be apparent to those skilled in the art. Such variations and modifications are intended to be within the scope as defined by any of the appended claims.

What is claimed is:

1. A device for treating the brain, the device comprising:
   a light source configured to emit near infrared light;
   a collimator configured to receive the near infrared light emitted by the light source, the collimator further configured to collimate the near infrared light;
   a distal tip having an opening; the distal tip having a substantially concavo-convex shape configured to fit curvature of an eye;
   an optic configured to focus the collimated light towards a reflector;
   the reflector configured to change a direction of the light towards the opening of the distal tip, the reflector being at the distal tip of the device, the distal end being configured to fit in a periorbital space around a patient's eye;
   the device configured such that the light exits the distal tip through the opening towards the brain of the patients through the periorbital space.

2. The device as defined by claim 1, wherein the light source is an LED or a laser.

3. The device as defined by claim 1, further comprising a plurality of light sources.

4. The device as defined by claim 1, wherein the optic is a cylindrical lens.

5. The device as defined by claim 1, wherein the collimator is a parabolic mirror, an ellipsoidal mirror, a total internal reflection optic, a Fresnel lens, and/or a convex lens.

6. The device as defined by claim 1, further comprising a housing having therein the light source, the collimator, and the optic, wherein the reflector is outside of the housing.

7. The device as defined by claim 1, wherein the light source is configured to provide a dosage of light to the brain with an energy density of about around 1 J/cm^2.

8. A device for treating the brain, the device comprising:
   a light emitter configured to emit near infrared light;
   a collimator configured to receive the near infrared light emitted by the light emitter, the collimator further configured to collimate the near infrared light;
   an optic configured to focus the collimated light towards a reflective portion of a distal tip;
   the distal tip having a substantially concavo-convex shape configured to fit in a periorbital space around a patient's eye, and;
   a proximal end configured to receive the near infrared light from the light emitter,
   an opening through which the near infrared light exits the tip, and
   the reflective portion configured to change a direction of the near infrared light that exits the distal tip;
   wherein the device is configured such that the light exits the distal tip through the opening towards the brain of the patient through the periorbital space.

9. The device as defined by claim 8, further comprising a plurality of light emitters.

10. The device as defined by claim 8, wherein the optic is a cylindrical lens.

11. The device as defined by claim 8, wherein the distal tip is formed from a material configured to cause total internal reflection.

12. The device as defined by claim 11, wherein the material is aluminum.

13. The device as defined by claim 8, further comprising a thermo electric cooler, and/or a heat sink coupled with the light source.

14. The device as defined by claim 8, further comprising a housing having the light emitter and a portion of the distal tip therein, the housing having an open distal end through which the distal tip passes.

15. The device as defined by claim 8, wherein the reflective portion is an exposed internal surface of the material configured to cause the total internal reflection.

16. A method for treating the brain, the method comprising:
    providing a device having:
      a light emitter configured to emit near infrared light in a first direction,
      a collimator configured to receive the near infrared light emitted by the light emitter, the collimator further configured to collimate the near infrared light;
      an optic configured to focus the collimated light towards a reflective portion of a distal tip;
      the distal tip having:
        a substantially concavo-convex shape configured to fit in a periorbital space around a patient's eye, and
        a proximal end configured to receive the near infrared light from the light emitter,
        an opening through which the near infrared light exits the distal tip, and
        the reflective portion configured to change the direction of the light from a first direction to a second direction; and
    positioning at least a portion of the device in an orbital cavity of the patient, such that the second direction is toward an orbitofrontal cortex of the brain of the patient.

17. The method as defined by claim 16, further comprising:
    emitting a therapeutic dose of near infrared light from the light emitter;
    reflecting the emitted near infrared light transorbitally towards the orbitofrontal cortex of the patient.

18. The method as defined by claim 16, further comprising actuating the LED so that the NIR light exits the LED and is substantially collimated in the collimator.

19. The method as defined by claim 16, wherein the positioning includes placing the reflector about 10 mm into the orbital socket from a surface of a frontal bone of the patient.

* * * * *